(12) United States Patent
Devos et al.

(10) Patent No.: US 8,623,599 B2
(45) Date of Patent: *Jan. 7, 2014

(54) METHOD FOR METHYLATION ANALYSIS

(75) Inventors: Theo Devos, Seattle, WA (US); Cathy Lofton-Day, Seattle, WA (US); Andrew Sledziewski, Shoreline, WA (US); Fabian Model, Berlin (DE); Michael Krouse, Seattle, WA (US); Jesse Ho, Seattle, WA (US); Matthias Schuster, Singapore (SG); Juergen Distler, Berlin (DE); Reimo Tetzner, Berlin (DE)

(73) Assignee: Epigenomics AG, Berlin (DE)

( * ) Notice: Subject to any disclaimer, the term of this patent is extended or adjusted under 35 U.S.C. 154(b) by 570 days.

This patent is subject to a terminal disclaimer.

(21) Appl. No.: 12/451,943

(22) PCT Filed: Jun. 6, 2008

(86) PCT No.: PCT/IB2008/002118
§ 371 (c)(1),
(2), (4) Date: Sep. 10, 2010

(87) PCT Pub. No.: WO2008/149237
PCT Pub. Date: Dec. 11, 2008

(65) Prior Publication Data
US 2011/0009277 A1 Jan. 13, 2011

(30) Foreign Application Priority Data

Jun. 8, 2007 (EP) .................................... 07109907
Jun. 15, 2007 (EP) .................................... 07110409
Jul. 31, 2007 (EP) .................................... 07113516
Aug. 21, 2007 (EP) .................................... 07114659
Aug. 23, 2007 (EP) .................................... 07114863
Jan. 23, 2008 (EP) .................................... 08150552
Feb. 14, 2008 (EP) .................................... 08151442

(51) Int. Cl.
*C12Q 1/68* (2006.01)
(52) U.S. Cl.
USPC .......................................... 435/6.1; 435/6.11
(58) Field of Classification Search
USPC ................................................. 435/6.1, 6.11
See application file for complete search history.

(56) References Cited

U.S. PATENT DOCUMENTS 7,749,702 B2 * 7/2010 Lofton-Day et al. ........ 435/6.12
2006/0286576 A1 * 12/2006 Lofton-Day et al. ............. 435/6

FOREIGN PATENT DOCUMENTS

WO 2006113770 A1 10/2006

* cited by examiner

*Primary Examiner* — Michele K Joike
*Assistant Examiner* — Antonio Galisteo Gonzalez
(74) *Attorney, Agent, or Firm* — Kriegsman & Kriegsman

(57) ABSTRACT

Aspects of the invention relate to composition and methods for the providing of DNA for methylation analysis that is in particular suitable to be applied in reference laboratories. Further 5 aspects of the invention relate to composition and methods for the highly specific and sensitive methylation analysis of the Septin 9 gene also in particular suitable to be applied in reference laboratories.

6 Claims, 9 Drawing Sheets

METHOD FOR METHYLATION ANALYSIS

FIELD OF THE INVENTION

The invention relates generally to novel and substantially improved compositions and methods for providing DNA for methylation analysis, in particular for methylation analysis of the septin 9 gene. The invention further relates generally to novel and substantially improved compositions and methods for methylation analysis of the septin 9 gene.

BACKGROUND OF ASPECTS OF THE INVENTION

Development of a Medical Test.

The probability of curing a disease (e.g. a cancer disease) is many times predominantly dependent from an early as possible detection of the disease. It is also often advantageous to detect a predisposition for a disease or if for example the disease is already advanced to make an estimation for the most promising treatment for the disease. Such an early as possible detection, prediction or estimation reduces the costs for direct and associated medical treatment. It ensures also a higher quality of life for the affected patient.

This leads to the situation that a lot of samples derived from individuals with a suspected disease have to be tested, the majority may not be affected by the disease. Or, in case of patients with a diagnosed disease, a lot of samples have to be tested, and only a small percentage will respond to a certain treatment. Usually the majority of said tests is performed in so-called reference laboratories. Because of the huge number of samples which are processed in reference laboratories, the actual test and the corresponding workflow of processing the sample underlie the following requirements: combinable with methods of carry over prevention; low demands on laboratory equipment; low handling effort; capable of being automated by means of robotics or manually; capable of being standardized; realizable in plate scale; high yield of DNA in order to reduce the amount of sample and to increase the sensitivity and specificity; high sensitivity; high specificity; low costs; DNA free of interfering compounds such as but not limited to proteins, RNA, nucleotides or disturbing chemical reagents; high reproducibility and high reliability.

Furthermore, in general, it is desirable that a test should have a high as possible sensitivity, a high as possible specificity and a high as possible accuracy. Sensitivity is a measure of a test's ability to correctly detect the target disease in an individual being tested. A test having poor sensitivity produces a high rate of false negatives, i.e., Individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. Mathematical it can be described as: Sensitivity=TP/(TP+FN). Thereby TP represents a true positive result and FN a false negative result. A true positive result means that the test is positive and the condition is present while a false negative result is where the test is negative but the condition is not present.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures or treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state. Mathematical specificity can be described as: Specificity=TN/(FP+TN). Thereby TN represents a true negative result and FP a false positive result. A true negative result is where the test is negative and the condition is not present. A false positive result is where the test is positive but the condition is not present.

Starting Material for a Test.

It is advantageous for a test with regard to cost reduction and to a high quality of life of the patient that it can be performed non-invasively. If this is not possible, it is desirably to perform it by invasive means which affect as less as possible the patient, which are easy to perform, which cause low costs or combinations thereof. Because of that, remote samples such as but not limited to blood, sputum, stool or body fluids are the starting material of choice for a test.

However, the use of remote samples is quite limited by the low amount of DNA, in particular by the low amount of DNA which originates by the diseased cell or tissue. Therefore the workflow from the sample collecting to the start of the test has to be characterized by high yields of DNA.

Furthermore, the DNA of interest might be partially degraded in a remote sample. This depends on the type of the remote sample and also on the way of collecting and handling the remote sample. A fragmentation of DNA in remote sample down to a fragment size of 100 bp and under it is possible. Therefore a workflow from collecting a sample to the start of a test should ensure that small DNA fragments as well as large DNA fragments are provided and that the DNA does not get further fragmented. Numerous documents exist which address these problems. Exemplary only the following are cited herein: Diehl F., et al. (2005) PNAS 102(45), 16368-16373; and Li J., et al. (2006) Journal of Molecular Diagnostics, 8(1), 22-30.

Methylation Analysis.

As revealed in recent years, one of the most powerful and promising approaches for detecting a disease, the pre-disposition for a disease or for estimating a probable response with respect to a certain disease treatment is the methylation analysis of the patient's genomic DNA.

Many diseases, in particular cancer diseases, are accompanied by modified gene expression. This may be a mutation of the genes themselves, which leads to an expression of modified proteins or to an inhibition or over-expression of the proteins or enzymes. A modulation of the expression may however also occur by epigenetic modifications, in particular by changes in the DNA methylation pattern. Such epigenetic modifications do not affect the actual DNA coding sequence. It has been found that DNA methylation processes have substantial implications for health, and it seems to be clear that knowledge about methylation processes and modifications of the methyl metabolism and DNA methylation are essential for understanding diseases, for the prophylaxis, diagnosis and therapy of diseases.

The precise control of genes, which represent a small part only of the complete genome of mammals, involves regulation in consideration of the fact that the main part of the DNA in the genome is not coding. The presence of such 'trunk' DNA containing introns, repetitive elements and potentially actively transposable elements, requires effective mechanisms for their durable suppression (silencing). Apparently, the methylation of cytosine by S-adenosylmethionine (SAM)

dependent DNA methyl transferases, which form 5-methylcytosine, represents such a mechanism for the modification of DNA-protein interactions. Genes can be transcribed by methylation-free promoters, even when adjacent transcribed or not-transcribed regions are widely methylated. This permits the use and regulation of promoters of functional genes, whereas the trunk DNA including the transposable elements is suppressed. Methylation also takes place for the long-term suppression of X-linked genes and may lead to either a reduction or an increase of the degree of transcription, depending on where the methylation in the transcription units occurs.

Nearly the complete natural DNA methylation in mammals is restricted to cytosine-guanine (CpG) dinucleotide palindrome sequences, which are controlled by DNA methyl transferases. CpG dinucleotides are about 1 to 2% of all dinucleotides and are concentrated in CpG islands. According to an art-recognized definition, a region is considered as a CpG island when the C+G content over 200 bp is at least 50% and the percentage of the observed CG dinucleotides in comparison to the expected CG dinucleotides is larger than 0.6 (Gardiner-Garden, M., Frommer, M. (1987) J. Mol. Biol. 196, 261-282). Typically, CpG islands have at least 4 CpG dinucleotides in a sequence of a length of 100 bp.

CpG islands located in promotor regions frequently have a regulatory function for the expression of the corresponding gene. For example, in case the CpG island is hypomethylated, the gene can be expressed. On the other hand, hypermethylation frequently leads to a suppression of the expression. Normally tumor suppressor genes are hypomethylated. But if they become hypermethylated, their expression becomes suppressed. This is observed many times in tumor tissues. By contrast, oncogenes are hypermethylated in healthy tissue, whereas they are hypomethylated in many times in tumor tissues.

The methylation of cytosine has the effect that the binding of proteins is normally prohibited which regulate the transcription of genes. This leads to an alteration of the expression of the gene. Relating to cancer, the expression of genes regulating cell division are thereby altered, for example, the expression of an apoptotic gene Is down regulated, while the expression of an oncogene is up regulated. Additionally, hypermethylation may have a long term influence on regulation. Proteins, which deacetylate histones, are able to bind via their 5-methylcytosine binding domain to the DNA when the cytosines get methylated. This results in a deacetylation of the histones, which itself leads to a tighter package of the DNA. Because of that, regulatory proteins are not precluded from binding to the DNA.

The efficient detection of DNA methylation patterns consequently is an important tool for developing new approaches to understand diseases, for the prevention, diagnosis and treatment of diseases and for the screening for disease associated targets.

Background of the Septin 9 Gene.

The human Septin 9 gene (also known as MLL septin-like fusion protein, MLL septin-like fusion protein MSF-A, Sipa, Eseptin, Msf, septin-like protein Ovarian/Breast septin (Ov/Br septin) and Septin D1) is located on chromosome 17q25 within contig AC068594.15.1.168501 and is a member of the Septin gene family. The Septin 9 gene is known to comprise four transcript variants, the Septin 9 variants and the Q9HC74 variants (which are truncated versions of the Septin 9 transcripts). The Septin 9 and Q9HC74 transcripts comprise each a CpG rich promotor region, respectively. It has been postulated that members of the Septin gene family are associated with multiple cellular functions ranging from vesicle transport to cytokinesis. Disruption of the action of Septin 9 results in incomplete cell division, see Surka, M. C., Tsang, C. W., and Trimble, W. S. Mol Biol Cell, 13: 3532-45 (2002). Septin 9 and other proteins have been shown to be fusion partners of the protooncogene MLL suggesting a role in tumorogenesis, see Osaka, M, Rowley, J. D. and Zeleznik-Le, N. J. PNAS, 96:6428-6433 (1999). Burrows et al. reported an in depth study of expression of the multiple isoforms of the Septin 9 gene in ovarian cancer and showed tissue specific expression of various transcripts, see Burrows, J. F., Chanduloy, et al. S. E. H. Journal of Pathology, 201:581-588 (2003). A recent study of over 7000 normal and tumor tissues indicates that there is consistent over-expression of Septin 9 isoforms in a number of tumor tissues, see Scott, M., Hyland, P. L., et al. Oncogene, 24: 4688-4700 (2005). The authors speculate that the gene is likely a type II cancer gene where changes in RNA transcript processing control regulation of different protein products, and the levels of these altered protein isoforms may provide answers to the gene's role in malignancy.

State of the Art.

As the closest prior art, the following documents may be considered:

Utting M., et al. (2002) Clinical Cancer Research 8, 35-40, This study indicates that microsatellite marker analysis using free-floating DNA of urine or blood could be relevant for diagnosis and screening of bladder cancer. The sample providing as well as the providing of DNA from the samples is carried out according to standard procedures.

Wong I. H. N., et al. (2003) Clinical Cancer Research 9, 047-1052 describe a new method named RTQ-MSP which is a combination of MSP (methylation sensitive PCR) and real-time PCR. The authors demonstrate that a detection of a particular tumor-derived DNA sequence in plasma, serum and blood cells of already diagnosed hepatocellular carcinoma patients is possible.

U.S. Pat. No. 6,927,028 teaches a method for differentiating DNA species originating form cells of different individuals in biological samples by means of methylation specific PCR. The sample providing as well as the providing of DNA from the samples is carried out according to standard procedures.

Lecomte T., et al. (2002) Int. J. Cancer 100, 542-548 tested free-circulating DNA derived from plasma of colorectal cancer patients for the presence of KRAS2 mutations, for p16 gene promoter methylation, or both. The authors suggest, patients with free-circulating tumor-associated DNA in the blood have a lower probability of a 2-year recurrence-free survival than patients for who no free-circulating tumor-associated DNA in the blood is detected.

WO 2006/039563 relates to compositions and methods for providing DNA fragments from an archived sample like paraffin-embedded and/or formalin-fixed tissue biopsies. It discloses methods wherein high yields of DNA are isolated as well as a substantial portion of the DNA consists of long DNA fragments, and where the isolated genomic DNA is free of associated or cross-linked contaminants like proteins, peptides, amino acids or RNA. The methods are facile, cost-effective, and are characterized by high reproducibility and reliability. Particularly, methods are disclosed for providing DNA fragments derived from an archived sample, wherein the yield of DNA before an amplification step is at least 20%, and amplicons up to a length of about 1,000 base pairs are amplifiable.

WO 2006/113770 discloses compositions and methods for providing DNA fragments from a remote sample. Accordingly, DNA is isolated from the remote sample, and the isolated DNA is treated in a way which allows differentiation of methylated and unmethylated cytosine. Additional, particular embodiments provide compositions and methods for methylation analysis of DNA derived from a remote sample. WO 2006/113770 discloses compositions and methods of whole genome amplification of bisulfite treated DNA.

WO 2006/113466, EP 1721992 and US 20060286576 provide methods, nucleic acids and kits for detecting, or for detecting and distinguishing between or among liver cell proliferative disorders or for detecting, or for detecting and distinguishing between or among colorectal cell proliferative disorders based on the Septin 9 gene and its methylation. Particular aspects disclose and provide genomic sequences of the Septin 9 gene, the methylation patterns of which have substantial utility for the improved detection of and differentiation between said class of disorders, thereby enabling the improved diagnosis and treatment of patients.

However, non of the methods of the state of the art is suitable for the application in reference laboratories. Therefore a pronounced need in the art exists for compositions and methods for providing DNA for methylation analysis that is suitable for the use in reference laboratories. Therefore, in addition, a pronounced need in the art exists for compositions and methods for the analysis of the methylation of the Septin 9 gene that is applicable in reference laboratories.

DETAILED DESCRIPTION OF ASPECTS OF THE INVENTION

Figure 1:
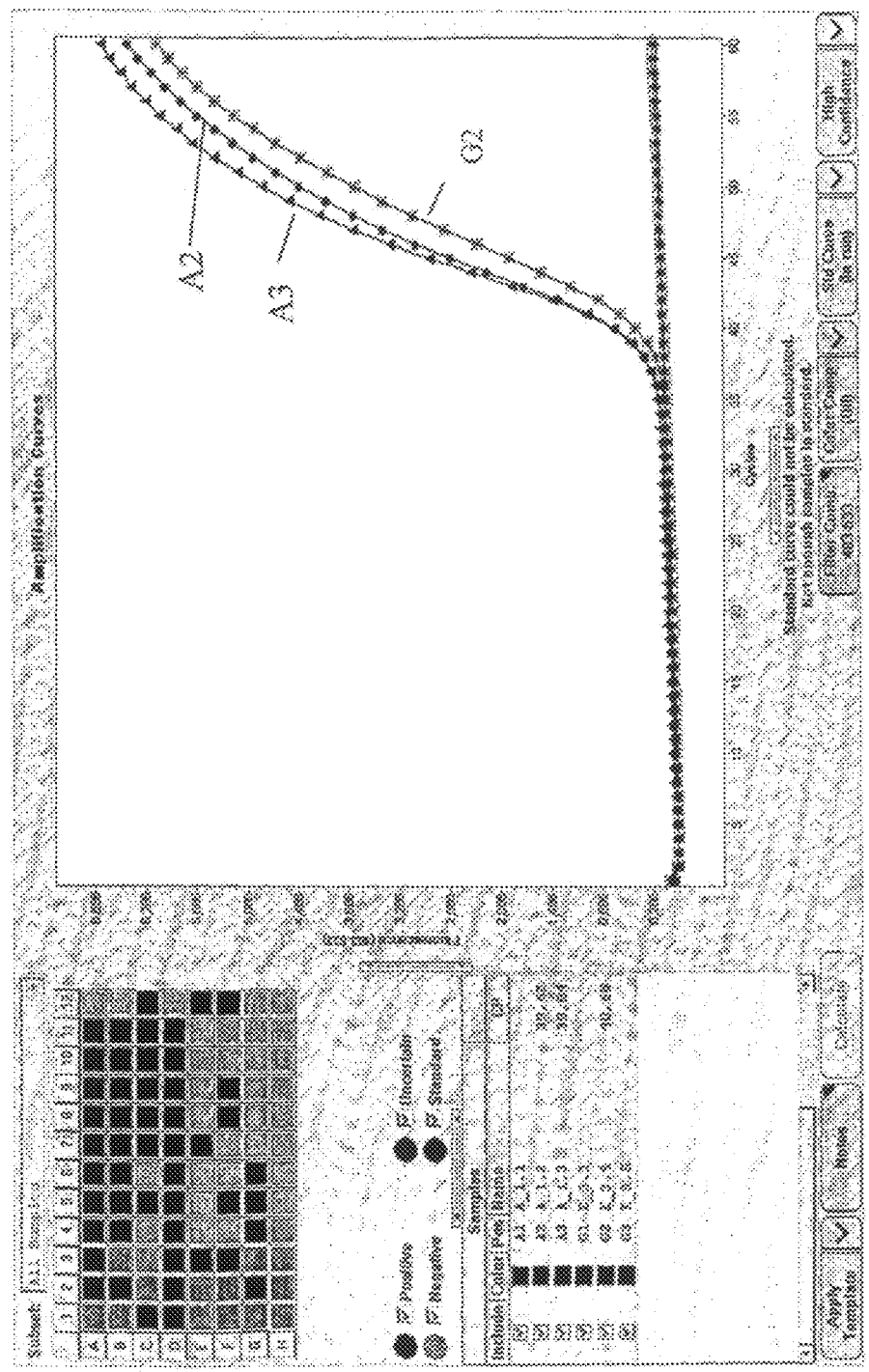
FIG. 1: Representative amplification curves of 6 samples analyzed by the Septin 9 duplex HeavyMethyl PCR. The signals obtained in channel 533 nm is specific for the PCR1.

For achieving various technical objectives, aspects of the invention teach compositions and methods for providing DNA for methylation analysis. Said compositions and methods comprise isolating genomic DNA from a sample by means of SiMAG/FK-Silanol beads or beads of the chemagic Viral DNA/RNA Kit special; and subjecting the Isolated DNA to a treatment wherein cytosine is converted to uracil sulfonate or another base having a different binding behavior than cytosine, while methylated cytosine remains unchanged.

For achieving various technical objectives, aspects of the invention teach compositions and methods for providing DNA for methylation analysis. Said compositions and methods comprise subjecting genomic DNA to a treatment wherein cytosine is converted to uracil sulfonate or another base having a different binding behavior than cytosine, while methylated cytosine remains unchanged; and purifying the treated DNA by means of SiMAG/FK-Silanol beads or beads of the chemagic Viral DNA/RNA Kit special.

For achieving various technical objectives, aspects of the invention teach compositions and methods for methylation analysis. Said methods comprises
  a) treating the genomic DNA with one or more reagents to convert unmethylated cytosine bases to uracil sulfonate or to another base having a different binding behavior than cytosine, while methylated cytosine remains unchanged;
  b) amplifying the treated DNA by means of
    i) at least one oligonucleotide comprising or consisting essentially of a sequence selected from the group consisting of SEQ ID NO: 1, 12-15, SEQ ID NO: 6, 44-48, SEQ ID NO: 6, 48, 62-64;
    ii) at least one oligonucleotide comprising or consisting essentially of a sequence selected from the group consisting of SEQ ID NO: 2, 16-22, SEQ ID NO: 5, 43, SEQ ID NO: 65-72; and
  c) deducing the methylation from the result of step b).
Said Composition Comprises
  i) at least one oligonucleotide comprising or consisting essentially of a sequence selected from the group consisting of SEQ ID NO: 1, 12-15, SEQ ID NO: 6, 44-48, SEQ ID NO: 6, 48, 62-64 usable as a primer;
  ii) at least one oligonucleotide comprising or consisting essentially of a sequence selected from the group consisting of SEQ ID NO: 2, 16-22, SEQ ID NO: 5, 43, SEQ ID NO: 65-72 usable as a primer; and optional, one or more reagents to convert unmethylated cytosine bases to uracil sulfonate or to another base having a different binding behavior than cytosine, while methylated cytosine remains unchanged.

For achieving various technical objects, aspects the invention teach compositions and methods for detecting and/or classifying cellular proliferative disorders. Said method comprises:

a) treating genomic DNA with one or more reagents to convert unmethylated cytosine bases to uracil sulfonate or to another base having a different binding behavior than cytosine, while methylated cytosine remains unchanged;
b) amplifying the bisulfit treated DNA by means of
   i) at least one oligonucleotide comprising or consisting essentially of a sequence selected from the group consisting of SEQ ID NO: 1, 12-15, SEQ ID NO: 6, 44-48, SEQ ID NO: 6, 48, 62-64;
   ii) at least one oligonucleotide comprising or consisting essentially of a sequence selected from the group consisting of SEQ ID NO: 2, 16-22, SEQ ID NO: 5, 43, SEQ ID NO: 65-72; and
c) deducing the methylation from the result of step b), wherein at least one of detecting and classifying cellular proliferative disorders is, at least in part, afforded.

Said Composition Comprises:
i) at least one oligonucleotide comprising or consisting essentially of a sequence selected from the group consisting of SEQ ID NO: 1, 12-15, SEQ ID NO: 6, 44-48, SEQ ID NO: 6, 48, 62-64;
ii) at least one oligonucleotide comprising or consisting essentially of a sequence selected from the group consisting of SEQ ID NO: 2, 16-22, SEQ ID NO: 5, 43, SEQ ID NO: 65-72; and optional,
one or more reagents to convert unmethylated cytosine bases to uracil sulfonate or to another base having a different binding behavior than cytosine, while methylated cytosine remains unchanged.

Particular aspects provide methods to find amongst an enormous plurality of known methods for providing DNA for methylation analysis those methods, which in principle can be used to solve the technical object of the invention. Particular aspects provide methods to find amongst an enormous plurality of known methods for methylation analysis those methods, which in principle can be used to solve the technical object of the invention.

Particular aspects provide methods to find amongst an enormous plurality of known methods for detecting and/or classifying cellular proliferative disorders those methods, which in principle can be used to solve the technical object of the invention.

Advantages of Aspects of the Invention.

In particular aspects, the exemplary inventive method has the following advantages:

It is characterized by high yields of provided DNA. This is achieved although many samples such as but not limited to remote samples are characterized in that they comprise only low levels of DNA, especially low levels of DNA of interest. On the other hand, in many cases the amount of a sample (remote sample) is not limited. Therefore according to the invention large amount of samples are preferably processed. In particular, DNA isolation methods were selected amongst the enormous number of possible DNA isolation methods which allow the use of large volumes of starting material. Also in particular, methods for the purification of bisulfite treated DNA were selected amongst the enormous number of possible DNA purification methods, which are characterized by high yields of bisulfite treated DNA.

The exemplary inventive method is further characterized by a low handling effort. The selected methods for DNA isolation, bisulfite treatment and purification of bisulfite treated DNA were selected amongst the enormous number of possible methods for DNA isolation, bisulfite treatment and DNA purification because of their low handling effort. The handling effort is in particular critical when it comes to the analysis of huge numbers of samples as for example but not limited to in references laboratories where an enormous number of patient samples are analyzed. Because of its low handling effort, the method of the invention is characterized in that it can be applied in high through put processes.

The exemplary inventive method is further characterized in that the whole method or parts thereof are capable of being automated for example by means of robots. Of course, the whole method or parts thereof are capable of being performed manually. Also a standardization is possible. In addition, it is possible to carry out the exemplary inventive method in plate scale.

The exemplary inventive method is further characterized in that it makes only low demands on laboratory equipment to isolate DNA, bisulfite treat it and to purify the treated DNA. Therefore it can be applied in most laboratories and is in particular suitable for reference laboratories.

The exemplary inventive method is further characterized in that it is easily combinable with the method of carry over prevention as disclosed by WO 2006/040187. According to the method of the invention, DNA is treated with bisulfite so that unmethylated cytosines are converted to uracil sulfonate, while methylated cytosines remain unchanged. After purification, the so treated DNA is subjected to a detection reaction such as but not limited to PCR amplification. For carry over prevention of contaminating nucleic acids, the DNA is brought into contact with UNG (Uracil-DNA-Glycosylase). Thereby, the contaminating DNA containing uracil Is degraded while the DNA of the sample remains intact because after the inventive bisulfite treatment the DNA of the sample contains only uracil sulfonate. Thereafter the decontaminated DNA is heated under modest alkaline conditions (ph 8.0 or higher). This leads to a desulfonation of uracil sulfonate and enables the decontamination of subsequent sample. Contaminating DNA is in particular a problem in laboratories processing a huge number of sample such as but not limited to reference laboratories. Therefore the method of the invention is in particular valuable for such kind of laboratories.

The exemplary inventive method is further characterized in that it allows a highly sensitive and reliable detection of the methylation of the septin 9 gene. Inventive oligonucleotides and inventive oligonucleotide combinations were selected from the enormous number of possible oligonucleotides and oligonucleotide combinations which resemble parts of the sequence of the septin 9 gene or hybridize under stringent conditions to it. Particular embodiments of the inventive method are characterized by a doubled sensitivity. According to said embodiments, the methylation of septin 9 is analyzed by means of two reactions, each reaction specific for one strand of converted DNA (EP06090132). Correspondingly, particular oligonucleotide combinations are selected from the enormous number of possible oligonucleotide combinations which resemble parts of the sequence of the septin 9 gene or hybridize under stringent conditions to it.

The exemplary inventive method is further characterized in that the provided DNA is free of associated or linked proteins, peptides, amino acids, RNA, nucleotides or bases as well as interfering chemical reagents. According to the invention, this is based therein, that i) a DNA isolation method is selected which is characterized by a efficient removal of associated or linked proteins, peptides, amino acids, RNA, nucleotides or bases amongst the enormous number of possible DNA isolation methods; ii) a purification method for bisulfite treated DNA is selected which efficiently removes associated nucleotides or bases amongst the enormous number of possible devices; and iii) a method for discrimination between methylated and unmethylated cytosine is selected which minimizes further DNA fragmentation amongst the enormous number of discrimination methods. The removal of such components is of particular importance because the may sterically hinder the methylation analysis.

An exemplary particular preferred embodiment of the inventive method is further characterized by an increased recovery of low molecular weight DNA after DNA isolation, bisulfite treatment and purification of bisulfite treated DNA. This is achieved by an extended digestion with proteinase K, most preferably for 60 min, and only a single washing of the DNA binding beads in the DNA isolation step.

The exemplary inventive method is further characterized by low costs because it is based on the use of devices and solutions which are already available at low expenses. In addition, its suitability for being capable to be automated, for being capable to be standardized, for high throughput, as well as for low handling efforts also leads to a reduction in costs.

Taken together, because of the above explained advantages, the exemplary inventive method allows in particular the use of remote samples for methylation analysis in high throughput reference laboratories. In particular, said use is characterized in that it is reliable and reproducible. These are two necessary requirements for a medical test.

The exemplary inventive method makes also remote samples available for methylation based discovery of markers. In particular, it allows the identification of markers, characterized by a high sensitivity, a high specificity, or both.

Method of Aspects of the Invention.

The method of the invention is a method for providing DNA for methylation analysis. It comprises the following steps:
(a) isolating genomic DNA from a sample by means of SiMAG/FK-Silanol beads or beads of the chemagic Viral DNA/RNA Kit special; and
(b) subjecting the isolated DNA to a treatment wherein cytosine is converted to uracil sulfonate or another base having a different binding behavior than cytosine, while methylated cytosine remains unchanged.

According to a preferred embodiment, the treated DNA is purified by means of SiMAG/FK-Silanol beads or beads of the chemagic Viral DNA/RNA Kit special.

The method of the invention is also a method for providing DNA for methylation analysis that comprises the following steps
(a) subjecting genomic DNA to a treatment wherein cytosine is converted to uracil sulfonate or another base having a different binding behavior than cytosine, while methylated cytosine remains unchanged; and
(b) purifying the treated DNA by means of SiMAG/FK-Silanol beads or beads of the chemagic Viral DNA/RNA Kit special.

According to a preferred embodiment, the genomic DNA is isolated from a sample by means of SiMAG/FK-Silanol beads or beads of the chemagic Viral DNA/RNA Kit special.

According to a preferred embodiment, the SiMAG/FK-Silanol beads are the SiMAG/FK-Silanol beads of the company Chemicell GmbH (Germany, Article Number 1101-01 or 1101-05).

According to a preferred embodiment, the beads of the chemagic Viral DNA/RNA Kit special are beads of the chemagic Viral DNA/RNA Kit special of the company Chemagen Biopolymer-Technologie Aktiengesellschaft (Germany; Article Number 1002).

According to a preferred embodiment, DNA is provided for methylation analysis, wherein
(a) genomic DNA is isolated from a sample, in particular a remote sample, by means of SiMAG/FK-Silanol beads (Chemicell GmbH, Germany, Article Number 1101-01 or 1101-05) or beads of the chemagic Viral DNA/RNA Kit special (Chemagen Biopolymer-Technologie Aktiengesellschaft; Article Number 1002); and
(b) the isolated DNA is subjected to a treatment, wherein cytosine is converted to uracil sulfonate or another base having a different binding behavior than cytosine, while methylated cytosine remains unchanged.

Additionally, in a preferred embodiment, the treated DNA is purified by means of SiMAG/FK-Silanol beads (Chemicell GmbH, Germany, Article Number 1101-01 or 1101-05) or beads of the chemagic Viral DNA/RNA Kit special (Chemagen Biopolymer-Technologie Aktiengesellschaft; Article Number 1002).

According to a preferred embodiment, DNA is provided for methylation analysis, wherein
(a) genomic DNA is subjected to a treatment wherein cytosine is converted to uracil sulfonate or another base having a different binding behavior than cytosine, while methylated cytosine remains unchanged; and
(b) the treated DNA is purified by means of SiMAG/FK-Silanol beads (Chemicell GmbH, Germany, Article Number 1101-01 or 1101-05) or beads of the chemagic Viral DNA/RNA Kit special (Chemagen Biopolymer-Technologie Aktiengesellschaft; Article Number 1002).

Additionally, in a preferred embodiment, the genomic DNA is isolated from a sample by means of SiMAG/FK-Silanol beads (Chemicell GmbH, Germany, Article Number 1101-01 or 1101-05) or beads of the chemagic Viral DNA/RNA Kit special in a previous step (Chemagen Biopolymer-Technologle Aktiengesellschaft; Article Number 1002).

According to a preferred embodiment, the said sample is a remote sample. According to a preferred embodiment, the remote sample is at least one selected from the group comprising: blood sample, plasma sample, serum sample, body fluid sample, saliva sample, urine sample, semen sample, sample of the fluid from the pleural cavity, sample from the fluid from the peritoneal cavity, sample of the cerebrospinal fluid, smear from a epithelial surface, sputum sample, stool sample, ejaculate sample, tears sample, sweat sample, lymph fluid sample, bronchial lavage sample, pleural effusion sample, meningal fluid sample, glandular fluid sample, fine needle aspirates sample, nipple aspirates fluid sample, spinal fluid sample, conjunctival fluid sample, vaginal fluid sample, duodenal fluid sample, prancreatic juice sample, or bile sample.

According to an embodiment, the remote sample can be any kind of a sample. Preferably, the remote sample is a sample that is characterized in that it comprises at least one component which is mainly located distantly from the other components of the said sample. For example blood is not a remote sample with regard to a red blood cell, but it is a remote sample with regard to a DNA fragment which is derived from a tumor located in the lung.

According to a preferred embodiment, the isolation of genomic DNA comprises (i) the treatment of the said sample with proteinase K for 45-75 min, preferably for 55-65 min, and most preferably for 60 min; (ii) the use of magnetic beads of the chemagic Viral RNA/DNA kit (Chemagen Biopolymer-Technologie AG, Germany, Article number 1002); (iii) the use of Binding Buffer 2*3; (iv) an incubation for 60 min to allow the binding of DNA to the beads; and (v) only a single wash with 3 ml of Washing Buffer 3. According to a particular preferred embodiment, 4-6 ml of Lysis Buffer 1, preferably 5 ml, 4-10 µl poly-A RNA, preferably 7 µl, and 20-40 µl of Proteinase K solution, preferably 30 µl, are added to a sample. Optionally, in addition, antifoam is added. The reaction mixture is incubated at 50-62° C. for 5-20 min, preferably at 56° C. for 10 min. Thereafter, 50-200 µl, preferably 100 µl, of magnetic beads of the chemagic Viral RNA/DNA kit and 12-18 ml, preferably 15 ml, of Binding Buffer 2, 2*1, 2*2, 2*3, or 2*4 are added. Subsequently, beads are kept in suspension for at least about 5 min, preferably for about 10 min, or for about 45-75 min, preferably for 55-65 min, or most preferably for 60 min to allow the binding of DNA to the beads. Preferably the beads are kept in suspension at room temperature. Magnetic beads are separated by placing the reaction tube in a magnetic stand and discarding the plasma/lysis buffer mixture. Beads are washed threetimes, or twice with 1.5-4 ml, preferably 3 ml, of Wash Buffer 3, before they are resuspended in 0.5-2 ml, preferably 1 ml, of Wash Buffer 4. Alternatively, beads are washed only once with 1-2 ml, preferably 1.5 ml, of Wash Buffer 3. Beads are separated on a magnetic stand, the wash buffer is poured off and the beads are dried at 20-62° C., preferably at 56° C. After addition of 50-200 µl Elution Buffer 5, the suspension is incubated for at least 5 min at 50-70° C. Preferably, after addition of 100 µl Elution Buffer 5, the suspension is incubated for 15 min at 65° C. After separation of the beads, the elution buffer containing the genomic DNA is recovered (reagents are supplied by the chemagic Viral RNA/DNA kit; Binding Buffers 2*1, 2*2, 2*3, 2*4 are commercial variations of the binding buffer 2 which are all available from Chemagen Biopolymer-Technologie AG, Germany).

According to a preferred embodiment, for isolation of genomic DNA, 4-6 ml of the Lysis Buffer (120 g Guanidinium Isothiocyanate; 100 ml 0.1 mol/l Tris-HCl pH6.4 (subsequently); 22 ml 0.2 mol/l EDTA pH 8.0; 2.6 g Triton X-100), 50-200 µl of Proteinase K solution (provided by chemagic Viral RNA/DNA kit; Chemagen Biopolymer-Technologie AG, Germany, Article Number 1002) and 50-300 µl of SiMAG/FK-Silanol beads (Chemicell GmbH, Germany; Article number 1101-1 or 1101-5) are added to a sample. Preferably 5 ml of Lysis Buffer, 100 µl of Proteinase K solution and 100 µl of SiMAG/FK-Silanol beads are added to a sample. The reaction mixture is incubated at 45-65° C. for at least 10 min, preferably at 56° C. for 20 min. Thereafter, the beads are washed with 0.5-3 ml, preferably with 1 ml, Wash Buffer 1 (120 g Guanidinium Isothiocyanate; 100 ml 0.1 mol/l Tris-HCl pH6.4; dilute with 100% Ethanol to 25% Ethanol) and twice with 0.5-3 ml, preferably with 1 ml, Wash Buffer 2 (50% EtOH). Finally, the beads are dried for example but not limited to at 45-62° C. for at least 3 min, preferably at 56° C. for 5 min, before they are resuspended in 25-200 µl, preferably 50 µl, of Elution Buffer or water. The mixture is incubated at 37-70° C. for at least 5 min, preferably at 65° C. for 15 min. After separation of the beads, the DNA in Elution Buffer is obtained. The elution step may be repeated a second time and combined with the first elution volume.

According to a preferred embodiment, the isolation of genomic DNA comprises the treatment with one or more restriction enzymes, one or more proteins specifically binding to methylated DNA, one or more proteins specifically binding to unmethylated DNA, or combinations thereof. Suitable restriction enzymes are enzymes which digest DNA methylation-dependently or irrespective of its methylation. Enzymes that digest DNA methylation-dependently are enzymes which digest DNA only in case its recognition site is methylated, or in case its recognition site is unmethylated. Enzymes that cut only DNA in case its recognition site is methylated are for example but not limited to McrBC, Bisl, Glal or combinations thereof. Enzymes that cut only DNA in case its recognition site is unmethylated are for example but not limited to BstUl, Bshl2361, Accll, BstFNl, Mvnl, Hpall (Hapll), Hhal, Acil, Smal, HinP1l, HpyCH4IV, Eagl or combinations thereof. Enzymes that digest DNA irrespective of its methylation are enzymes which comprise no CpG dinucleotide within its recognition site. For example but not limited to these enzymes are one or more of the group consisting of Msel, Bfal, Csp6l, Tru1l, Tvu1l, Tru9l, Tvu9l, Mael and Xspl. The said enzymes, methylation-dependent and methylation-independent, are applied in order to reduce the complexity of the isolated DNA. The said enzymes, methylation-dependent and methylation-independent are also applied in order to enrich methylated DNA, unmethylated DNA, or both. Any combination of enzymes digesting methylated DNA, unmethylated DNA or digesting DNA methylation independently is applicable according to the invention.

According to a preferred embodiment, the isolation of genomic DNA comprises a protein specifically binding to methylated DNA and/or a protein specifically binding to unmethylated DNA. Suitable proteins are known to those skilled in the art. For example but not limited to it such proteins are MeCP2, MBD1, MBD2, MBD4 and Kaiso, or any domain thereof or methylation-specific antibodies, e.g. anti-5-methylcytosine anti-bodies (binding to methylated DNA). For example but not limited to it, proteins binding to unmethylated DNA are the CXXC-3 domain of the MBD1 protein. Proteins that bind methylated DNA, proteins that bind unmethylated DNA, or combinations thereof are in particular useful for the enrichment of methylated DNA, unmethylated DNA, or both. Further, a chromatin immunoprecipitation (ChIP) may be performed for enrichment. However, even further substances may be used for enrichment, for instance triplex-forming PNA or DNA oligomers. A more detailed disclosure of suitable DNA enrichment and DNA complexity reduction can be gathered from for example but not limited to WO 2006/088978.

According to a preferred embodiment, the isolation of genomic DNA comprises the treatment with one or more restriction enzymes, a protein specifically binding to methylated DNA, a protein specifically binding to unmethylated DNA, or combinations thereof.

According to a preferred embodiment, the treatment of DNA is a treatment with a cytidin deaminases. These enzymes convert unmethylated cytidin faster than methylated cytidin (Brandsteitter et al. Activation-induced cytidine deaminase deaminates deoxycytidine on single-stranded DNA but requires the action of RNase. Proc Natl Acad Sci USA. 2003 Apr. 1; 100(7):4102-7).

According to a preferred embodiment, the treatment of DNA is a treatment with a bisulfite reagent or solution. Suitable bisulfite reagents or solutions are known to those skilled in the art. The bisulfite conversion may take place both in solution as well as also on DNA bound to a solid phase. Preferably sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine conversion. When bisulfite concentration is discussed below, this refers to the concentration of hydrogen sulfite and sulfite anions in the reaction solution. For the method according to the invention, concentration ranges of 0.1 to 6 mol/l are possible. Particularly preferred is a concentration range of 1 to 6 mol/l, and most particularly preferred, 2-4 mol/l.

According to a preferred embodiment, a bisulfite treatment is essentially carried out as described in WO05/038051 or in WO 2006/113770. According to this, in one embodiment DNA is reacted with a bisulfite reagent, characterized in that said reaction is carried out in the presence of n-alkylene glycol compounds, preferably in the presence of their dialkyl ethers, and particularly preferred in the presence of diethylene glycol dimethyl ether (DME).

The n-alkylene glycol compounds according to the invention can be utilized in a different concentration range. DME is preferably used in concentrations between 1-35% (vol/vol), more preferably between 5 and 25%, and most preferably in a concentration of 10% DME.

According to a preferred embodiment, the treatment with a bisulfite comprises a radical scavenger. Preferably the radical scavenger is chromane derivatives, e.g., 6-hydroxy-2,5,7,8,-tetramethylchromane 2-carboxylic acid (also known as: Trolox-C™) or derivative thereof. In a preferred embodiment the concentration for 6-hydroxy-2,5,7,8,-tetramethylchromane 2-carboxylic acid is between 35 and 50 mmol/l. Preferably the radical scavenger is gallic acid (3,4,5-trihydroxy benzoic acid) or a derivative thereof. In a preferred embodiment the concentration for gallic acid and gallic acid derivatives is between 50 and 60 mmol/l.

According to a preferred embodiment, the treatment with a bisulfite comprises a radical scavenger, in particular 6-hydroxy-2,5,7,8,-tetramethylchromane 2-carboxylic acid or gallic acid, and an organic solvent, in particular DME.

Further scavengers suitable for use according to the invention are listed in the patent application WO 01/98528.

The bisulfite conversion can be conducted in a wide temperature range from 0 to 95° C. However, as at higher temperatures the rates of both the conversion and decomposition of the DNA increase, in a preferred embodiment the reaction temperature lies between 0-80° C., preferably between 30-75° C. Particularly preferred is a range between 35-65° C.; most particularly preferred between 45-55° C. The optimal reaction time of the bisulfite treatment depends on the reaction temperature. The reaction time normally amounts to between 1 and 18 hours (see: Grunau et al. 2001, Nucleic Acids Res. 2001, 29(13):E65-5). The reaction time is ordinarily 4-10 hours for a reaction temperature in the range of 45-55° C. In a most particular preferred embodiment, the reaction temperature is 50° C. and the reaction time 7 hours. (we use 50 C 7 h!)

In a particularly preferred embodiment of the method according to the invention, the bisulfite conversion is conducted at mild reaction temperatures, wherein the reaction temperature is then clearly increased for a short time at least once'during the course of the conversion. In this way, the effectiveness of the bisulfite conversion can be surprisingly clearly be increased. The temperature increases of short duration are named "thermospikes". The "standard" reaction temperature outside the thermospikes is denoted as the basic reaction temperature. The basic reaction temperature amounts to between 0 and 80° C., preferably between 30-75° C., more preferably between 35-65° C., most preferably between 45-55° C., as described above. Most particularly, preferred is a reaction temperature of 50° C.

The reaction temperature during a thermospike is increased to over 85° C. by at least one thermospike. The optimal number of thermospikes is a function of the basic reaction temperature. The higher the optimal number of thermospikes is, the lower is the basic reaction temperature. At least one thermospike is necessary in each case. And, on the other hand, in principle, any number of thermospikes is conceivable. Of course, it must be considered that with a large number of temperature increases, the decomposition rate of the DNA also increases, and an optimal conversion is no longer assured. The preferred number of thermospikes is thus between 1 and 10 thermospikes each time, depending on the basic reaction temperature. A number of two to 5 thermospikes is thus particularly preferred. The thermospikes increase the reaction temperature preferably to 85 to 100° C., particularly preferably to 90-100° C., and most preferably to 94° C.-100° C.

The duration in time of the thermospikes also depends on the volume of the reaction batch. Preferably, it is assured that the temperature is increased uniformly throughout the total reaction solution. In a particularly preferred embodiment, for a 320 µl reaction batch when using a thermocycler, a duration of 5 min at 99° C. is preferred. From this, a person skilled in the art will easily be able to determine suitable durations of thermospikes in relation to a variety of reaction volumes. The above-described thermospikes lead to a significantly better conversion rates in the bisulfite conversion reaction.

According to the invention, the said treatment of DNA with bisulfite is particularly preferred because it has several important advantages in comparison to other known methods or kits of the state of the art. These advantages are: i) higher yield of converted DNA; ii) a nearly complete conversion of unmethylated cytosine while methylated cytosine remain unchanged; and iii) almost no further fragmentation of DNA. These advantages are based in milder reaction conditions because of i) a thermal denaturation of DNA; ii) a comparably lower bisulfite concentration; iii) a slightly more alkaline pH; and iv) the use of a more efficient and more effective radical scavengers.

In a preferred embodiment, the method of the invention is a method, wherein treating DNA with a bisulfite reagent comprises:

mixing of about 10 to about 250 µl of a solution comprising DNA with about 45 to about 750 µl of bisulfite solution, the bisulfite solution having a pH in the range of about 5.45 to about 5.50 comprising about 4-5 mol/l hydrogensulfite, preferably about 4.83 to about 4.93 mol/l hydrogensulfite;

adding about 5 to about 500 µl of an organic radical scavenger solution, the organic radical scavenger solution comprising an organic solvent and about 10 to about 750 mmol/l of 6-hydroxy-2,5,7,8-tetramethyl-chroman-2-carboxylic acid; and applying a temperature protocol for about 2 to about 18 h, wherein the reaction is conducted in a temperature range of about 0 to about 80° C. with about 2 to about 5 additional temperature increases, in each case for about 0.5 to about 10 min, to a temperature of about 85 to about 100° C. including an initial temperature increase to a temperature of about 85 to about 100° C.

According to a preferred embodiment, the treatment comprising the use of a bisulfite reagent comprises further:

mixing of about 10 to about 250 µl of a solution comprising DNA with about 45 to about 750 µl of bisulfite solution, the bisulfite solution having a pH in the range of about 5.45 to about 5.50 comprising about 4-5 mol/l hydrogensulfite, preferably about 4.83 to about 4.93 mol/l hydrogensulfite;

adding about 5 to about 500 µl of an organic radical scavenger solution, the organic radical scavenger solution comprising an organic solvent and about 10 to about 750 mmol/l of 6-hydroxy-2,5,7,8-tetramethyl-chroman-2-carboxylic acid; and applying a temperature protocol for about 2 to about 18 h, wherein the reaction is conducted in a temperature range of about 0 to about 80° C. with about 2 to about 5 additional temperature increases, in each case for about 0.5 to about 10 min, to a temperature of about 85 to about 100° C. including an initial temperature increase to a temperature of about 85 to about 100° C.

In a particularly preferred embodiment, the method of the invention is a method wherein treating DNA with a bisulfite reagent comprises:

mixing of about 50 to about 150 µl of a solution containing the DNA with about 95 to about 285 µl of the bisulfite solution;

adding about 15 to about 45 µl of DME solution, the DME solution comprising about 500 mmol/l of 6-hydroxy-2,5,7,8-tetramethyl-chroman-2-carboxylic acid dissolved in diethylene-glycoldimethylether; and applying a temperature protocol for about 3 to about 16 h, wherein the reaction is conducted in a temperature range of about 45 to about 55° C. with about 2 to about 5 additional temperature increases, in each case for about 3 to about 5 min, to a temperature of about 94 to about 100° C. including an initial temperature increase to a temperature of about 94 to about 100° C.

According to a particular preferred embodiment, the bisulfite treatment of DNA comprises:

mixing of about 50 to about 150 µl of a solution containing the DNA with about 95 to about 285 µl of the bisulfite solution;

adding about 15 to about 45 µl of DME solution, the DME solution comprising about 500 mmol/l of 6-hydroxy-2,5,7,8-tetramethyl-chroman-2-carboxylic acid dissolved in diethylene-glycoldimethylether; and applying a temperature protocol for about 3 to about 16 h, wherein the reaction is conducted in a temperature range of about 45 to about 55° C. with about 2 to about 5 additional temperature increases, in each case for about 3 to about 5 min, to a temperature of about 94 to about 100° C. including an initial temperature increase to a temperature of about 94 to about 100° C.

Said treatment with a bisulfite leads to a sulfonation, a deamination, or both of unmethylated cytosine. Deamination is a spontaneous process in an aqueous solution and leads to sulfonated uracil (uracil sulfonate) comprising DNA. No desulfonation occurs yet.

According to a preferred embodiment, uracil sulfonate is desulfonated to uracil by heating.

According to a preferred embodiment, bisulfite treated DNA is purified by means of Si-MAG/FK-Silanol beads (Chemicell GmbH, Germany, Article Number 1101-01 or 1101-05) or beads of the chemagic Kit special (Chemagen Biopolymer-Technologie Aktiengesellschaft; Article Number 1002). Purification is performed according to the manufacturer's instructions. However and therewith particularly preferred, the washing step is intensified. Preferably, the corresponding one or more washing buffers are each applied repeatedly, preferably two times, wherein up to 600 µl of each washing buffer is applicable (combined volume of all washings steps performed with the same washing buffer).

According to a preferred embodiment, the DNA after bisulfite treatment and if the case may be after purification by means of SiMAG/FK-Silanol beads (Chemicell GmbH, Germany, Article Number 1101-01 or 1101-05) or beads of the chemagic Viral DNA/RNA Kit special in a previous step (Chemagen Biopolymer-Technologie Aktiengesellschaft; Article Number 1002), is directly subjected to amplification. Thereby uracil sulfonate becomes desulfonated in the initial heating step. If the case may be, the initial heating step last for 5 min, 10 min, 15 min, 20 min, 30 min, 45 min or 60 min in order to allow a complete desulfonation of the uracil sulfonate containing DNA. Preferably, the temperature of the initial heating step lies in the range of 80-100° C. and most preferably in the range of 90-95° C. The desulfonation by heating treatment is further characterized in that it is performed in low alkaline conditions, preferably in the range of pH 7.5-10, most preferably in the range of pH 8.0-9.5.

According to a preferred embodiment, the genomic DNA is cleared from contaminating DNA. For this, the DNA comprising sulfonated uracil is brought Into contact and incubated with an enzyme which specifically degrades non-sulfonated uracil containing nucleic acids. Such an enzyme is for example Uracil-DNA-Glycosylase (UNG).

In a particularly preferred embodiment for providing a decontaminated template DNA for polymerase based amplification reactions, the sulfonated and/or deaminated template DNA are mixed with an UNG activity and components required for a polymerase mediated amplification reaction or an amplification based detection assay. After degradation of non-sulfonated uracil containing nucleic acids by use of UNG, the UNG activity is terminated and the template DNA is desulfonated by increased temperature. Subsequently the template DNA is ready to be amplified.

Preferably, degradation, termination, desulfonation and amplification occur in a single tube during a polymerase based amplification reaction and/or an amplification based assay. Preferably such an amplification is performed in the presence of dUTP instead of dTTP.

Preferably, sulfonated and partially or completely deaminated DNA after bisulfite treatment is subjected directly to a polymerase based amplification reaction and/or an amplification based assay without any prior desulfonation. The desulfonation occurs during the initial temperature increase of the amplification reaction.

According to a preferred embodiment, DNA provided according to the invention is analyzed. Preferably, the methylation of the provided DNA is analyzed, in particular a methylation status or a methylation pattern. Thereby the methylation analysis comprises at least one selected from the group consisting of amplification method, PCR method, isothermal amplification method, NASBA method, LCR method, methylation specific amplification method, MSP (Methylation Specific PCR) method, nested MSP method, HeavyMethyl™ method, detection method, methylation specific detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

According to a preferred embodiment, the provided nucleic acid molecule is analyzed with regard to it methylation. Suitable methods are for example, but not limited to, amplification method, PCR method, isothermal amplification method, NASBA method, LCR method, methylation specific amplification method, MSP (Methylation Specific PCR) method, nested MSP method, HeavyMethyl™ method, detection method, methylation specific, detection method, bisulfite sequencing method, detection by means of DNA-arrays, detection by means of oligonucleotide microarrays, detection by means of CpG-island-microarrays, detection by means of restriction enzymes, simultaneous methylation specific amplification and detection method, COBRA method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method or combinations thereof. Said methods are described in detail below.

According to an embodiment, the amplification method can be any kind of amplification method. A person skilled in the art is in knowledge of suitable amplification methods. According to a preferred embodiment, the amplification method is a PCR method. A person skilled in the art knows suitable PCR methods which can be used according to the invention. According to a preferred embodiment, the amplification method is a isothermal amplification. Suitable amplification methods for use according to the invention are well known in the art. Such a method can be for example but not limited to it the Primer Extension method. According to a preferred embodiment, the amplification method is a NASBA method. NASBA methods are RNA-DNA based amplification methods which comprise the use of a Reverse Transcriptase, a RNA polymerase and a RNase. A person skilled in the art is aware of NASBA methods which can be used according to the invention. According to a preferred embodiment, the amplification method is a Ligase Chain Reaction method. In general, these are amplification methods which are based on the use of a ligase. A person skilled in the art knows suitable LCR which can be used according to the invention.

According to a preferred embodiment, the amplification method is a methylation specific amplification. Suitable methylation specific amplification methods are known to those skilled in the art. According to a preferred embodiment, the methylation specific amplification method is the Methylation Specific PCR (MSP) method. The MSP method allows the assessing of the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP primer pairs contain at least one primer, which hybridizes to a bisulfite treated CpG dinucleotide. Therefore, the sequence of said primers comprises at least one CpG dinucleotide. MSP primers specific for non-methylated DNA contain a "T" at the 3' position of the C position in the CpG. Preferably, therefore, the base sequence of said primers is required to comprise a sequence having a length of at least 9 nucleotides which hybridizes to the bisulfite converted nucleic acid sequence, wherein the base sequence of said oligomers comprises at least one CpG dinucleotide. MSP requires only small quantities of DNA and is sensitive to 0.1% methylated alleles of a given CpG island locus. Bisulfite treatments and amplification method described herein may be used in combination with this detection method.

According to a preferred embodiment, the amplification is a nested MSP method. The nested MSP method is essentially carried out as described in WO 02/18649 and US 20040038245. This MSP method considers the apparent conflict of requiring high specificity of the MSP primer to sufficiently differentiate between CG and TG positions and of allowing a mismatch in order to create a unique restriction site.

It comprises the expanding of copy numbers of the genetic region of interest. Therefore a polymerase chain reaction is used to amplify a portion of said region wherein the methylation of interest resides. Thereby an amplification product is generated. An aliquot of said product is then used in a second, methylation-specific, polymerase chain reaction to detect the presence of methylation. In other words a non methylation specific PCR is performed prior to the methylation specific PCR.

According to a particularly preferred embodiment, the amplification method is the HeavyMethyl™ method. The HeavyMethyl™ method is essentially carried out as described in WO 02/072880 and Cottrell S E et al. Nucleic Acids Res. 2004 January 13; 32(1):e10. This method comprises the use of blocking probe oligonucleotides which may be hybridized to the bisulfite treated template nucleic acid concurrently with the PCR primers. Preferably, the blocking oligonucleotides are characterized in that their base sequence comprises a sequence having a length of at least 9 nucleotides which hybridizes to the chemically treated nucleic acid sequence. Thereby the base sequence of said blocker oligonucleotides comprises at least one CpG, TpG or CpA dinucleotide. The amplification of the template nucleic acid is suppressed in case the complementary sequence of the blocking probe is present in the template. In such a case the amplification is terminated at the 5' position of the blocking probe. The blocking probe may be designed to hybridize to the bisulfite treated nucleic acid in a methylation status specific manner. For example, methylated nucleic acids within a population of unmethylated nucleic acids can be detected by suppressing the amplification of nucleic acids which are unmethylated at a position in question. Therefore a blocking probe would comprise a 'CpA' or 'TpA' at the position in question, as opposed to a 'CpG' if the suppression of amplification of methylated nucleic acids is desired. The use of blocker oligonucleotides requires for an efficient disruption of polymerase-mediated amplification that the blocker oligonucleotides can not be elongated by the polymerase. According to the HeavyMethyl™ method, this is achieved through the use of blockers that are 3'-deoxyoligonucleotides, or oligonucleotides derivatized at the 3' position with other than a "free" hydroxyl group. For example, but not limited to it, 3'-O-acetyl oligonucleotides are representative of a preferred class of blocker molecules.

Additionally, polymerase-mediated degradation of the blocker oligonucleotides should be precluded. Preferably, such preclusion comprises either i) the use of a polymerase lacking 5'-3' exonuclease activity, or ii) the use of modified blocker oligonucleotides. These modified blocker oligonucleotides are characterized in having, for example but not limited to, thioate bridges at the 5'-terminii. This renders the blocker molecule nuclease-resistant. Particular applications may not require such 5' modifications of the blocker oligonucleotide. For example, degradation of the blocker oligonucleotide will be substantially precluded if the blocker- and primer-binding sites overlap. Thereby the binding of the primer is precluded (e.g., in case of excess blocker oligonucleotide). Therefore the polymerase can not bind on the primer and elongated it. Because no polymerase is extending the primer, the blocking oligonucleotide will not be degraded. A particularly preferred embodiment of the HeavyMethyl™ method, for purposes of the present invention and as implemented herein, comprises the use of peptide nucleic acid (PNA) oligomers as blocking oligonucleotides. Such PNA blocker oligomers are ideally suited because they are neither degraded nor extended by the polymerase.

According to an embodiment, the detection method can be any kind of detection method. A person skilled in the art is in knowledge of suitable detection methods. Preferably, a detection method can be any kind of detection method which comprises the use of a fluorescent dye, a non-fluorescent dye, a mass label, a separation by size, or a separation by weight. For example, but not limited to it, the detection method is a separation by size in an agarose gel followed by a staining of DNA by means of a fluorescent dye. According to a preferred embodiment, the detection method is a methylation specific detection. A person skilled in the art knows suitable methylation specific detection methods. According to a preferred embodiment, the methylation specific detection method is a bisulfite sequencing method. The bisulfite sequencing method is essentially carried out as described in Frommer et al. Proc. Natl. Acad. Sci. USA 89:1827-1831, 1992. The bisulfite sequencing method is a method wherein the sequencing of a previously amplified fragment of the bisulfite treated genomic DNA is carried out. As the bisulfite treated DNA is amplified before sequencing, an amplification method as described herein may be used in combination with this detection method. It is further especially preferred that the results of a bisulfite sequencing are essentially analyzed as described in EP 02090203.7. In brief, according to this method the degree of methylation of a cytosine is determined by means of an electropherogram of one or more bases. Thereby the area underneath the electropherogram of a detected base is calculated. The degree of methylation is then deduced by comparison this value for a cytosine position to be analyzed with the value obtained for an unmethylated cytosine. For better results, the determination and the consideration of the conversion rate of cytosine to uracil of the bisulfite treatment and/or a standardization of electropherogram signals is favorable.

According to a preferred embodiment, the detection method is a method of detection by means of a DNA-array. A person skilled in the art knows a lot of suitable DNA-arrays. Preferably, a DNA array comprises DNA molecules which are bound to or elsewise associated with a solid phase. The array can be characterized, for example but not limited to it, in that the DNA molecules are arranged on the solid phase in the form of a rectangular or hexagonal lattice. Thereby the solid phase is at least one phase selected from the group comprising: silicon, glass, polystyrene, aluminum, steel, iron, copper, nickel, silver, gold, nitrocellulose, or plastics such as but not limited to it nylon. But also combinations of the said materials are thinkable. For detection, the DNA hybridized on the array is labeled, preferably with a fluorescent dye. Such labelling is for example, but not limited to it, the simple attachment of Cy3 and Cy5 dyes to the 5'-OH of the DNA fragment. The detection of the fluorescence of the hybridized DNA may be carried out, for example, but not limited to it, via a confocal microscope.

According to a particular preferred embodiment, the detection method is a method of detection by means of a oligonucleotide microarray. An overview of the prior art in oligomer array manufacturing can for example but not limited to be gathered from a special edition of Nature Genetics (Nature Genetics Supplement, Volume 21, January 1999, and from the literature cited therein).

According to a particular preferred embodiment, the detection method is a method of detection by means of a CpG-island-microarray. Thereby the immobilized or associated DNA of the array comprises sequences which were derived from CpG islands.

According to a particular preferred embodiment, the detection method is a method of detection by means of a DNA-array as essentially described in WO 99/28498, WO 01/38565, or in WO 02/18632.

According to a preferred embodiment, the detection method is a method of detection by means of restriction enzymes. A person skilled in the art is in knowledge of suitable methods.

According to a preferred embodiment, the methylation specific amplification and the detection are carried out simultaneously. Suitable methods are known to those skilled in the art. According to a particular preferred embodiment, the method for simultaneous methylation specific amplification and detection is the COBRA method. The COBRA method is a quantitative methylation method useful for determining DNA methylation levels at specific gene loci in small amounts of genomic DNA (Xiong & Laird, Nucleic Acids Res. 25:2532-2534, 1997). According to the COBRA method, restriction enzyme digestion is used to reveal methylation-dependent sequence differences in PCR products of bisulfite-treated DNA. Methylation-dependent sequence differences are first introduced into the genomic DNA by bisulfite treatment. PCR amplification of the bisulfite converted DNA is then performed using methylation unspecific primers followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. Additionally, restriction enzyme digestion of PCR products amplified from bisulfite-converted DNA is also used, in the method described by Sadri & Hornsby (Nucl. Acids Res. 24:5058-5059, 1996). Bisulfite treatments and amplification methods described herein may be used in combination with this detection method.

According to a particular preferred embodiment, the method for simultaneous methylation specific amplification and detection is a real-time PCR method. A person skilled in the art knows suitable real-time PCR methods. According to a particular preferred embodiment, the real-time PCR method is a HeavyMethyl™ method. The HeavyMethyl™ method is thereby performed as described above by means of a real-time PCR machine.

According to a particular preferred embodiment, the real-time PCR method is a MethyLight™ method. The MethyLight™ method is a high-throughput quantitative methylation method that utilizes fluorescence-based real-time PCR (TaqMan™) technology that requires no further manipulations after the PCR step (Eads et al., Cancer Res. 59:2302-2306, 1999). Briefly, the MethyLight™ process begins with a mixed sample of genomic DNA that is converted, in a bisulfite reaction, to a mixed pool of methylation-dependent sequence differences according to standard procedures. Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight™ method may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique also named MSP MethyLight™ method), or with oligonucleotides covering potential methylation sites.

The MethyLight™ process can be used with a "TaqMan®" probe in the amplification process. For example, double-stranded genomic DNA is treated with bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Variations on the TaqMan® detection technology that are also suitable include the use of dual-probe technology (LightCycler™), fluorescent amplification primers (Sunrise™ technology), Molecular Beacon Probes (Tyagi S., and Kramer F. R., Nature Biotechnology 14, 303-308, 1996), Scorpion primers (Whitcombe et al., Nature and Biotechnology, 17, 804-807, 1999), or LNA (Locked Nucleid Acid) Double-Dye Oligonucleotide probes (Exiqon A/S). All of these techniques may be adapted in a manner suitable for use with bisulfite treated DNA, and moreover for methylation analysis within CpG dinucleotides.

Bisulfite treatments and amplification methods described herein may be used in combination with the MethyLight™ method or its variants.

According to a particular preferred embodiment, the real-time PCR method is the MethyLight™ ALGO™ method. The MethyLight™ ALGO™ method is an improved method of the MethyLight™ method as essentially described in EP 04090255.3. According to this improved method, the degree of methylation is calculated from the signal intensities of probes using different algorithms.

According to a particular preferred embodiment, the real-time PCR method is the QM (quantitative methylation) assay. This assay is a methylation unspecific and therefore unbiased real-time PCR amplification. It is accompanied by the use of two methylation specific probes (MethyLight™) one for the methylated amplificate and a second for the unmethylated amplificate. In this way, two signals are generated which can be used a) to determine the ratio of methylated (CG) to unmethylated (TG) nucleic acids, and at the same time b) to determine the absolute amount of methylated nucleic acids. For the later, a calibration of the assay is necessary with a known amount of control DNA.

According to preferred embodiment, the method for simultaneous methylation specific amplification and detection is a Headloop PCR method. The Headloop PCR method is a suppression PCR method. It essentially carried out as described in Rand K. N., et al., Nucleic Acid Research, 33(14), e127. It is a PCR method for distinguishing related sequences in which the selectivity of amplification is dependent from the amplicon's sequence. A 5' extension is included in one (or both) primer(s) that corresponds to sequences within one of the related amplicons. After copying and incorporation into the amplificate this sequence is then able to loop back, anneal to the internal sequences and prime to form a hairpin structure. This structure prevents then further amplification. Thus, amplification of sequences containing a perfect match to the 5' extension is suppressed while amplification of sequences containing mismatches or lacking the sequence is unaffected.

According to a particular preferred embodiment, the method for simultaneous methylation specific amplification and detection is a combination of the Headloop PCR method and the MethyLight™ method, also named Headloop MethyLight™ method.

According to preferred embodiment, the method for simultaneous methylation specific amplification and detection is a Scorpion™ method. This method was first described by Whitcombe et al.: Detection of PCR products using self-probing amplicons and fluorescence. Nat Biotechnol. 1999; 17(8):804-7; Thelwell et al.: Mode of action and application of Scorpion™ primers to mutation detection. Nucleic Acids Res. 2000 October 1; 28(19):3752-61; U.S. Pat. No. 6,326,145; U.S. Pat. No. 6,365,729; US 20030087240 A1). Several embodiments of this method are known to those skilled in the art. All of this methods have the intramolecular probing in common. According to the so-called Hairloop variant, Scorpion™ primers posses a specific probe sequence at their 5' end. This sequence is present in a hairloop like configuration. A fluorescent dye and a quencher are located in spatial proximity at the end of the probing sequence. After denaturation subsequent to an amplification cycle, the probe hybridizes intramolecularly onto the elongated primer sequence of the same strand. Thereby the hairloop is opened, the dye and the quencher are separated and thus the dye's signal can be detected.

Other Scorpion™ method variants are for example the Duplex variant (Salinas et al.: Duplex Scorpion™ primers in SNP analysis and FRET applications. Nucleic Acids Res. 2001 Oct. 15; 29(20):E96), or the variants as described in U.S. Pat. No. 6,326,145 and US 20030087240).

According to a particular preferred embodiment, the Scorpion™ method is a method as essentially described in WO 05/024056.

According to a particular preferred embodiment, the method for simultaneous methylatlon specific amplification and detection is a combination of the HeavyMethyl™ method and the Scorpion™ method, also named HeavyMethyl™ Scorpion™ method.

According to a particular preferred embodiment, the method for simultaneous methylation specific amplification and detection is a combination of the HeavyMethyl™ method and the MethyLight™ method, also named HeavyMethyl™ MethyLight™ method.

According to a particular preferred embodiment, the method for simultaneous methylation specific amplification and detection is a combination of the MSP method and the Scorpion™ method, also named MSP Scorpion™ method.

According to a particular preferred embodiment, the method for simultaneous methylation specific amplification and detection is a combination of the Headloop method and the Scorpion™ method, also named Headloop Scorpion™ method.

According to a preferred embodiment, the method for simultaneous methylation specific amplification and detection is a method of methylation specific primer extension. A person skilled in the art knows several methods which can be used according to the invention.

According to a particular preferred embodiment, the method of methylation specific primer extension is the Ms-SNuPE (methylation-sensitive Single Nucleotide Primer Extension) method. The Ms-SNuPE method is a method as essentially carried out as described in Gonzalgo et al., Nucleic Acids Research 25(12), 2529-2531, 1997 and U.S. Pat. No. 6,251,594. According to the Ms-SNuPE method, regions of interest are amplified by PCR from bisulfite treated DNA. After purification of the PCR products, primers are proximately hybridized in front of the position to be analyzed. The primer is then elongated by a single nucleotide either with labeled dCTP or with differently labeled dTTP. In case the cytosine in the original DNA was methylated, then dCTP will be incorporated because methylated cytosines remain unchanged during bisulfite treatment. In the other case, the cytosine in the original DNA was unmethylated, then dTTP will be incorporated because unmethylated cytosine is converted to uracil by bisulfite treatment and subsequent PCR will substitute uracil by thymine. By detection of the different labels, it can be distinguished if a cytosine of a CpG position was methylated or unmethylated. The MS-SNuPE method can also be performed in a quantitative manner.

According to a particular preferred embodiment, the method of methylation specific primer extension is a method as essentially described in WO 01/062960, WO 01/062064, or WO 01/62961. All of these methods can be performed in a quantitative manner. According to WO 01/062960, the primer to be extended hybridizes with its 3' terminus complete or only partially onto the positions of interest. A extension of at least one nucleotide occurs only if the primer hybridizes completely. WO 01/062064 discloses a method in which the primer to be extended hybridizes proximately adjacent or at a distance of up to ten bases to the position to be analyzed. The primer is then extended by at least a single nucleotide. The third method is described in WO 01/62961. According to this method, two set of oligonucleotides are hybridized to the amplified DNA after bisulfite treatment. The first type of oligonucleotide hybridizes 5' proximately adjacent or at a distance of up to 10 bases to the position to be analyzed. The second type of oligonucleotide hybridizes on the amplified DNA so that its 5' terminus hybridizes 3' proximately adjacent to said position to be analyzed. Through this, the two oligonucleotide are separated from each other by a gap of in the range of 1 to 10 nucleotides. The first type of oligonucleotide is then extended by means of a polymerase, wherein not more than the number of nucleotides lying between the two oligonucleotides are added. Thereby nucleotides are used which comprise differentially labeled dCTP and/or dTTP. The two oligonucleotides are then linked to each other by means of a ligase enzyme. In case the cytosine in the original DNA was methylated, then dCTP will be incorporated. In case the cytosine in the original DNA was unmethylated, then dTTP will be incorporated.

Of course other similar methods, which are further developed methods of the named methods or combinations thereof are also suitable for use according to the invention.

Aspects of the invention provides an improved method for the determination of the methylation of the Septin 9 gene by an amplification based assay. In particular, the presence or absence of CpG dinucleotides of the Septin 9 gene is determined by the inventive amplification bassed assays. For this, the methylation of one or more CpG dinucleotides of SEQ ID NO: 85 are determined in genomic DNA to be analyzed. Thus the methylation status of one CpG dinucleotide or a methylation pattern of two or more CpG dinucleotides is determined.

According to a preferred embodiment, genomic DNA may be extracted or otherwise isolated from a sample obtained from an individual. The genomic DNA is treated with one or more reagents to convert unmethylated cytosine bases to uracil or to another base that is detectably dissimilar to cytosine in terms of hybridization properties, while methylated cytosine remains unchanged. A preferred reagent is a bisulfite reagent. Other preferred reagents are cytidin deaminases. These enzymes convert unmethylated cytidin faster than methylated cytidin (Brandsteitter et al. Activation-induced cytidine deaminase deaminates deoxycytidine on single-stranded DNA but requires the action of RNase. Proc Natl Acad Sci USA. 2003 Apr. 1; 100(7):4102-7).

Thereafter the treated DNA is subject to an amplification reaction, wherein either the methylated sequence is preferably amplified over the unmethylated sequence, or wherein the unmethylated sequence is preferably amplified over the methylated sequence. Preferably the amplification is a PCR amplification.

A conclusion is made about methylation of the Septin 9 gene by detection of the amount of the preferably amplified sequence over time. Said detection is preferably carried out by means of real time analysis, particularly preferred real time PCR analysis, real time Taqman PCR analysis, or real time Lightcycler PCR analysis.

According to WO 2006/113466, methylation of the septin 9 gene is determined by means of the oligonucleotides SEQ ID NO: 92 and 93 used as primers, the oligonucleotide SEQ ID NO: 94 used as blocker, and the oligonucleotide SEQ ID NO: 31 used as probe. As an alternative to the oligonucleotide SEQ ID NO: 31, the oligonucleotide combination SEQ ID NO: 95 and 96 is used as probe combination.

In a particularly preferred embodiment, the same region of the septin 9 as analyzed by SEQ ID NO: 92-96 and 31 is analyzed by means the following oligonucleotides or oligonucleotides consisting essentially thereof.

The following oligonucleotide or an oligonucleotide consisting essentially thereof is used as a forward primer:

SEQ ID NO 92        GTAGTAGTTAGTTTAGTATTTATTTT

One of the following oligonucleotides or an oligonucleotide consisting essentially thereof is used as a reverse primer:

SEQ ID NO: 12        CCCACCAACCATCATAT

SEQ ID NO: 13        CCCACCAACCATCATATC

SEQ ID NO: 14        ACCCACCAACCATCATA

SEQ ID NO: 15        CTACCCACCAACCATCATAT

SEQ ID NO: 1        CCACCAACCATCATATC

Preferably, the amplification uses one of the following oligonucleotides as a blocker in order to preferably amplify the methylated DNA over the unmethylated DNA:

SEQ ID NO: 23   CATCATATCAAACCCCACAATCAACACACAAC-C3

SEQ ID NO: 24   CCATCATATCAAACCCCACAATCAACACACAA-INV

SEQ ID NO: 9    ACCATCATATCAAACCCCACAATCAACACACA-INV

SEQ ID NO: 97   CCATCATATCAAACCCCACAATCAACACACA-C3

SEQ ID NO: 91   CCATCATATCAAACCCCACAATCAACACAC-C3

SEQ ID NO: 98   ATCATATCAAACCCCACAATCAACACACAACT-C3

SEQ ID NO: 99   ACCATCATATCAAACCCCACAATCAACACAC-C3

-continued

SEQ ID NO: 100 AACCATCATATCAAACCCCACAATCAACACAC-C3

SEQ ID NO: 101 CCATCATATCAAACCCCACAATCAACACAC A-C3
(INV = inverted base linkage (3'-3');
C3 = propyl group)

Said oligonucleotides used as blockers may have the indicated modifications or any other known suitable modifications enabling the oligonucleotides to act as blockers.

According to the invention, amplified treated DNA can be detected by any means known in the art. In the simplest case, this is ethidium bromide or SYBR green. Preferably, amplified treated DNA is detected by means of one of the following oligonucleotides or of an oligonucleotides consisting essentially thereof, wherein said oligonucleotide is used as probe:

```
SEQ ID NO: 31    FAM-GAACCCCGCGATCAACGCG-BHQ1

SEQ ID NO: 32    FAM-TAGTTGCGCGTTGATCGCGG-BHQ1

SEQ ID NO: 33    FAM-TAGTTGCGCGTTGATCGC-BHQ1

SEQ ID NO: 34    FAM-CCGCGATCAACGCGC-BHQ1

SEQ ID NO: 35    FAM-CGCGTTGATCGCGGG-BHQ1

SEQ ID NO: 36    FAM-CGCGTTGATCGCGG-BHQ1

SEQ ID NO: 37    FAM-ACCCCGCGATCAACG-BHQ1

SEQ ID NO: 38    FAM-TGATCGCGGGGTTCG-BHQ1

SEQ ID NO: 39    FAM-AACCCCGCGATCAAC-BHQ1

SEQ ID NO: 40    FAM-GTTGATCGCGGGGTT-BHQ1

SEQ ID NO: 41    FAM-CCCCGCGATCAACG-BHQ1

SEQ ID NO: 4     FAM-GATCGCGGGGTTCGATA-BHQ1

SEQ ID NO: 42    FAM-CGATCAACGCGCAACTAA-BHQ1
(FAM is a fluorescent dye; BHQ1 =
BlackHoleQuencher 1 is quencher well known in the
art)
```

Said oligonucleotides used as probe may have the indicated labelling with dyes and quenchers or any other suitable labelling with dyes and quenchers. However the indicated dyes and quenchers are in particular preferred.

Preferably, amplified bisulfite treated DNA is detected by means of one of the following oligonucleotide combinations or an combination of oligonucleotides, wherein said oligonucleotide combination is used as probe combination:

```
SEQ ID NO: 102  GAAATGATTTTATTTAGTTGCGCG-FL

SEQ ID NO: 103  LCRed640-TGATCGCGGGGTTCG-PH

SEQ ID NO: 104  CCCGCGATCAACGCG-FL

SEQ ID NO: 105  LCred640-AACTAAATAAAATCATTTCGAACTTC
                G-PH
(FL and LCRred640 are fluorescent dyes well known
in the art.)
```

Said oligonucleotides used as probe combination may have the indicated labellings and modifications or any other suitable labellings or modifications. However the indicated labellings and modifications are in particular preferred.

In a particular preferred embodiment (assay A), genomic DNA of SEQ ID NO: 86 is analyzed, said sequence being part of the Septin 9 gene. After treatment of the genomic DNA with one or more reagents, preferably with a bisulfite reagent, the sense strand or the reverse complementary sequence thereof is further analyzed.

For this, one of the following oligonucleotides or an oligonucleotide consisting essentially thereof is used as a forward primer and hybridizes methylation-independently onto the bisulfite treated DNA:

```
SEQ ID NO: 6   GATT-dS-GTTGTTTATTAGTTATTATGT
               (-dS- = spacer)

SEQ ID NO: 48  ATT-dS-GTTGTTTATTAGTTATTATGT
               (-dS- = spacer)

SEQ ID NO: 62  ATT-NI-GTTGTTTATTAGTTATTATGT
               (-NI- = Nitroindole (universal base))

SEQ ID NO: 63  GATTGGTTGTTTATTAGTTATTATGT
               (general mismatch "G")

SEQ ID NO: 64  GATTAGTTGTTTATTAGTTATTATGT
               (general mismatch "A")
```

The methylation independent hybridization is achieved by means of a spacer, in particular a dSpacer, an universal base such as for example but not limited to nitroindole, or by means of a general mismatching nucleotide such as guanine, arginine, or any other artificial suitable nucleotide or base. The term "general" in this context means that the mismatching base forms neither with the methylated cytosine nor the converted unmethylated cytosine a Watson-Crick base pair. In particular, SEQ ID NO: 6 is preferred as forward primer.

One of the following oligonucleotides or an oligonucleotide consisting essentially thereof is used as a reverse primer:

```
SEQ ID NO: 65    CCCAACACCCACCTTC

SEQ ID NO: 66    CAACAACCAACCCAACA

SEQ ID NO: 67    CAACAACCAACCCAACAC

SEQ ID NO: 68    AACCCAACACCCACCT

SEQ ID NO: 69    CAACCCAACACCCACCT

SEQ ID NO: 70    CAACCCAACACCCACCT

SEQ ID NO: 71    AACCCAACACCCACCTT

SEQ ID NO: 72    ACCAACCCAACACCCACCTT
```

In particular SEQ ID NO: 65 is preferred as reverse primer.

Preferably, the amplification uses one of the following oligonucleotides or an oligonucleotide consisting essentially thereof, wherein said oligonucleotide is used as a blocker in order to preferably amplify the methylated DNA over the unmethylated DNA:

```
SEQ ID NO: 7   GTTATTATGTTGGATTTTGTGGTTAATGTGTAG-INV

SEQ ID NO: 73  GTTATTATGTTGGATTTTGTGGTTAATGTGT-INV

SEQ ID NO: 49  ATTATGTTGGATTTTGTGGTTAATGTGTAGTTG-INV

SEQ ID NO: 74  TATTATGTTGGATTTTGTGGTTAATGTGTAGTTGG-
               INV

SEQ ID NO: 75  GTTATTATGTTGGATTTTGTGGTTAATGTGTAG-ACR

SEQ ID NO: 76  ACR-GTTATTATGTTGGATTTTGTGGTTAATGTGTA
               G-INV
```

-continued

```
SEQ ID NO: 7   GTTATTATGTTGGATTTTGTGGTTAATGTGTAG-C3

SEQ ID NO: 55  ATTAGTTATTATGTTGGATTTTGTGGTTAATGTGTA
               G-C3

SEQ ID NO: 56  AGTTATTATGTTGGATTTTGTGGTTAATGTGTAGTT
               G-C3

SEQ ID NO: 57  TTATGTTGGATTTTGTGGTTAATGTGTAGTTGG-C3

SEQ ID NO: 50  ATTATGTTGGATTTTGTGGTTAATGTGTAGTTG-C3
(ACR = acridine; INV = inverted base linkage
(3'-3'); C3 = propyl group)
```

Said oligonucleotides used as blockers may have the indicated modifications or any other suitable modifications enabling the oligonucleotides to act as blockers. However, the indicated modifications are in particular preferred.

In particular, SEQ ID NO: 7 is preferred as blocker. In particular, a C3 modification is preferred to an INV modification.

According to the invention, amplified treated DNA can be detected by any means known in the art. In the simplest case, this is ethidium bromide or SYBR green. Preferably, amplified treated DNA is detected by means of one of the following oligonucleotides or an oligonucleotide consisting essentially thereof, wherein said oligonucleotide is used as probe:

```
SEQ ID NO: 83   HEX-CGGATTTCGCGGTTAACGC-BHQ1
SEQ ID NO: 84   HEX-AACTACGCGTTAACCGCGA-BHQ1
(HEX = fluorescent dye;
BHQ1 = BlackHoleQuencher 1)
```

Said oligonucleotides used as probes may have the indicated labelling with dyes and quenchers or any other suitable labelling with dyes and quenchers. However the indicated dyes and quenchers are in particular preferred.

Preferably, amplified bisulfite treated DNA is detected by means of one of the following oligonucleotide combinations or a combination of oligonucleotides consisting essentially thereof, wherein said oligonucleotide combination is used as probe combination:

```
SEQ ID NO: 77   TCGCGGTTAACGCGTAGTT-FL
SEQ ID NO: 78   red705-ATGGGATTATTTCGGATTTCGA-PH SEQ ID NO: 79   TTTCGCGGTTAACGCGTA-FL
SEQ ID NO: 80   Red705-TTGGATGGGATTATTTTGGATTT-PH SEQ ID NO: 81   ATCCGAAATAATCCCATCCAACTAC-FAM
SEQ ID NO: 82   TexRed-CGTTAACCGCGAAATCCG-C3
```

A fluorescent resonance energy transfer (FRET) reaction occurs between fluoresceine (FL) and red705 (alternative dyes are for example but not limited to red610 or red640) or between FAM and TexRed upon hybridization of the respective oligonucleotides onto the amplified DNA during the amplification reaction. (C3=propyl group; PH=3'OH phosphorylation)

Said oligonucleotides used as probe combination may have the indicated labellings and modifications or any other suitable labellings or modifications. However the indicated labellings or modifications are in particular preferred.

In particular, SEQ ID NO: 81 and 82 are preferred as probe combination.

In a particularly preferred embodiment (assay B), genomic DNA of SEQ ID NO: 87 is analyzed said sequence being part of the Septin 9 gene. After treatment of the genomic DNA with one or more reagents, preferably with a bisulfite reagent, the sense strand or the reverse complementary sequence thereof is further analyzed.

Therefore one of the following oligonucleotides or an oligonucleotide consisting essentially thereof is used as a forward primer and hybridizes methylation-independently onto the bisulfite treated DNA:

```
SEQ ID NO: 44   GATTGGTTGTTTATTAGTTATTATGT
                (general mismatch „G")

SEQ ID NO: 45   ATTGGTTGTTTATTAGTTATTATGT
                (general mismatch „G")

SEQ ID NO: 46   GATTAGTTGTTTATTAGTTATTATGT
                (general mismatch „A")

SEQ ID NO: 47   ATTAGTTGTTTATTAGTTATTATGT
                (general mismatch „A")

SEQ ID NO: 48   ATT-dS-GTTGTTTATTAGTTATTATGT
                (-dS- = spacer)

SEQ ID NO: 6    GATT-dS-GTTGTTTATTAGTTATTATGT
                (-dS- = spacer)
```

The methylation independent hybridization is achieved by means of a spacer, in particular a dSpacer, or by means of a general mismatching nucleotide such as but not limited to guanine, arginine, or any other artificial suitable nucleotide or base. The term "general" in this context means that the mismatching base forms neither with the methylated cytosine nor the converted unmethylated cytosine a Watson-Crick base pair. Alternatively, the methylation independent hybridization is achieved by means of an universal base such as for example but not limited to nitroindole. In particular, SEQ ID NO: 6 is preferred as forward primer.

One of the following oligonucleotides or an oligonucleotide consisting essentially thereof is used as a reverse primer:

```
SEQ ID NO: 5    AAATAATCCCATCCAACTA
SEQ ID NO: 43   AAATAATCCCATCCAACTAC
```

In particular SEQ ID NO: 5 is preferred as reverse primer.

Preferably, the amplification uses one of the following oligonucleotides or an oligonucleotide consisting essentially thereof, wherein said oligonucleotide is used as a blocker. Through this, in an embodiment, the methylated DNA is preferably amplified over the unmethylated DNA, while in another embodiment, the unmethylated DNA is preferably amplified over the methylated DNA:

```
SEQ ID NO: 7    GTTATTATGTTGGATTTTGTGGTTAATGTGTAG-INV

SEQ ID NO: 49   ATTATGTTGGATTTTGTGGTTAATGTGTAGTTG-INV

SEQ ID NO: 50   ATTATGTTGGATTTTGTGGTTAATGTGTAGTTG-INV

SEQ ID NO: 51   CCATCCAACTACACATTAACCACAAAATCCA-INV

SEQ ID NO: 52   ATCCAACTACACATTAACCACAAAATCCA-INV

SEQ ID NO: 53   CCAACTACACATTAACCACAAAATCCAA-INV

SEQ ID NO: 54   CAACTACACATTAACCACAAAATCCA-INV

SEQ ID NO: 50   ATTATGTTGGATTTTGTGGTTAATGTGTAGTTG-C3

SEQ ID NO: 7    GTTATTATGTTGGATTTTGTGGTTAATGTGTAG-C3
```

-continued

```
SEQ ID NO: 55 ATTAGTTATTATGTTGGATTTTGTGGTTAATGTGTA
              G-C3

SEQ ID NO: 56 AGTTATTATGTTGGATTTTGTGGTTAATGTGTAGTT
              G-C3

SEQ ID NO: 57 TTATGTTGGATTTTGTGGTTAATGTGTAGTTGG-C3
(INV = inverted base linkage (3'-3');
C3 = propyl group)
```

Said oligonucleotides used as blockers may have the indicated modifications or any other suitable modifications enabling the oligonucleotides to act as blockers, for example but not limited to acridine. However, the indicated modifications are in particularly preferred.

In particular, SEQ ID NO: 7 is preferred as blocker. In particular, a C3 modification is preferred to an INV modification.

According to the invention, amplified treated DNA can be detected by any means known in the art. In the simplest case, this is ethidium bromide or SYBR green. Preferably, amplified treated DNA is detected by means of one of the following oligonucleotides or an oligonucleotide consisting essentially thereof, wherein said oligonucleotide is used as probe:

```
SEQ ID NO: 58 HEX-CGGATTTCGCGGTTAACGC-BHQ1

SEQ ID NO: 59 HEX-CGTTAACCGCGAAATCCG-BHQ1

SEQ ID NO: 60 HEX-CGCGTTAACCGCGAAATC-BHQ1

SEQ ID NO: 59 TexRed-CGTTAACCGCGAAATCCG-BBQ650

SEQ ID NO: 8  TexRed-TTAACCGCGAAATCCGAC-BBQ650

SEQ ID NO: 61 TexRed-ATTTCGCGGTTAACGCG-BBQ650
(HEX, TexRed are fluorescent dyes;
BHQ1 = BlackHoleQuencher 1 and
BBQ650 = Black-Berry Quencher 650 are quencher
well known in the art)
```

Said oligonucleotides used as probes may have the indicated labelling with dyes and quenchers or any other suitable labelling with dyes or quenchers. However the indicated dyes or quenchers are In particular preferred.

In particular, SEQ ID NO: 8 is preferred as probe.

In a particularly preferred embodiment (assay C), genomic DNA of SEQ ID NO: 88 is analyzed said sequence being part of the Septin 9 gene. After treatment of the genomic DNA with one or more reagents, preferably with a bisulfite reagent, the antisense strand or the reverse complementary sequence thereof is further analyzed.

For this, one of the following oligonucleotides or an oligonucleotide consisting essentially thereof is used as a forward primer:

```
SEQ ID NO: 12    CCCACCAACCATCATAT

SEQ ID NO: 13    CCCACCAACCATCATATC

SEQ ID NO: 14    ACCCACCAACCATCATA

SEQ ID NO: 15    CTACCCACCAACCATCATAT

SEQ ID NO: 1     CCACCAACCATCATATC
```

In particular, SEQ ID NO: 1 is preferred as forward primer.

One of the following oligonucleotides or an oligonucleotide consisting essentially thereof is used as a reverse primer and hybridizes methylation-independently onto the bisulfite treated DNA:

```
SEQ ID NO: 16    GAAGTTGGAAATGATTTTATTTAGTT
                 (general mismatch „G")

SEQ ID NO: 17    GAAGTTGGAAATGATTTTATTTAGTTG
                 (general mismatch „G")

SEQ ID NO: 18    GAAGTTAGAAATGATTTTATTTAGTT
                 (general mismatch „A")

SEQ ID NO: 19    GAAGTTAGAAATGATTTTATTTAGTTG
                 (general mismatch „A")

SEQ ID NO: 20    AAGTT-dS-GAAATGATTTTATTTAGTT
                 (-dS- = spacer)

SEQ ID NO: 21    GAAGTT-dS-GAAATGATTTTATTTAGTT
                 (-dS- = spacer)

SEQ ID NO: 2     GAAGTT-dS-GAAATGATTTTATTTAGTTG
                 (-dS- = spacer)

SEQ ID NO: 22    AAGTT-dS-GAAATGATTTTATTTAGTTG
                 (-dS- = spacer)
```

The methylation independent hybridization is achieved by means of a spacer, in particular a dSpacer, or by means of a general mismatching nucleotide such as but not limited to guanine, arginine, or any other artificial suitable nucleotide or base. The term "general" in this context means that the mismatching base forms neither with the methylated cytosine nor the converted unmethylated cytosine a Watson-Crick base pair. Alternatively, the methylation independent hybridization is achieved by means of an universal base such as for example but not limited to nitroindole. In particular SEQ ID NO: 21 is preferred as reverse primer.

Preferably, the amplification uses one of the following oligonucleotides or an oligonucleotide consisting essentially thereof as blacker in order to preferably amplify the methylated DNA over the unmethylated DNA:

```
SEQ ID NO: 23    CATCATATCAAACCCCACAATCAACACACAAC-INV

SEQ ID NO: 24    CCATCATATCAAACCCCACAATCAACACACAA-INV

SEQ ID NO: 9     ACCATCATATCAAACCCCACAATCAACACACA-INV

SEQ ID NO: 23    CATCATATCAAACCCCACAATCAACACACAAC-C3

SEQ ID NO: 3     CCATCATATCAAACCCCACAATCAACACACA-C3

SEQ ID NO: 91    CCATCATATCAAACCCCACAATCAACACAC-C3

SEQ ID NO: 25    ATCATATCAAACCCCACAATCAACACACAACT-C3

SEQ ID NO: 26    ACCATCATATCAAACCCCACAATCAACACAC-C3

SEQ ID NO: 27    AACCATCATATCAAACCCCACAATCAACACAC-C3

SEQ ID NO: 28    AGTTGTGTGTTGATTGTGGGGTTTGATA-C3

SEQ ID NO: 29    AGTTGTGTGTTGATTGTGGGGTTTG-C3

SEQ ID NO: 30    ATTTAGTTGTGTGTTGATTGTGGGGTTTGAT-C3
(INV = inverted base linkage (3'-3');
C3 = propyl group)
```

Said oligonucleotides used as blockers may have the Indicated modifications or any other suitable modifications enabling the oligonucleotides to act as blockers, for example but not limited to acridine. However, the indicated modifications are in particular preferred.

In particular, SEQ ID NO: 3 is preferred as blocker. In particular, a C3 modification is preferred to an INV modification.

According to the invention, amplified treated DNA can be detected by any means known in the art. In the simplest case, this is ethidium bromide or SYBR green. Preferably, amplified treated DNA is detected by means of one of the following oligonucleotides or an oligonucleotide consisting essentially thereof, wherein said oligonucleotid is used as probe:

```
SEQ ID NO: 31  FAM-GAACCCCGCGATCAACGCG-BHQ1
SEQ ID NO: 32  FAM-TAGTTGCGCGTTGATCGCGG-BHQ1
SEQ ID NO: 33  FAM-TAGTTGCGCGTTGATCGC-BHQ1
SEQ ID NO: 34  FAM-CCGCGATCAACGCGC-BHQ1
SEQ ID NO: 35  FAM-CGCGTTGATCGCGGG-BHQ1
SEQ ID NO: 36  FAM-CGCGTTGATCGCGG-BHQ1
SEQ ID NO: 37  FAM-ACCCCGCGATCAACG-BHQ1
SEQ ID NO: 38  FAM-TGATCGCGGGGTTCG-BHQ1
SEQ ID NO: 39  FAM-AACCCCGCGATCAAC-BHQ1
SEQ ID NO: 40  FAM-GTTGATCGCGGGGTT-BHQ1
SEQ ID NO: 41  FAM-CCCCGCGATCAACG-BHQ1
SEQ ID NO: 4   FAM-GATCGCGGGGTTCGATA-BHQ1
SEQ ID NO: 42  FAM-CGATCAACGCGCAACTAA-BHQ1
(FAM is a fluorescent dye;
BHQ1 = BlackHoleQuencher 1 is quencher well
known in the art)
```

Said oligonucleotides used as probes may have the indicated labelling with dyes and quenchers or any other suitable labelling with dyes and quenchers. However the indicated dyes and quenchers are in particular preferred. In particular, SEQ ID NO: 4 is preferred as probe.

In a particularly preferred embodiment, an embodiment of assay C is combined with either an embodiment of assay B or with an embodiment of assay A resulting in a combined assay. Preferably, an embodiment of assay C is combined with an embodiment of assay B. The most preferred combination is the following embodiment:

The following oligonucleotides are used as primers: SEQ ID NO: 1, 21, 5, and 6

The following oligonucleotides are used as blockers: SEQ ID NO: 3 and 7

The following oligonucleotides are used as probes: SEQ ID NO: 4 and 8

Of course, for each of said oligonucleotides, an corresponding oligonucleotide consisting essentially of the respective oligonucleotide may also be used instead of it.

In an embodiment of the invention, the position of the oligonucleotides consisting of essentially SEQ ID NO: 1-84 and 91 may be varied. For this, the sequence of the oligonucleotides SEQ ID NO: 1-84, 91 may be amended by 5'-terminal deletion, 3'-terminal deletion, 5'-terminal addition and/or 3'-terminal addition of 1, 2, 3, 4, 5, 6, 7, 8, 9, or 10 nucleotides. The addition of nucleotides is preferably carried out according to the sequence of the converted genomic DNA, wherein cytosines putatively capable of being methylated (cytosine within CpG dinucleotides) are replaced by spacers, universal bases or generally mismatching nucleotides in case the amended oligonucleotide is used as a primer. In case the amended oligonucleotide is used as a blocker, cytosines putatively capable of being methylated remain cytosines wherein the amplification of methylated DNA should be repressed, or said cytosines are replaced by thymine wherein the amplification of unmethylated DNA should be repressed. In case the amended oligonucleotide is used as a probe, cytosines putatively capable of being methylated remain cytosines wherein the amplification of unmethylated DNA should be detected, or said cytosines are replaced by thymine wherein the amplification of unmethylated DNA should be detected.

In a preferred embodiment of the invention, genomic DNA consisting essentially of SEQ ID NO: 89, or more preferably of SEQ ID NO: 90 is analyzed. For this, one, two, three, four or more, preferably two or four oligonucleotides selected from the group consisting of sequences consisting essentially of SEQ ID NO: 1, 2, 5, 6, 12-22, 43-48, 62-72 are used as primers.

It is particularly preferred that one, two, three or more, preferably one or two oligonucleotides selected from the group consisting of sequences consisting essentially of SEQ ID NO: 3, 9, 7, 23-30, 49-57, 73-76, 91 are used as blockers. It is particularly preferred that one, two, three, four or more, preferably one, two, or four oligonucleotides selected from the group consisting of sequences consisting essentially of SEQ ID NO: 4, 8, 31-42, 58-61, 77-84 are used as probes.

In a preferred embodiment, the Septin 9 gene is analyzed by means of oligonucleotides which hybridize under stringent conditions, are identical or complementary to SEQ ID NO: 89, or more preferably SEQ ID NO: 90, as well as to the naturally occurring variant sequences of SEQ ID NO: 89, or more preferably SEQ ID NO: 90. Oligonucleotides to be used as primers have a length in the range of 12-32 nucleotides, preferably 16-18 nucleotides. Oligonucleotides to be used as blockers have a length in the range of 20-45 nucleotides, preferably 25-37 nucleotides. Oligonucleotides to be used as probes have a length in the range of 10-30 nucleotides, preferably 14-25.

One aspect of the invention is a method for amplification, comprising a) treating genomic DNA with one or more reagents to convert unmethylated cytosine bases to uracil sulfonate or to another base having a different binding behavior than cytosine, while methylated cytosine remains unchanged;

b) amplifying the treated DNA by means of
  i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92 wherein said one or more oligonucleotides are suitable for use as primers;
  ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15 wherein said one or more oligonucleotides are suitable for use as primers; and c) deducing the presence or absence of methylation of the CpG dinucleotides amplified in step b) from the result of step b).

Preferably, said method is a method for methylation analysis, in particular a method for detecting the presence of a methylation pattern.

A preferred embodiment comprises additionally the use of at least one oligonucleotide comprising or consisting essentially of a sequence selected from the group consisting of SEQ ID NO: 3, 9, 23-30, SEQ ID NO: 7, 49-57, SEQ ID NO: 7, 49, 50, 55-57, 73-76, 91, SEQ ID NO: 97-101 wherein said one or more oligonucleotides are suitable for use as blockers for the amplification of step (b). A preferred embodiment comprises additionally the use of at least one oligonucleotide comprising or consisting essentially of a sequence selected from the group consisting of SEQ ID NO: 4, 31-42, SEQ ID NO: 8, 58-61, SEQ ID NO: 83 or 84, wherein said one or more oligonucleotides are suitable for use as probes, and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105, wherein said one or more oligonucleotide combinations are suitable for use as probe combinations, for the amplification of step (b). A preferred embodiment comprises additionally the use of a polymerase, preferably a heat stable polymerase, for the amplification of step (b).

A particularly preferred embodiment of the inventiv method comprises a) treating the genomic DNA with one or more reagents to convert unmethylated cytosine bases to uracil sulfonate or to another base having a different binding behavior than cytosine, while methylated cytosine remains unchanged;

b) amplifying the treated DNA by means of
  i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92, wherein said one or more oligonucleotides are suitable for use as primers;
  ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15, wherein said one or more oligonucleotides are suitable for use as primers;
  iii) at least one oligonucleotide comprising or consisting essentially of a sequence selected from the group consisting of SEQ ID NO: 3, 9, 23-30, SEQ ID NO: 7, 49-57, SEQ ID NO: 7, 49, 50, 55-57, 73-76, 91, SEQ ID NO: 97-101, wherein said one or more oligonucleotides are suitable for use as blockers;
  iv) at least one oligonucleotide comprising or consisting essentially of a sequence selected from the group consisting of SEQ ID NO: 4, 31-42, SEQ ID NO: 8, 58-61, SEQ ID NO: 83 or 84, wherein said one or more oligonucleotides are suitable for use as probes and/or at least one oligonucleotide combination comprising or consisting essentially of either the sequences of SEQ ID NO: 77 and 78, of SEQ ID NO: 79 and 80, of SEQ ID NO: 81 and B2, of SEQ ID NO: 102 and 103, or of SEQ ID NO: 104 and 105, wherein said one or more oligonucleotide combinations are suitable for use as probe combinations; and
  v) a heat stable polymerase; and c) deducing the presence or absence of a methylation from the result of step b).

A preferred embodiment of the inventive method, comprises a) using an oligonucleotide suitable for use as a primer, said oligonucleotide comprising or consisting essentially of a sequence selected from the group consisting of SEQ ID NO: 6, 48, 62-64; and b) using an oligonucleotide suitable for use as a primer, said oligonucleotide comprising or consisting essentially of a sequence selected from the group consisting of SEQ ID NO: 65-72.

An embodiment is also preferred which comprises additionally the use of an oligonucleotide comprising or consisting essentially of a sequence selected from the group consisting of SEQ ID NO: 7, 49, 50, 55-57, 73-76, wherein said oligonucleotide is suitable for use as a blocker. An embodiment is also preferred which comprises additionally the use of an oligonucleotide comprising or consisting essentially of SEQ ID NO: 83 or of SEQ ID NO: 84, wherein said oligonucleotide is suitable for use as a probe, or the use of an oligonucleotide combination comprising or consisting essentially of either the sequences of SEQ ID NO: 77 and 78, of SEQ ID NO: 79 and 80, or of SEQ ID NO: 81 and 82, wherein said combination is suitable for use as a probe combination.

A preferred embodiment of the inventive method, comprises a) using an oligonucleotide suitable for use as a primer, said oligonucleotide comprising or consisting essentially of a sequence selected from the group consisting of SEQ ID NO: 6, 48, 62-64;

b) using an oligonucleotide suitable for use as a primer, said oligonucleotide comprising or consisting essentially of a sequence selected from the group consisting of SEQ ID NO: 65-72;

c) using oligonucleotide suitable for use as a blocker, said oligonucleotide comprising or consisting essentially of a sequence selected from the group consisting of SEQ ID NO: 7, 49, 50, 55-57, 73-76; and d) using an oligonucleotide suitable for use as a probe, said oligonucleotide comprising or consisting essentially of SEQ ID NO: 83 or of SEQ ID NO: 84, or using an oligonucleotide combination suitable for use as a probe combination, said oligonucleotide combination comprising or consisting essentially of either the sequences of SEQ ID NO: 77 and 78, of SEQ ID NO: 79 and 80, or of SEQ ID NO: 81 and 82.

A most particular preferred embodiment of the inventive method comprises a) using an oligonucleotide comprising or consisting essentially of the sequence of SEQ ID NO: 6; and b) using an oligonucleotide comprising or consisting essentially of the sequence of SEQ ID NO: 65.

A most particular preferred embodiment of the inventive method comprises additionally using an oligonucleotide comprising or consisting essentially of the sequence of SEQ ID NO: 7. A most particular preferred embodiment of the Inventive method comprises additionally an oligonucleotide combination comprising or consisting essentially of the sequences of SEQ ID NO: 81 and 82.

A most particular preferred embodiment of the inventive method comprises a) using an oligonucleotide comprising or consisting essentially of the sequence of SEQ ID NO: 6;

b) using an oligonucleotide comprising or consisting essentially of the sequence of SEQ ID NO: 65;

c) using an oligonucleotide comprising or consisting essentially of the sequence of SEQ ID NO: 7; and d) using an oligonucleotide combination comprising or consisting essentially of the sequences of SEQ ID NO: 81 and 82.

A preferred embodiment of the inventive method, comprises a) using an oligonucleotide suitable for use as a primer, said oligonucleotide comprising or consisting essentially of a sequence selected from the group consisting of SEQ ID NO: 6, 44-48; and b) using an oligonucleotide suitable for use as a primer, said oligonucleotide comprising or consisting essentially of a sequence selected from the group consisting of SEQ ID NO: 5, 43.

An embodiment is also preferred which comprises additionally the use of an oligonucleotide comprising or consisting essentially of a sequence selected from the group consisting of SEQ ID NO: 7, 49-57, wherein said oligonucleotide is suitable for use as a blocker. An embodiment is also preferred which comprises additionally the use of an oligonucleotide oligonucleotide comprising or consisting essentially of a sequence selected from the group consisting of SEQ ID NO: 8, 58-61, wherein said oligonucleotide is suitable for use as a probe.

A preferred embodiment of the inventive method, comprises
   a) using an oligonucleotide suitable for use as a primer, said oligonucleotide comprising or consisting essentially of a sequence selected from the group consisting of SEQ ID NO: 6, 44-48;
   b) using an oligonucleotide suitable for use as a primer, said oligonucleotide comprising or consisting essentially of a sequence selected from the group consisting of SEQ ID NO: 5, 43;
   c) using an oligonucleotide suitable for use as a blocker, said oligonucleotide comprising or consisting essentially of a sequence selected from the group consisting of SEQ ID NO: 7, 49-57; and
   d) using an oligonucleotide suitable for use as a probe, said oligonucleotide comprising or consisting essentially of a sequence selected from the group consisting of SEQ ID NO: 8, 58-61.

A most particular preferred embodiment of the inventive method comprises
   a) using an oligonucleotide comprising or consisting essentially of the sequence of SEQ ID NO: 5; and
   b) using an oligonucleotide comprising or consisting essentially of the sequence of SEQ ID NO: 6.

A most particular preferred embodiment of the inventive method comprises additionally using an oligonucleotide comprising or consisting essentially of the sequence of SEQ ID NO: 7. A most particular preferred embodiment of the inventive method comprises additionally using an oligonucleotide comprising or consisting essentially of the sequence of SEQ ID NO: 8.

A most particular preferred embodiment of the inventive method comprises
   a) using an oligonucleotide comprising or consisting essentially of the sequence of SEQ ID NO: 5;
   b) using an oligonucleotide comprising or consisting essentially of the sequence of SEQ ID NO: 6;
   c) using an oligonucleotide comprising or consisting essentially of the sequence of SEQ ID NO: 7; and
   d) using an oligonucleotide comprising or consisting essentially of the sequence of SEQ ID NO: 8.

A preferred embodiment of the inventive method, comprises
   a) using an oligonucleotide suitable for use as a primer, said oligonucleotide comprising or consisting essentially of a sequence selected from the group consisting of SEQ ID NO: 1, 12-15; and
   b) using an oligonucleotide suitable for use as a primer, said oligonucleotide comprising or consisting essentially of a sequence selected from the group consisting of SEQ ID NO: 2, 16-22.

An embodiment is also preferred which comprises additionally the use of an oligonucleotide comprising or consisting essentially of a sequence selected from the group consisting of SEQ ID NO: 3, 9, 23-30, 91, wherein said oligonucleotide is suitable for use as a blocker. An embodiment is also preferred which comprises additionally the use of an oligonucleotide comprising or consisting essentially of a sequence selected from the group consisting of SEQ ID NO: 4, 31-42, wherein said oligonucleotide is suitable for use as a probe.

A preferred embodiment of the inventive method, comprises
   a) using an oligonucleotide suitable for use as a primer, said oligonucleotide comprising or consisting essentially of a sequence selected from the group consisting of SEQ ID NO: 1, 12-15;
   b) using an oligonucleotide suitable for use as a primer, said oligonucleotide comprising or consisting essentially of a sequence selected from the group consisting of SEQ ID NO: 2, 16-22;
   c) using an oligonucleotide suitable for use as a blocker, said oligonucleotide comprising or consisting essentially of a sequence selected from the group consisting of SEQ ID NO: 3, 9, 23-30, 91; and
   d) using an oligonucleotide suitable for use as a probe, said oligonucleotide comprising or consisting essentially of a sequence selected from the group consisting of SEQ ID NO: 4, 31-42.

A most particular preferred embodiment of the inventive method comprises
   a) using an oligonucleotide comprising or consisting essentially of the sequence of SEQ ID NO: 1;
   b) using an oligonucleotide comprising or consisting essentially of the sequence of SEQ ID NO: 21.

A most particular preferred embodiment of the inventive method comprises additionally using an oligonucleotide comprising or consisting essentially of the sequence of SEQ ID NO: 3. A most particular preferred embodiment of the inventive method comprises additionally using an oligonucleotide comprising or consisting essentially of the sequence of SEQ ID NO: 4.

A most particular preferred embodiment of the inventive method comprises
   a) using an oligonucleotide comprising or consisting essentially of the sequence of SEQ ID NO: 1;
   b) using an oligonucleotide comprising or consisting essentially of the sequence of SEQ ID NO: 21;
   c) using an oligonucleotide comprising or consisting essentially of the sequence of SEQ ID NO: 3; and
   d) using an oligonucleotide comprising or consisting essentially of the sequence of SEQ ID NO: 4.

A preferred embodiment of the inventive method, comprises
   a) using an oligonucleotide suitable for use as a primer, said oligonucleotide comprising or consisting essentially of the sequence of SEQ ID NO: 92; and
   b) using an oligonucleotide suitable for use as a primer, said oligonucleotide comprising or consisting essentially of a sequence selected from the group consisting of SEQ ID NO: 1, 12-15.

An embodiment is also preferred which comprises additionally the use of an oligonucleotide comprising or consisting essentially of a sequence selected from the group consisting of SEQ ID NO: 9, 23, 24, 91, 97-101, wherein said oligonucleotide is suitable for use a blocker.

An embodiment is also preferred which comprises additionally the use of an oligonucleotide comprising or consisting essentially of a sequence selected from the group consisting of SEQ ID NO: 4, 31-42, wherein said oligonucleotide is suitable for use a probe, or the use of an oligonucleotide combination comprising or consisting essentially of a sequence combination selected from the group consisting of SEQ ID NO: 102 and 103 and of SEQ ID NO: 104 and 105, wherein said oligonucleotide combination is suitable for use as a probe combination.

A preferred embodiment of the inventive method, comprises a) using an oligonucleotide suitable for use as a primer, said oligonucleotide comprising or consisting essentially of the sequence of SEQ ID NO: 92;

b) using an oligonucleotide suitable for use as a primer, said oligonucleotide comprising or consisting essentially of a sequence selected from the group consisting of SEQ ID NO: 1, 12-15;

c) using an oligonucleotide suitable for use as a blocker, said oligonucleotide comprising or consisting essentially of a sequence selected from the group consisting of SEQ ID NO: 9, 23, 24, 91, 97-101; and d) using an oligonucleotide suitable for use as a probe, said oligonucleotide comprising or consisting essentially of a sequence selected from the group consisting of SEQ ID NO: 4, 31-42, or using an oligonucleotide combination suitable for use a probe combination, said oligonucleotide combination comprising or consisting essentially of a sequence combination selected from the group consisting of SEQ ID NO: 102 and 103, and of SEQ ID NO: 104 and 105.

One aspect of the invention is a method for amplification wherein two or more oligonucleotides comprising or consisting essentially of a sequence selected from the group consisting of SEQ ID NO: 92-96 and 31 or from the group consisting of SEQ ID NO: 1, 4, 9, 12-15, 23, 24, 31-42, 91, 92, 97-101, 102-105 are combined with two or more oligonucleotides comprising or consisting essentially of a sequence selected from the group consisting of SEQ ID NO: 6, 7, 48-50, 55-57, 62-84 or with two or more oligonucleotides comprising or consisting essentially of a sequence selected from the group consisting of SEQ ID NO: 5-8, 43-61 resulting in a combined assay. Said method is a method wherein each of the strands of a treated genomic DNA is analyzed. Said treatment is a treatment wherein cytosine is converted to uracil sulfonate or another base having a different binding behavior than cytosine, while methylated cytosine remains unchanged. Preferably, said method is a method for methylation analysis, in particular a method for detecting the presence of a methylation pattern.

A preferred embodiment of said combined assay, comprises a) treating genomic DNA with one or more reagents to convert unmethylated cytosine bases to uracil sulfonate or to another base having a different binding behavior than cytosine, while methylated cytosine remains unchanged;

b) amplifying the treated DNA by means of i) an oligonucleotide suitable for use as a primer, said oligonucleotide comprising or consisting essentially of a sequence of SEQ ID NO: 92 and of an oligonucleotide suitable for use as a primer, said oligonucleotide comprising or consisting essentially of a sequence selected from the group consisting of SEQ ID NO: 6, 44-48; SEQ ID NO: 6, 48, 62-64 ii) an oligonucleotide suitable for use as a primer, said oligonucleotide comprising or consisting essentially of a sequence of SEQ ID NO: 1, 12-15, 93 and of an oligonucleotide suitable for use as a primer, said oligonucleotide comprising or consisting essentially of a sequence selected from the group consisting of SEQ ID NO: 5, 43; SEQ ID NO: 65-72;

iii) optinal, at least one oligonucleotide suitable for use as a blocker, said one or more and oligonucleotide comprising or consisting essentially of a sequence selected from the group consisting of SEQ ID NO: 9, 23, 24, 97-101, 94, SEQ ID NO: 7, 49-57; SEQ ID NO: 7, 49, 50, 55-57, 73-76, 91; and iv) optional, at least one oligonucleotide suitable for use as a probe, said oligonucleotide comprising or consisting essentially of a seuqnece selected from the group consisting of SEQ ID NO: 4, 31-42, SEQ ID NO: 8, 58-61, SEQ ID NO: 83, 84, and/or at least one oligonucleotide combination suitable for use as probe combination, said oligonucleotide combination comprising or consisting essentially of the sequences of SEQ ID NO: 95 and 96, of SEQ ID NO: 102 and 103, of SEQ ID NO: 104 and 105, and of SEQ ID NO: 81 and 82;

v) optional, a polymerase, preferably a heatstable polymerase; and c) deducing the presence or absence of methylation of the CpG dinucleotides amplified in step b) from the result of step b).

Said method is a method wherein each of the strands of a treated genomic DNA is analyzed. Preferably, said method is a method for methylation analysis, in particular a method for detecting the presence of a methylation pattern.

A preferred embodiment of said combined assay, comprises a) treating genomic DNA with one or more reagents to convert unmethylated cytosine bases to uracil sulfonate or to another base having a different binding behavior than cytosine, while methylated cytosine remains unchanged;

b) amplifying the treated DNA by means of i) an oligonucleotide suitable for use as a primer, said oligonucleotide comprising or consisting essentially of a sequence of SEQ ID NO: 92 and of an oligonucleotide suitable for use as a primer, said oligonucleotide comprising or consisting essentially of a sequence selected from the group consisting of SEQ ID NO: 6, 44-48; SEQ ID NO: 6, 48, 62-64 ii) an oligonucleotide suitable for use as a primer, said oligonucleotide comprising or consisting essentially of a sequence of SEQ ID NO: 1, 12-15, 93 and of an oligonucleotide suitable for use as a primer, said oligonucleotide comprising or consisting essentially of a sequence selected from the group consisting of SEQ ID NO: 5, 43; SEQ ID NO: 65-72;

iii) at least one oligonucleotide suitable for use as a blocker, said one or more and oligonucleotide comprising or consisting essentially of a sequence selected from the group consisting of SEQ ID NO: 9, 23, 24, 97-101, 94, SEQ ID NO: 7, 49-57; SEQ ID NO: 7, 49, 50, 55-57, 73-76, 91; and iv) at least one oligonucleotide suitable for use as a probe, said oligonucleotide comprising or consisting essentially of a seuqnece selected from the group consisting of SEQ ID NO: 4, 31-42, SEQ ID NO: 8, 58-61, SEQ ID NO: 83, 84, and/or at least one oligonucleotide combination suitable for use as probe combination, said oligonucleotide combination comprising or consisting essentially of the sequences of SEQ ID NO: 95 and 96, of SEQ ID NO: 102 and 103, of SEQ ID NO: 104 and 105, and of SEQ ID NO: 81 and 82;

v) a polymerase, preferably a heatstable polymerase; and c) deducing the presence or absence of methylation of the CpG dinucleotides amplified in step b) from the result of step b).

Said method is a method wherein each of the strands of a treated genomic DNA is analyzed.

Preferably, said method Is a method for methylation analysis, in particular a method for detecting the presence of a methylation pattern.

A particular preferred embodiment of the combined assay comprises a) treating genomic DNA with one or more reagents to convert unmethylated cytosine bases to uracil sulfonate or to another base having a different binding behavior than cytosine, while methylated cytosine remains unchanged;

b) amplifying the treated DNA by means of
  i) an oligonucleotide suitable for use as a primer, said oligonucleotide comprising or consisting essentially of a sequence of SEQ ID NO: 92; and
  ii) an oligonucleotide suitable for use as a primer, said oligonucleotide comprising or consisting essentially of a sequence of SEQ ID NO: 1, 12-15, 93;
  iii) an oligonucleotide suitable for use as a primer, said oligonucleotide comprising or consisting essentially of a sequence selected from the group consisting of SEQ ID NO: 6, 48, 62-64; and
  iv) an oligonucleotide suitable for use as a primer, said oligonucleotide comprising or consisting essentially of a sequence selected from the group consisting of SEQ ID NO: 65-72; and c) deducing the presence or absence of methylation of the CpG dinucleotides amplified in step b) from the result of step b).

A particularly preferred embodiment of a combined assay comprises additionally an oligonucleotide comprising or consisting essentially of a sequence selected from the group consisting of SEQ ID NO: 9, 23, 24, 97-101, 94 and/or an oligonucleotide comprising or consisting essentially of a sequence selected from the group consisting of SEQ ID NO: 7, 49, 50, 55-57, 73-76, wherein said one or two oligonucleotides are suitable for use as a blocker.

A particularly preferred embodiment of a combined assay comprises additionally an oligonucleotide comprising or consisting essentially of a sequence selected from the group consisting of SEQ ID NO: 4, 31-42, wherein said oligonucleotide is suitable for use as a probe, or an oligonucleotide combination comprising or consisting essentially of the sequences of SEQ ID NO: 95 and 96, of SEQ ID NO: 102 and 103, or of SEQ ID NO: 104 and 105, and wherein said oligonucleotide combination is suitable for use as a probe combination.

A particularly preferred embodiment of a combined assay comprises additionally an oligonucleotide comprising or consisting essentially of the sequence of either SEQ ID NO: 83 or SEQ ID NO: 84, or an oligonucleotide combination comprising or consisting essentially of the sequences of either of SEQ ID NO: 77 and 78, of SEQ ID NO: 79 and 80, or of SEQ ID NO: 81 and 82, wherein said oligonucleotide is suitable for use as a probe, and wherein said oligonucleotide combination is suitable for use as a probe combination.

A particularly preferred embodiment of a combined assay comprises a) using an oligonucleotide suitable for use of a primer, said oligonucleotide comprising or consisting essentially of a sequence of SEQ ID NO: 92;

b) using an oligonucleotide suitable for use of a primer, said oligonucleotide comprising or consisting essentially of a sequence of SEQ ID NO: 1, 12-15, 93;

c) using an oligonucleotide suitable for use of a primer, said oligonucleotide comprising or consisting essentially of a sequence selected from the group consisting of SEQ ID NO: 6, 48, 62-64;

d) using an oligonucleotide suitable for use of a primer, said oligonucleotide comprising or consisting essentially of a sequence selected from the group consisting of SEQ ID NO: 65-72;

e) using an oligonucleotide suitable for use of a blocker, said oligonucleotide comprising or consisting essentially of a sequence of SEQ ID NO: 9, 23, 24, 97-101, 94;

f) using an oligonucleotide suitable for use of a probe, said oligonucleotide comprising or consisting essentially of the sequence of SEQ ID NO: 4, 31-42, or using an oligonucleotide combination suitable for use of a probe combination, said oligonucleotide combination comprising or consisting essentially of the sequences of SEQ ID NO: 95 and 96, of SEQ ID NO: 102 and 103, of SEQ ID NO: 104 and 105;

g) using an oligonucleotide suitable for use of a blocker, said oligonucleotide comprising or consisting essentially of a sequence selected from the group consisting of SEQ ID NO: 7, 49, 50, 55-57, 73-76; and h) using an oligonucleotide suitable for use of a probe, said oligonucleotide comprising or consisting essentially of the sequence of either SEQ ID NO: 83 or SEQ ID NO: 84, or using an oligonucleotide combination suitable for use of a probe combination, said oligonucleotide combination comprising or consisting essentially of the sequences of either of SEQ ID NO: 77 and 78, of SEQ ID NO: 79 and 80, or of SEQ ID NO: 81 and 82.

A particularly preferred embodiment of a combined assay comprises a) using an oligonucleotide suitable for use of a primer, said oligonucleotide comprising or consisting essentially of a sequence of SEQ ID NO: 92;

b) using an oligonucleotide suitable for use of a primer, said oligonucleotide comprising or consisting essentially of a sequence of SEQ ID NO: 1, 12-15, 93;

c) using an oligonucleotide suitable for use of a primer, said oligonucleotide comprising or consisting essentially of a sequence selected from the group consisting of SEQ ID NO: 6, 44-48; and d) using an oligonucleotide suitable for use of a primer, said oligonucleotide comprising or consisting essentially of a sequence selected from the group consisting of SEQ ID NO: 5, 43.

A particularly preferred embodiment of a combined assay comprises additionally an oligonucleotide suitable for use as a blocker, said oligonucleotide comprising or consisting essentially of a sequence of SEQ ID NO: 9, 23, 24, 97-101, 94 and/or an oligonucleotide suitable for use as a blocker, said oligonucleotide comprising or consisting essentially of a sequence selected from the group consisting of SEQ ID NO: 7, 49-57.

A particularly preferred embodiment of a combined assay comprises additionally an oligonucleotide suitable for use as a probe, said oligonucleotide comprising or consisting essentially of the sequence of SEQ ID NO: 4, 31-42 or an oligonucleotide combination suitable for use as a probe combination, said oligonucleotide combination comprising or consisting essentially of the sequences of SEQ ID NO: 95 and 96, of SEQ ID NO: 102 and 103, of SEQ ID NO: 104 and 105 in combination with an oligonucleotide suitable for use as a probe, said oligonucleotide comprising or consisting essentially of a sequence selected from the group consisting of SEQ ID NO: 8, 58-61.

A particularly preferred embodiment of a combined assay comprises a) using an oligonucleotide suitable for use of a primer, said oligonucleotide comprising or consisting essentially of a sequence of SEQ ID NO: 92;

b) using an oligonucleotide suitable for use of a primer, said oligonucleotide comprising or consisting essentially of a sequence of SEQ ID NO: 1, 12-15, 93;

c) using an oligonucleotide suitable for use of a primer, said oligonucleotide comprising or consisting essentially of a sequence selected from the group consisting of SEQ ID NO: 6, 44-48;

d) using an oligonucleotide suitable for use of a primer, said oligonucleotide comprising or consisting essentially of a sequence selected from the group consisting of SEQ ID NO: 5, 43;

e) using an oligonucleotide suitable for use of a blocker, said oligonucleotide comprising or consisting essentially of a sequence of SEQ ID NO: 9, 23, 24, 97-101, 94;

f) using an oligonucleotide suitable for use of a blocker, said oligonucleotide comprising or consisting essentially of a sequence selected from the group consisting of SEQ ID NO: 7, 49-57;

g) using an oligonucleotide suitable for use of a probe, said oligonucleotide comprising or consisting essentially of the sequence of SEQ ID NO: 4, 31-42, or using an oligonucleotide combination suitable for use of a probe combination, said oligonucleotide combination comprising or consisting essentially of the sequences of SEQ ID NO: 95 and 96, of SEQ ID NO: 102 and 103, of SEQ ID NO: 104 and 105; and h) using an oligonucleotide suitable for use of a probe, said oligonucleotide comprising or consisting essentially of a sequence selected from the group consisting of SEQ ID NO: 8, 58-61.

A particularly preferred embodiment of a combined assay comprises the oligonucleotides comprising or consisting essentially of the sequence of SEQ ID NO: 92, 93, 5 and 6. Said oligonucleotides are suitable for use as primers.

A particularly preferred embodiment of a combined assay comprises a) the oligonucleotides comprising or consisting essentially of the sequence of SEQ ID NO: 92, 93, 5 and 6, wherein said oligonucleotides are suitable for use as primers;

b) the oligonucleotide comprising or consisting essentially of the sequence of SEQ ID NO: 94, the oligonucleotide comprising or consisting essentially of the sequence of SEQ ID NO: 7, or both, wherein said one or more oligonucleotides are suitable for use a blockers; and c) the oligonucleotide combination comprising or consisting essentially of the sequences of SEQ ID NO: 95 and 96, the oligonucleotide comprising or consisting essentially of the sequence of SEQ ID NO: 8, or both, wherein said combination are suitable for use as probe combination, and wherein said oligonucleotide is suitable for use a probe.

One aspect of the invention is a method for amplification wherein two or more oligonucleotides comprising or consisting essentially of a sequence selected from the group consisting of SEQ ID NO: 1-4, 9, 12-42, 91 are combined with two or more oligonucleotides comprising or consisting essentially of a sequence selected from the group consisting of SEQ ID NO: 6, 7, 48-50, 55-57, 62-84 or with two or more oligonucleotides comprising or consisting essentially of a sequence selected from the group consisting of SEQ ID NO: 5-8, 43-61 resulting in a combined assay. Said method is a method wherein each of the strands of a treated genomic DNA is analyzed. Said treatment is a treatment wherein cytosine is converted to uracil sulfonate or another base having a different binding behavior than cytosine, while methylated cytosine remains unchanged. Preferably, said method is a method for methylation analysis, in particular a method for detecting the presence of a methylation pattern.

A preferred embodiment of said combined assay, comprises a) treating genomic DNA with one or more reagents to convert unmethylated cytosine bases to uracil sulfonate or to another base having a different binding behavior than cytosine, while methylated cytosine remains unchanged;

b) amplifying the treated DNA by means of
i) an oligonucleotide comprising or consisting essentially of a sequence selected from the group consisting of SEQ ID NO: 1, 12-15, and an oligonucleotide comprising or consisting essentially of a sequence selected from the group consisting of SEQ ID NO: 6, 44-48; SEQ ID NO: 6, 48, 62-64; and
ii) an oligonucleotide comprising or consisting essentially of a sequence selected from the group consisting of SEQ ID NO: 2, 16-22 and an oligonucleotide comprising or consisting essentially of a sequence selected from the group consisting of SEQ ID NO: 5, 43; SEQ ID NO: 65-72; and c) deducing the presence or absence of methylation of the CpG dinucleotides amplified in step b) from the result of step b).

Said method is a method wherein each of the strands of a treated genomic DNA is analyzed. Preferably, said method is a method for methylation analysis, in particular a method for detecting the presence of a methylation pattern.

A particular preferred embodiment of the combined assay comprises additionally at least one oligonucleotide comprising or consisting essentially of a sequence selected from the group consisting of SEQ ID NO: 3, 9, 23-30; SEQ ID NO: 7, 49-57; SEQ ID NO: 7, 49, 50, 55-57, 73-76, 91. A particular preferred embodiment of the combined assay comprises additionally at least one oligonucleotide comprising or consisting essentially of a sequence selected from the group consisting of SEQ ID NO: 4, 31-42; SEQ ID NO: 8, 58-61; SEQ ID NO: 83 or 84, and/or an oligonucleotide combination comprising or consisting essentially of the sequences of SEQ ID NO: 77 and 78, of SEQ ID NO: 79 and 80, and of SEQ ID NO: 81 and 82. A particular preferred embodiment of the combined assay comprises additionally a polymerase, preferably a heatstable polymerase.

A particular preferred embodiment of the combined assay comprises a) treating genomic DNA with one or more reagents to convert unmethylated cytosine bases to uracil sulfonate or to another base having a different binding behavior than cytosine, while methylated cytosine remains unchanged;

b) amplifying the treated DNA by means of
i) an oligonucleotide comprising or consisting essentially of a sequence selected from the group consisting of SEQ ID NO: 1, 12-15, and an oligonucleotide comprising or consisting essentially of a sequence selected from the group consisting of SEQ ID NO: 6, 44-48; SEQ ID NO: 6, 48, 62-64;
ii) an oligonucleotide comprising or consisting essentially of a sequence selected from the group consisting of SEQ ID NO: 2, 16-22 and an oligonucleotide comprising or consisting essentially of a sequence selected from the group consisting of SEQ ID NO: 5, 43; SEQ ID NO: 65-72;
iii) at least one oligonucleotide comprising or consisting essentially of a sequence selected from the group consisting of SEQ ID NO: 3, 9, 23-30; SEQ ID NO: 7, 49-57; SEQ ID NO: 7, 49, 50, 55-57, 73-76, 91; and
iv) at least one oligonucleotide comprising or consisting essentially of a sequence selected from the group consisting of SEQ ID NO: 4, 31-42; SEQ ID NO: 8, 58-61; SEQ ID NO: 83 or 84, and/or an oligonucleotide combination comprising or consisting essentially of the sequences of SEQ ID NO: 77 and 78, of SEQ ID NO: 79 and 80, and of SEQ ID NO: 81 and 82; and c) deducing the presence or absence of methylation of the CpG dinucleotides amplified in step b) from the result of step b).

Said method is a method wherein each of the strands of a treated genomic DNA is analyzed. Preferably, said method is a method for methylation analysis, in particular a method for detecting the presence of a methylation pattern.

Most particularly preferred is an embodiment of the combined assay, wherein the treated DNA is amplified by means of the oligonucleotides comprising or consisting essentially of the sequence of SEQ ID NO: 1, 21, 5 and 6. A most particular preferred embodiment comprises additionally the oligonucleotide comprising or consisting essentially of the sequence of SEQ ID NO: 3, the oligonucleotide comprising or consisting essentially of the sequence of SEQ ID NO: 7, or both. A most particular preferred embodiment comprises additionally the oligonucleotide comprising or consisting essentially of the sequence of SEQ ID NO: 4, the oligonucleotide comprising or consisting essentially of the sequence of SEQ ID NO: 8, or both.

Most particularly preferred is an embodiment of the combined assay, wherein the treated DNA is amplified by means of
a) the oligonucleotides comprising or consisting essentially of the sequence of SEQ ID NO: 1, 21, 5 and 6;
b) the oligonucleotide comprising or consisting essentially of the sequence of SEQ ID NO: 3, the oligonucleotide comprising or consisting essentially of the sequence of SEQ ID NO: 7, or both; and
c) the oligonucleotide comprising or consisting essentially of the sequence of SEQ ID NO: 4, the oligonucleotide comprising or consisting essentially of the sequence of SEQ ID NO: 8, or both.

One aspect of the invention is a method for detecting and/or classifying cellular proliferative disorders. Said method comprises:
a) treating genomic DNA with one or more reagents to convert unmethylated cytosine bases to uracil sulfonate or to another base having a different binding behavior than cytosine, while methylated cytosine remains unchanged;
b) amplifying the treated DNA by means of
  i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92, said one or more oligonucleotides are suitable for use as primers;
  ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15, said one or more oligonucleotides are suitable for use as primers; and
c) deducing the presence or absence of methylation of the CpG dinucleotides amplified in step b) from the result of step b), wherein at least one of detecting and classifying cellular proliferative disorders is, at least in part, afforded.

A preferred embodiment of the inventive method comprises additionally using at least one oligonucleotide comprising or consisting essentially of a sequence selected from the group consisting of SEQ ID NO: 3, 9, 23-30, 91, SEQ ID NO: 7, 49-57, SEQ ID NO: 7, 49, 50, 55-57, 73-76, SEQ ID NO: 97-101, said one or more oligonucleotides are suitable for use as blockers. A preferred embodiment of the inventive method comprises additionally using at least one oligonucleotide comprising or consisting essentially of a sequence selected from the group consisting of SEQ ID NO: 4, 31-42, SEQ ID NO: 8, 58-61, SEQ ID NO: 83 or 84, said one or more oligonucleotides are suitable for use as probes, and/or at least one oligonucleotide combination comprising or consisting essentially of the sequences of SEQ ID NO: 77 and 78, of SEQ ID NO: 79 and 80, of SEQ ID NO: 81 and 82, of SEQ ID NO: 102 and 103, or of SEQ ID NO: 104 and 105, said one or more oligonucleotide combinations are suitable for use probe combinations. A preferred embodiment of the inventive method comprises additionally using a polymerase, preferably a heat stable polymerase.

A preferred embodiment for detecting and/or classifying cellular proliferative disorders comprises:
a) treating genomic DNA with one or more reagents to convert unmethylated cytosine bases to uracil sulfonate or to another base having a different binding behavior than cytosine, while methylated cytosine remains unchanged;
b) amplifying the bisulfite treated DNA by means of
  i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92;
  ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15;
  iii) at least one oligonucleotide comprising or consisting essentially of a sequence selected from the group consisting of SEQ ID NO: 3, 9, 23-30, 91, SEQ ID NO: 7, 49-57, SEQ ID NO: 7, 49, 50, 55-57, 73-76, SEQ ID NO: 97-101;
  iv) at least one oligonucleotide comprising or consisting essentially of a sequence selected from the group consisting of SEQ ID NO: 4, 31-42, SEQ ID NO: 8, 58-61, SEQ ID NO: 83 or 84, and/or at least one oligonucleotide combination comprising or consisting essentially of the sequences of SEQ ID NO: 77 and 78, of SEQ ID NO: 79 and 80, of SEQ ID NO: 81 and 82, of SEQ ID NO: 102 and 103, or of SEQ ID NO: 104 and 105; and
  v) a heat stable polymerase; and
c) deducing the presence or absence of methylation of the CpG dinucleotides amplified in step b) from the result of step b), wherein at least one of detecting and classifying cellular proliferative disorders is, at least in part, afforded.

Particularly preferred is an embodiment of the inventive method for detecting and/or classifying cellular proliferative disorders, wherein said genomic DNA is isolated by means of Si-MAG/FK-Silanol beads (Chemicell, Germany, Article Number: 1101-1 or 1101-5) and/or beads of the chemagic Viral DNA/RNA Kit special (Chemagen, Germany, Article Number 1002).

Particularly preferred is an embodiment of the inventive method for detecting and/or classifying cellular proliferative disorders, wherein the treating of genomic DNA comprises the subsequent purification of the converted DNA by means of SiMAG/FK-Silanol beads (Chemicell, Germany, Article Number: 1101-1 or 1101-5) and/or beads of the chemagic Viral DNA/RNA Kit special (Chemagen, Germany, Article Number 1002).

Oligonucleotides and Oligonucleotide Composition

One aspect of the invention is an oligonucleotide. Said oligonucleotide comprises or consists essentially of a sequence selected from the group consisting of SEQ ID NO: 1-30, 32-84, 91, 97-105.

One aspect of the invention is an oligonucleotide composition. Said oligonucleotide composition comprises or consists of one, two, three, four or more oligonucleotides comprising or consisting essentially of a sequence selected from the group consisting of SEQ ID NO: 1-30, 32-84, 91, 97-105. If the case may be, the said oligonucleotide composition may also comprise additionally one, two, three, four or more oligonucleotides comprising or consisting essentially of a sequence selected from the group consisting of SEQ ID NO: 92-96 and 31.

According to the invention an oligonucleotide or an oligonucleotide composition is preferred, said oligonucleotide or the oligonucleotides of said composition comprising or consisting essentially of a sequence selected from the group consisting of SEQ ID NO: 1-30, 32-84, 91, 97-105.

A preferred oligonucleotide composition comprises
i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92 suitable for use as a primer;
ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15 suitable for use as a primer.

A preferred oligonucleotide composition comprises in addition at least one oligonucleotide comprising or consisting essentially of a sequence selected from the group consisting of SEQ ID NO: 3, 9, 23-30, SEQ ID NO: 7, 49-57, SEQ ID NO: 7, 49, 50, 55-57, 73-76, 91, SEQ ID NO: 97-101 suitable for use as a blocker. A further preferred oligonucleotide composition comprises in addition at least one oligonucleotide comprising or consisting essentially of a sequence selected from the group consisting of SEQ ID NO: 4, 31-42, SEQ ID NO: 8, 58-61, SEQ ID NO: 83 or 84, suitable for use as a probe and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105 suitable for use as a probe combination.

A preferred oligonucleotide composition comprises or consists of
i) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92 suitable for use as a primer;
ii) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15 suitable for use as a primer.
iii) at least one oligonucleotide comprising or consisting essentially of a sequence selected from the group consisting of SEQ ID NO: 3, 9, 23-30, SEQ ID NO: 7, 49-57, SEQ ID NO: 7, 49, 50, 55-57, 73-76, 91, SEQ ID NO: 97-101 suitable for use as a blocker; and
iv) at least one oligonucleotide comprising or consisting essentially of a sequence selected from the group consisting of SEQ ID NO: 4, 31-42, SEQ ID NO: 8, 58-61, SEQ ID NO: 83 or 84, suitable for use as a probe and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105 suitable for use as a probe combination.

A preferred oligonucleotide composition comprises or consists of
a) an oligonucleotide comprising or consisting essentially of a sequence selected from the group consisting of SEQ ID NO: 6, 48, 62-64; and
b) an oligonucleotide comprising or consisting essentially of a sequence selected from the group consisting of SEQ ID NO: 65-72.

A preferred oligonucleotide composition comprises or consists additionally of an oligonucleotide comprising or consisting essentially of a sequence selected from the group consisting of SEQ ID NO: 7, 49, 50, 55-57, 73-76. A preferred oligonucleotide composition comprises or consists additionally of an oligonucleotide comprising or consisting essentially of the sequence of either SEQ ID NO: 83 or SEQ ID NO: 84, or of an oligonucleotide combination comprising or consisting essentially of the sequences of SEQ ID NO: 77 and 78, of SEQ ID NO: 79 and 80, or of SEQ ID NO: 81 and 82.

A preferred oligonucleotide composition comprises or consists of
a) an oligonucleotide comprising or consisting essentially of a sequence selected from the group consisting of SEQ ID NO: 6, 48, 62-64;
b) an oligonucleotide comprising or consisting essentially of a sequence selected from the group consisting of SEQ ID NO: 65-72;
c) an oligonucleotide comprising or consisting essentially of a sequence selected from the group consisting of SEQ ID NO: 7, 49, 50, 55-57, 73-76; and
d) an oligonucleotide comprising or consisting essentially of the sequence of either SEQ ID NO: 83 or SEQ ID NO: 84, or an oligonucleotide combination comprising or consisting essentially of the sequences of either of SEQ ID NO: 77 and 78, of SEQ ID NO: 79 and 80, or of SEQ ID NO: 81 and 82.

A most particularly preferred oligonucleotide composition comprises or consists of
a) an oligonucleotide comprising or consisting essentially of the sequence of SEQ ID NO: 6; and
b) an oligonucleotide comprising or consisting essentially of the sequence of SEQ ID NO: 65.

A further most particularly preferred oligonucleotide composition comprises or consists additionally of an oligonucleotide comprising or consisting essentially of the sequence of SEQ ID NO: 7. A further most particularly preferred oligonucleotide composition comprises or consists additionally of an oligonucleotide combination comprising or consisting essentially of the sequences of SEQ ID NO: 81 and 82.

A most particularly preferred oligonucleotide composition comprises or consists of
a) an oligonucleotide comprising or consisting essentially of the sequence of SEQ ID NO: 6;
b) an oligonucleotide comprising or consisting essentially of the sequence of SEQ ID NO: 65;
c) an oligonucleotide comprising or consisting essentially of the sequence of SEQ ID NO: 7; and
d) an oligonucleotide combination comprising or consisting essentially of the sequences of SEQ ID NO: 81 and 82.

A preferred oligonucleotide composition comprises or consists of
a) an oligonucleotide comprising or consisting essentially of a sequence selected from the group consisting of SEQ ID NO: 6, 44-48 suitable for use as a primer; and
b) an oligonucleotide comprising or consisting essentially of a sequence selected from the group consisting of SEQ ID NO: 5, 43 suitable for use as a primer.

A preferred oligonucleotide composition comprises or consists additionally of an oligonucleotide comprising or consisting essentially of a sequence selected from the group consisting of SEQ ID NO: 7, 49-57 suitable for use as a blocker. A preferred oligonucleotide composition comprises or consists of additionally an oligonucleotide comprising or consisting essentially of a sequence selected from the group consisting of SEQ ID NO: 8, 58-61, suitable for use as a probe.

A preferred oligonucleotide composition comprises or consists of
a) an oligonucleotide comprising or consisting essentially of a sequence selected from the group consisting of SEQ ID NO: 6, 44-48;
b) an oligonucleotide comprising or consisting essentially of a sequence selected from the group consisting of SEQ ID NO: 5, 43;
c) an oligonucleotide comprising or consisting essentially of a sequence selected from the group consisting of SEQ ID NO: 7, 49-57; and
d) an oligonucleotide comprising or consisting essentially of a sequence selected from the group consisting of SEQ ID NO: 8, 58-61.

A most particularly preferred oligonucleotide composition comprises or consists of
a) an oligonucleotide comprising or consisting essentially of the sequence of SEQ ID NO: 5; and
b) an oligonucleotide comprising or consisting essentially of the sequence of SEQ ID NO: 6.

A most particularly preferred oligonucleotide composition comprises or consists additionally of an oligonucleotide comprising or consisting essentially of the sequence of SEQ ID NO: 7.

A most particularly preferred oligonucleotide composition comprises or consists additionally of an oligonucleotide comprising or consisting essentially of the sequence of SEQ ID NO: 8.

A most particularly preferred oligonucleotide composition comprises or consists of
a) an oligonucleotide comprising or consisting essentially of the sequence of SEQ ID NO: 5;
b) an oligonucleotide comprising or consisting essentially of the sequence of SEQ ID NO: 6;
c) an oligonucleotide comprising or consisting essentially of the sequence of SEQ ID NO: 7; and
d) an oligonucleotide comprising or consisting essentially of the sequence of SEQ ID NO: 8.

A preferred oligonucleotide composition comprises or consists of
a) an oligonucleotide comprising or consisting essentially of a sequence selected from the group consisting of SEQ ID NO: 1, 12-15, suitable for use as a primer; and
b) an oligonucleotide comprising or consisting essentially of a sequence selected from the group consisting of SEQ ID NO: 2, 16-22, suitable for use as a primer.

A preferred oligonucleotide composition comprises or consists additionally of an oligonucleotide comprising or consisting essentially of a sequence selected from the group consisting of SEQ ID NO: 3, 9, 23-30, 91, suitable for use as a blocker. A preferred oligonucleotide composition comprises or consists additionally of an oligonucleotide comprising or consisting essentially of a sequence selected from the group consisting of SEQ ID NO: 4, 31-42.

A preferred oligonucleotide composition comprises or consists of
a) an oligonucleotide comprising or consisting essentially of a sequence selected from the group consisting of SEQ ID NO: 1, 12-15;
b) an oligonucleotide comprising or consisting essentially of a sequence selected from the group consisting of SEQ ID NO: 2, 16-22;
c) an oligonucleotide comprising or consisting essentially of a sequence selected from the group consisting of SEQ ID NO: 3, 9, 23-30, 91; and
d) an oligonucleotide comprising or consisting essentially of a sequence selected from the group consisting of SEQ ID NO: 4, 31-42.

A most particularly preferred oligonucleotide composition comprises or consists of
a) an oligonucleotide comprising or consisting essentially of the sequence of SEQ ID NO: 1; and
b) an oligonucleotide comprising or consisting essentially of the sequence of SEQ ID NO: 21.

A most particularly preferred oligonucleotide composition comprises or consists additionally of an oligonucleotide comprising or consisting essentially of the sequence of SEQ ID NO: 3.

A most particularly preferred oligonucleotide composition comprises or consists additionally of an oligonucleotide comprising or consisting essentially of the sequence of SEQ ID NO: 4.

A most particularly preferred oligonucleotide composition comprises or consists of
a) an oligonucleotide comprising or consisting essentially of the sequence of SEQ ID NO: 1;
b) an oligonucleotide comprising or consisting essentially of the sequence of SEQ ID NO: 21;
c) an oligonucleotide comprising or consisting essentially of the sequence of SEQ ID NO: 3; and
d) an oligonucleotide comprising or consisting essentially of the sequence of SEQ ID NO: 4.

A preferred oligonucleotide composition comprises or consists of
a) an oligonucleotide comprising or consisting essentially of the sequence of SEQ ID NO: 92, suitable for use as a primer; and
b) an oligonucleotide comprising or consisting essentially of a sequence selected from the group consisting of SEQ ID NO: 1, 12-15, suitable for use as a primer.

A preferred oligonucleotide composition comprises or consists additionally of an oligonucleotide comprising or consisting essentially of a sequence selected from the group consisting of SEQ ID NO: 9, 23, 24, 91, 97-101, suitable for use as a blocker. A preferred oligonucleotide composition comprises or consists additionally of an oligonucleotide comprising or consisting essentially of a sequence selected from the group consisting of SEQ ID NO: 4, 31-42, suitable for use as a probe, or of an oligonucleotide combination comprising or consisting essentially of a sequence combination selected from the group consisting of SEQ ID NO: 102 and 103 and of SEQ ID NO: 104 and 105, suitable for use as probe combination.

A preferred oligonucleotide composition comprises or consists of
a) an oligonucleotide comprising or consisting essentially of the sequence of SEQ ID NO: 92;
b) an oligonucleotide comprising or consisting essentially of a sequence selected from the group consisting of SEQ ID NO: 1, 12-15;
c) an oligonucleotide comprising or consisting essentially of a sequence selected from the group consisting of SEQ ID NO: 9, 23, 24, 91, 97-101; and
d) an oligonucleotide comprising or consisting essentially of a sequence selected from the group consisting of SEQ ID NO: 4, 31-42, or an oligonucleotide combination is selected, said combination comprising or consisting essentially of a sequence combination selected from the group consisting of SEQ ID NO: 102 and 103 and of SEQ ID NO: 104 and 105.

One aspect of the invention is an oligonucleotide composition. Said oligonucleotide composition comprises or consists of two, three, four or more oligonucleotides comprising or consisting essentially of a sequence selected from the group consisting of SEQ ID NO: 92-96, 31 and of SEQ ID NO: 1, 4, 9, 12-15, 23, 24, 31-42, 91, 92, 97-101, 102-105 and of two three four or more oligonucleotides comprising or consisting essentially of a sequence selected from the group consisting of SEQ ID NO: 6, 7, 48-50, 55-57, 62-84. Preferably, said composition is suitable for performing a combined assay for amplification, preferably for methylation analysis, and most preferably for detecting the presence or absence of a methylation pattern. Preferably, said combined assay is an assay wherein each of the strands of a converted DNA are analyzed. Said conversion is a treatment wherein cytosine is converted to uracil sulfonate or another base having a different binding behavior than cytosine, while methylated cytosine remains unchanged.

A preferred oligonucleotide composition comprises or consists of
a) an oligonucleotide comprising or consisting essentially of the sequence of SEQ ID NO: 92 and an oligonucleotide comprising or consisting essentially of a sequence selected from the group consisting of SEQ ID NO: 6, 44-48; SEQ ID NO: 6, 48, 62-64;
b) an oligonucleotide comprising or consisting essentially of a sequence selected from the group consisting of SEQ ID NO: 1, 12-15, 93 and an oligonucleotide comprising or consisting essentially of a sequence selected from the group consisting of SEQ ID NO: 5, 43; SEQ ID NO: 65-72.

A preferred composition comprises or consists additionally of at least one oligonucleotide comprising or consisting essentially of a sequence selected from the group consisting of SEQ ID NO: 9, 23, 24, 97-101, 94, SEQ ID NO: 7, 49-57; SEQ ID NO: 7, 49, 50, 55-57, 73-76, 91, A preferred composition comprises or consists additionally of (a) at least one oligonucleotide comprising or consisting essentially of a sequence selected from the group consisting of SEQ ID NO: 4, 31-42, SEQ ID NO: 8, 58-61; SEQ ID NO: 83 or 84, and/or (b) at least one oligonucleotide combination comprising or consisting essentially of the sequences of SEQ ID NO: 95 and 96, of SEQ ID NO: 102 and 103, of SEQ ID NO: 104 and 105, and of SEQ ID NO: 81 and 82.

A preferred oligonucleotide composition comprises or consists of
a) an oligonucleotide comprising or consisting essentially of the sequence of SEQ ID NO: 92 and an oligonucleotide comprising or consisting essentially of a sequence selected from the group consisting of SEQ ID NO: 6, 44-48; SEQ ID NO: 6, 48, 62-64;
b) an oligonucleotide comprising or consisting essentially of a sequence selected from the group consisting of SEQ ID NO: 1, 12-15, 93 and an oligonucleotide comprising or consisting essentially of a sequence selected from the group consisting of SEQ ID NO: 5, 43; SEQ ID NO: 65-72;
c) at least one oligonucleotide comprising or consisting essentially of a sequence selected from the group consisting of SEQ ID NO: 9, 23, 24, 97-101, 94, SEQ ID NO: 7, 49-57; SEQ ID NO: 7, 49, 50, 55-57, 73-76, 91; and
d) at least one oligonucleotide comprising or consisting essentially of a sequence selected from the group consisting of SEQ ID NO: 4, 31-42, SEQ ID NO: 8, 58-61; SEQ ID NO: 83 or 84, and/or at least one oligonucleotide combination comprising or consisting essentially of the sequences of SEQ ID NO: 95 and 96, of SEQ ID NO: 102 and 103, of SEQ ID NO: 104 and 105, and of SEQ ID NO: 81 and 82.

A preferred oligonucleotide composition comprises or consists of two, three, four or more oligonucleotides comprising or consisting essentially of a sequence selected from the group consisting of SEQ ID NO: 92-96 and 31 and of two three four or more oligonucleotides comprising or consisting essentially of a sequence selected from the group consisting of SEQ ID NO: 5-8, 43-61. Preferably, said composition is suitable for performing a combined assay for amplification, preferably for methylation analysis, and most preferably for detecting the presence or absence of a methylation pattern. Said combined assay is an assay wherein each of the strands of a converted DNA are analyzed. Said conversion is a treatment wherein cytosine is converted to uracil sulfonate or another base having a different binding behavior than cytosine, while methylated cytosine remains unchanged.

A particular preferred oligonucleotide composition comprises or consists of the oligonucleotides comprising or consisting essentially of the sequence of SEQ ID NO: 92, 93, 5 and 6. A particular preferred oligonucleotide composition comprises or consists additionally of the oligonucleotide comprising or consisting essentially of the sequence of SEQ ID NO: 94, the oligonucleotide comprising or consisting essentially of the sequence of SEQ ID NO: 7, or both.

A particular preferred oligonucleotide composition comprises or consists additionally of the oligonucleotide combination comprising or consisting essentially of the sequences of SEQ ID NO: 95 and 96, the oligonucleotide comprising or consisting essentially of the sequence of SEQ ID NO: 8, or both.

A particular preferred oligonucleotide composition comprises or consists of
a) the oligonucleotides comprising or consisting essentially of the sequence of SEQ ID NO: 92, 93, 5 and 6;
b) the oligonucleotide comprising or consisting essentially of the sequence of SEQ ID NO: 94, the oligonucleotide comprising or consisting essentially of the sequence of SEQ ID NO: 7, or both; and
c) the oligonucleotide combination comprising or consisting essentially of the sequences of SEQ ID NO: 95 and 96, the oligonucleotide comprising or consisting essentially of the sequence of SEQ ID NO: 8, or both.

A preferred oligonucleotide composition comprises or consists of two, three, four or more oligonucleotides comprising or consisting essentially of a sequence selected from the group consisting of SEQ ID NO: 1-4, 9, 12-42, 91 and of two three four or more oligonucleotides comprising or consisting essentially of a sequence selected from the group consisting of SEQ ID NO: 6, 7, 48-50, 55-57, 62-84. Preferably, said composition is suitable for performing a combined assay for amplification, preferably for methylation analysis, and most preferably for detecting the presence or absence of a methylation pattern. Said combined assay is an assay wherein each of the strands of a converted DNA are analyzed. Said conversion is a treatment wherein cytosine is converted to uracil sulfonate or another base having a different binding behavior than cytosine, while methylated cytosine remains unchanged.

A preferred oligonucleotide composition comprises or consists of two, three, four or more oligonucleotides comprising or consisting essentially of a sequence selected from the group consisting of SEQ ID NO: 1-4, 9, 12-42, 91 and of two three four or more oligonucleotides comprising or consisting essentially of a sequence selected from the group consisting of SEQ ID NO: 5-8, 43-61. Preferably, said composition is suitable for performing a combined assay for amplification, preferably for methylation analysis, and most preferably for detecting the presence or absence of a methylation pattern. Said combined assay is an assay wherein each of the strands of a converted DNA are analyzed. Said conversion is a treatment wherein cytosine is converted to uracil sulfonate or another base having a different binding behavior than cytosine, while methylated cytosine remains unchanged.

A particularly preferred oligonucleotide composition comprises or consists of a) an oligonucleotide comprising or consisting essentially of a sequence selected from the group consisting of SEQ ID NO: 1, 12-15, and an oligonucleotide comprising or consisting essentially of a sequence selected from the group consisting of SEQ ID NO: 6, 44-48; SEQ ID NO: 6, 48, 62-64; and of b) an oligonucleotide comprising or consisting essentially of a sequence selected from the group consisting of SEQ ID NO: 2, 16-22 and an oligonucleotide comprising or consisting essentially of a sequence selected from the group consisting of SEQ ID NO: 5, 43; SEQ ID NO: 65-72.

A particularly preferred oligonucleotide composition comprises or consists additionally of at least one oligonucleotide comprising or consisting essentially of a sequence selected from the group consisting of SEQ ID NO: 3, 9, 23-30; SEQ ID NO: 7, 49-57; SEQ ID NO: 7, 49, 50, 55-57, 73-76, 91. A particular preferred oligonucleotide composition comprises or consists additionally of at least one oligonucleotide comprising or consisting essentially of a sequence selected from the group consisting of SEQ ID NO: 4, 31-42; SEQ ID NO: 8, 58-61; SEQ ID NO: 83 or 84, and/or additionally of an oligonucleotide combination comprising or consisting essentially of the sequences of SEQ ID NO: 77 and 78, of SEQ ID NO: 79 and 80, and of SEQ ID NO: 81 and 82.

A particularly preferred oligonucleotide composition comprises or consists of a) an oligonucleotide comprising or consisting essentially of a sequence selected from the group consisting of SEQ ID NO: 1, 12-15, and an oligonucleotide comprising or consisting essentially of a sequence selected from the group consisting of SEQ ID NO: 6, 44-48; SEQ ID NO: 6, 48, 62-64;

b) an oligonucleotide comprising or consisting essentially of a sequence selected from the group consisting of SEQ ID NO: 2, 16-22 and an oligonucleotide comprising or consisting essentially of a sequence selected from the group consisting of SEQ ID NO: 5, 43; SEQ ID NO: 65-72;

c) at least one oligonucleotide comprising or consisting essentially of a sequence selected from the group consisting of SEQ ID NO: 3, 9, 23-30; SEQ ID NO: 7, 49-57; SEQ ID NO: 7, 49, 50, 55-57, 73-76, 91; and d) at least one oligonucleotide comprising or consisting essentially of a sequence selected from the group consisting of SEQ ID NO: 4, 31-42; SEQ ID NO: 8, 58-61; SEQ ID NO: 83 or 84, and/or an oligonucleotide combination comprising or consisting essentially of the sequences of SEQ ID NO: 77 and 78, of SEQ ID NO: 79 and 80, and of SEQ ID NO: 81 and 82.

A most particularly preferred oligonucleotide composition comprises or consists of the oligonucleotides comprising or consisting essentially of the sequence of SEQ ID NO: 1, 21, 5 and 6.

A further most particularly preferred oligonucleotide composition comprises or consists additionally of the oligonucleotide comprising or consisting essentially of the sequence of SEQ ID NO: 3, the oligonucleotide comprising or consisting essentially of the sequence of SEQ ID NO: 7, or both. A further most particularly preferred oligonucleotide composition comprises or consists additionally of the oligonucleotide comprising or consisting essentially of the sequence of SEQ ID NO: 4, the oligonucleotide comprising or consisting essentially of the sequence of SEQ ID NO: 8, or both.

A most particularly preferred oligonucleotide composition comprises or consists of a) the oligonucleotides comprising or consisting essentially of the sequence of SEQ ID NO: 1, 21, 5 and 6;

b) the oligonucleotide comprising or consisting essentially of the sequence of SEQ ID NO: 3, the oligonucleotide comprising or consisting essentially of the sequence of SEQ ID NO: 7, or both; and c) the oligonucleotide comprising or consisting essentially of the sequence of SEQ ID NO: 4, the oligonucleotide comprising or consisting essentially of the sequence of SEQ ID NO: 8, or both.

Kits

One aspect of the invention is a kit for providing DNA. Preferably, said DNA is provided for methylation analysis, in particular for detecting the presence of a methylation pattern. The said kit comprises (a) SiMAG/FK-Silanol beads (Chemicell, Germany, Article Number 1101-1 or 1101-5) or beads of the chemagic Viral DNA/RNA Kit special (Chemagen, Germany, Article Number 1002) for isolation of genomic DNA and/or for purification of treated DNA, said treated DNA being a DNA wherein cytosine is converted to uracil sulfonate or another base having a different binding behavior than cytosine, while methylated cytosine remains unchanged during said treatment;

(b) a reagent or bisulfite reagent for treating genomic DNA, wherein cytosine is converted to uracil sulfonate or another base having a different binding behavior than cytosine, while methylated cytosine remains unchanged.

A preferred variant of the kit comprises further a manual or description for performing a method of the invention. A preferred variant of the kit comprises further one or more radical scavengers for the treatment of genomic DNA. Such kind of radical scavengers are known from the art (see for example WO 01/98528, WO 2005/038051, WO 2006/103111, and WO 2006/113770). Particularly preferred are 6-hydroxy-2,5, 7,8-tetramethyl-chroman-2-carboxylic acid, gallic acid, or derivatives of the said. A preferred variant of the kit comprises further an organic solvent. Suitable organic solvents are known from the art (WO 2005/038051, WO 2006/103111, and WO 2006/113770). Preferred are n-alkylene glycol compounds, particularly their dialkyl ethers, and especially diethylene glycol dimethyl ether (DME). A preferred variant of the kit comprises further buffers and solutions suitable for performing DNA isolation, bisulfite treatment, desulfonation, purification of bisulfite treated DNA, and amplification, in particular PCR. A person skilled in the art is aware of suitable buffers and solutions. Such buffers and solutions are for example, but not limited to in parts described in WO 2005/038051, WO 2006/103111, and WO 2006/113770.

A particularly preferred variant of the kit comprises (a) SiMAG/FK-Silanol beads (Chemicell, Germany, Article Number 1101-1 or 1101-5) or beads of the chemagic Viral DNA/RNA Kit special (Chemagen, Germany, Article Number 1002) for isolation of genomic DNA and/or for purification of treated DNA, said treated DNA being a DNA wherein cytosine is converted to uracil sulfonate or another base having a different binding behavior than cytosine, while methylated cytosine remains unchanged during said treatment;

(b) a reagent or bisulfite reagent for treating genomic DNA, wherein cytosine is converted to uracil sulfonate or another base having a different binding behavior than cytosine, while methylated cytosine remains unchanged.

(c) one or more radical scavengers for the treatment of genomic DNA, in particular 6-hydroxy-2,5,7,8-tetramethyl-chroman-2-carboxylic acid or gallic acid; and (d) an organic solvent, in particular DME.

Preferably the kit comprises also a manual or description for performing the method of the invention. Preferably the kit comprises also buffers and solutions suitable for performing DNA isolation, bisulfite treatment, desulfonation, purification of bisulfite treated DNA, and amplification, in particular PCR.

One aspect of the invention is a kit, comprising a) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92;

b) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15.

A preferred variant of the kit comprises or consists additionally of at least one oligonucleotide comprising or consisting essentially of a sequence selected from the group consisting of SEQ ID NO: 3, 9, 23-30, 91, SEQ ID NO: 7, 49-57, SEQ ID NO: 7, 49, 50, 55-57, 73-76, SEQ ID NO: 97-101. A preferred variant of the kit comprises or consists additionally of at least one oligonucleotide comprising or consisting essentially of a sequence selected from the group consisting of SEQ ID NO: 4, 31-42, SEQ ID NO: 8, 58-61, SEQ ID NO: 83 or 84, and/or at least one oligonucleotide combination comprising or consisting essentially of the sequences of either SEQ ID NO: 77 and 78, of SEQ ID NO: 79 and 80, of SEQ ID NO: 81 and 82, of SEQ ID NO: 102 and 103, or of SEQ ID NO: 104 and 105. A preferred variant of the kit comprises or consists additionally of a polymerase, preferably a heat stable polymerase.

Preferably, the inventive kit is in particular useful for amplification, preferably for methylation analysis, and most preferably for detecting the presence of a methylation pattern.

A particularly preferred kit comprises or consists of a) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92;

b) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15;

c) at least one oligonucleotide comprising or consisting essentially of a sequence selected from the group consisting of SEQ ID NO: 3, 9, 23-30, 91, SEQ ID NO: 7, 49-57, SEQ ID NO: 7, 49, 50, 55-57, 73-76, SEQ ID NO: 97-101;

d) at least one oligonucleotide comprising or consisting essentially of a sequence selected from the group consisting of SEQ ID NO: 4, 31-42, SEQ ID NO: 8, 58-61, SEQ ID NO: 83 or 84, and/or at least one oligonucleotide combination comprising or consisting essentially of the sequences of either SEQ ID NO: 77 and 78, of SEQ ID NO: 79 and 80, of SEQ ID NO: 81 and 82, of SEQ ID NO: 102 and 103, or of SEQ ID NO: 104 and 105; and e) a heat stable polymerase.

A particularly preferred kit comprises or consists of a) at least one oligonucleotide comprising or consisting essentially of a sequence selected from the group consisting of SEQ ID NO: 1, 12-15, SEQ ID NO: 6, 44-48, SEQ ID NO: 6, 48, 62-64, SEQ ID NO 92, suitable for use as primer;

b) at least one oligonucleotide comprising or consisting essentially of a sequence selected from the group consisting of SEQ ID NO: 2, 16-22, SEQ ID NO: 5, 43, SEQ ID NO: 65-72, SEQ ID NO: 1, 12-15, suitable for use as primer;

c) at least one oligonucleotide comprising or consisting essentially of a sequence selected from the group consisting of SEQ ID NO: 3, 9, 23-30, 91, SEQ ID NO: 7, 49-57, SEQ ID NO: 7, 49, 50, 55-57, 73-76, SEQ ID NO: 97-101, suitable for use as blocker;

d) at least one oligonucleotide comprising or consisting essentially of a sequence selected from the group consisting of SEQ ID NO: 4, 31-42, SEQ ID NO: 8, 58-61, SEQ ID NO: 83 or 84, suitable for use as probe and/or at least one oligonucleotide combination comprising or consisting essentially of the sequences of either SEQ ID NO: 77 and 78, of SEQ ID NO: 79 and 80, of SEQ ID NO: 81 and 82, of SEQ ID NO: 102 and 103, or of SEQ ID NO: 104 and 105, suitable for use as probe combination; and e) a heat stable polymerase.

A particularly preferred kit may also comprise reagents, solutions, and devices for performing an amplification reaction. For example, but not limited to it, such reagents, solutions, and devices are $MgCl_2$, dNTPs, dyes, fluorescent dyes, PCR buffer, UNG (uracil-DNA-glycosylase), and a manual or description for performing a method of the invention.

Utility of the Method of the Invention, of the Oligonucleotide or Oligonucleotide Composition of the Invention, or the Kit of the Invention The method of the invention, the oligonucleotides or oligonucleotide compositions of the invention or the kit of the invention have in particular diagnostic utility for cellular proliferative disorders, in particular for the detection or diagnosis of colon carcinoma or liver carcinoma.

The present invention enables diagnosis of events which are disadvantageous to patients or individuals in which important epigenetic parameters within the Septin 9 gene are used as markers. Said parameters may be compared to another set of epigenetic parameters, the differences serving as the basis for a diagnosis of events which are disadvantageous to patients or individuals.

More specifically the present invention enables the screening of at-risk populations for the early detection of cancers, most preferably colorectal carcinomas and liver carcinomas. Neoplastic cellular proliferative disorders, most particularly carcinomas, present a methylated Septin 9 gene, as opposed to normal tissues which do not.

Specifically, the present invention provides diagnostic cancer assays based on measurement of differential methylation of CpG dinucleotides of the Septin 9 gene (SEQ ID NO: 85; in particular SEQ ID NO: 86, 87 (nucleotide 9295902 to nucleotide 9295840 of GenBank Accession Number NT_010641.15) and SEQ ID NO: 88 (nucleotide 9295830 to nucleotide 9295894 of GenBank Accession Number NT_010641.15). Typically, this involves (a) obtaining a sample from a subject; (b) performing one of the embodiments of the inventive method described herein to determine the methylation of the Septin 9 gene, preferably of the sequence SEQ ID NO; 85, and more preferably of SEQ ID NO: 86, 87 and/or 88 derived from the sample, relative to a control sample, or a known standard; and (c) making a diagnosis based at least in parts thereon.

Embodiments of the inventive method which comprise oligonucleotides comprising or consisting essentially of a sequences selected from the group of SEQ ID NO: 1-30, 32-84, 91, 97-105, particularly from the group of ID NO: 1-8, are useful for assessing the methylation of the Septin 9 gene i.e. for the detecting of the presence of methylation of CpG dinucleotides covered by the amplification assays as defined by the herein described embodiments of the inventive method. Correspondingly, variants of the inventive oligonucleotide or oligonucleotide compositions comprising or consisting essentially of sequences selected from the group of SEQ ID NO: 1-84, 91-105 are useful for assessing the methylation of the Septin 9 gene i.e. for the detecting of the presence of methylation of CpG dinucleotides covered by the amplification assays as defined by the herein described embodiments of the inventive method. Correspondingly, the herein described variants of the inventive kit are useful for assessing the methylation of the Septin 9 gene i.e. for the detecting of the presence of methylation of CpG dinucleotides covered by the amplification assays as defined by the herein described embodiments of the inventive method. Said CpG dinucleotides are considered to be methylated, wherein an amplificate is detected by suitable means for example but not limited by means of one or more of the herein described probes or probe combinations. Said CpG dinucleotides are considered to be unmethylated, wherein no amplificate is detected by suitable means for example but not limited by means of one or more of the herein described probes or probe combinations.

The described embodiments of the inventive method, oligonucleotide, oligonucleotide composition, or kit are also in particular useful for the diagnosis of cellular proliferative disorders, most preferably colorectal carcinoma and liver carcinoma.

The methods, oligonucleotides, oligonucleotide compositions and kits disclosed herein are preferably used and applicable for diagnosis, classification and/or prognosis of adverse events for patients or individuals, whereby these adverse events belong to at least one of the following categories:

undesired drug interactions; cancer diseases; cellular proliferative disorders; colon carcinoma; liver carcinoma; CNS malfunctions; damage or disease; symptoms of aggression or behavioral disturbances; clinical; psychological and social consequences of brain damages; psychotic disturbances and personality disorders; dementia and/or associated syndromes; cardiovascular disease, malfunction or damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The methods, oligonucleotides, oligonucleotide compositions and kits disclosed herein are preferably used and applicable for distinguishing cell types and/or tissues and/or for investigating cell differentiation.

The methods, oligonucleotides, oligonucleotide compositions and kits disclosed herein are preferably used and applicable for the discovery a methylation marker, wherein the marker is indicative for adverse events for patients or individuals, whereby these adverse events belong to at least one of the following categories:

undesired drug interactions; cancer diseases; cellular proliferative disorders; colon carcinoma; liver carcinoma; CNS malfunctions; damage or disease; symptoms of aggression or behavioral disturbances; clinical; psychological and social consequences of brain damages; psychotic disturbances and personality disorders; dementia and/or associated syndromes; cardiovascular disease, malfunction or damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

All herein cited references are incorporated by reference to their entirety.

DEFINITIONS

In particular aspects, the term "essentially consisting" or the term "consisting essentially" refers to but is not limited to, DNA sequences which are identical, or share a homology in the range of 75-100%. The term is used to reflect the naturally occurring variance of the genome of individual subjects. Alternatively, said terms as used herein for describing a nucleic acid sequence by reference to a SEQ ID NO: shall encompass a sequence that differs from said SEQ ID NO: by no more than 1, 2, 3, 4, 5, 6, 7, 8, 9, 10, 11, 12, 13, 14 or 15 bases.

In particular aspects, the term "oligonucleotide" refers to, but is not limited to, DNA-oligonucleotides, RNA-oligonucleotides, PNA-oligomers or derivatives thereof such as for example but not limited to LNA-oligonucleotides.

In particular aspects, the term "methylation status" refers to, but is not limited to, the presence or absence of methylation of one nucleotide. Thereby said nucleotide has the ability of being methylated or being non-methylated. A methylation status can be quantified, wherein a it is considered over more than one nucleic acid.

In particular aspects, the term "methylation pattern" refers to, but is not limited to, the presence or absence of methylation of two or more CpG dinucleotides. Said one or more nucleotides are comprised in a single nucleic acid molecule. They have the ability of being methylated or being non-methylated. A methylation pattern can be quantified, wherein it is considered over more than one nucleic acid. In this regard, two or more CpG dinucleotides are considered as being co-methylated when said two or more CpG dinucleotides show the same methylation behavior.

In particular aspects, the term "methylation analysis" refers to, but is not limited to, the analysis of the presence or absence of one or more methylation pattern. Synonymously, it refers to, but is not limited to, the analysis of the presence of absence of methylation of one or more cytosines.

In particular aspects, the term "CpG dinucleotide" refers to, but is not limited to, the sequence 5'-CG-3' in a nucleic acid, in particular in a DNA, and most particular in a genomic DNA.

In particular aspects, the term "primer" refers to, but is not limited to, an oligonucleotide that is able to be elongated.

In particular aspects, the term "blocker" refers to, but is not limited to, an oligonucleotide that is able to prevent or at least reduce the likelihood of a primer elongation or an amplification reaction.

In particular aspects, the term "probe" refers to, but is not limited to, either an oligonucleotide suitable for the detection of an elongated primer or of an amplificate or to an oligonucleotide of the reverse complementary sequence of said suitable oligonucleotide.

In particular aspects, the term "probe combination" refers to, but is not limited to, a set of two oligonucleotides wherein said two oligonucleotides together are suitable for the detection of an elongated primer or of an amplificate. The term also refers but is not limited to the set of oligonucleotides that are reverse complementary to the sequence of said suitable set of oligonucleotides.

In particular aspects, the term "combined assay" refers to, but is not limited to, a compound amplification reaction that comprises or consists of two individual amplification reactions. Preferably, one of the said individual amplification reactions is located on the sense strand while the other is located on the antisense strand. However both of the said individual amplification reactions refer to the same genomic site.

EXAMPLES

Example 1

Comparison of Beads and Kits for the Purification of Genomic DNA from Remote Samples (e.g. Plasma Samples)

Blood plasma samples were purchased from Cliniqa (San Marcos, Calif., USA; Article Number 1503). DNA was extracted from 5 ml of plasma by means of kits and beads listed in Table 1 following the protocols supplied by the vendors. Where protocols were designed for lower volumes, parallel extractions were performed, the sample combined and the yield determined for 5 ml. Yield calculations were determined by comparison with the beads of the MagNA Pure LC Total Nucleic Acid Kit, Large Volume (Article Number 03264793001) as a standard. Table 1 shows the yield (=recovery in %) of genomic DNA as determined by CFF1 quantification assay. The CFF1 assay was performed as described in WO 2007/039101. The yield calculations were derived from multiple experiments.

Table 1 overview of beads and kits tested for purification of genomic DNA from plasma samples.

| Bead/Kit | Manufacturer | Yield (=recovery in %) |
| --- | --- | --- |
| Beads of the MagNA Pure LC Total Nucleic Acid Kit, Large Volume (Article Number 03264793001) | Roche Diagnostics Corporation | 100% |
| Zymobeads 1 ml (Article Number ZY D3004-3-1) | Zymo Research Corporation | 86% |
| Beads of the MagaZorb DNA Isolation Kit, 200 preps (Article Number 100164-976) | Cortex Biochem Inc. | 59% |
| SiMAG/MPN-Silanol Beads (no Article Number available) | Chemicell GmbH | 0% |
| SiMAG/FK-Silanol Beads (Article Number 1101-1 or 1101-5) | Chemicell GmbH | 100% |
| SiMAG/NK-Silanol Beads (no Article Number available) | Chemicell GmbH | 74% |
| SiMAG/NH-Silanol Beads (no Article Number available) | Chemicell GmbH | 29% |
| SiMAG/TH-Silanol Beads (no Article Number available) | Chemicell GmbH | 29% |
| Beads of the MagneSil ® Genomic Kit, Large Volume System (Article Number A4080) | Promega Corporation | 32% |
| Beads of the GeneCatcher gDNA 3-10 ml Blood Kit (Article Number CS21110) | Invitrogen Corporation | 19% |
| Beads of the chemagic Viral DNA/RNA Kit special (Article Number 1002) | Chemagen Biopolymer Technolgie Aktiengesellschaft | 179% |

-continued

| Bead/Kit | Manufacturer | Yield (=recovery in %) |
| --- | --- | --- |
| Lumigen magnetic beads (no Article Number available) | Lumigen Inc. | 0% |

Example 2

Comparison of Beads and Kits for Purification of Bisulfite Treated DNA 100 ng of a 1:1 mixture of high molecular weight and low molecular weight DNA of bisulfite treated DNA containing uracil-sulfonate and not uracil were purified with different beads according to the recommendations of the manufactures. Table 2 shows the yield (=recovery) of bisulfite treated DNA as determined by CFF1 quantification assay. The CFF1 assay was performed as described in WO 2007/039101.

Table 2 overview of beads tested for purification of bisulfite treated DNA.

| Bead/Kit | Manufacturer | Yield (=recovery in %) |
| --- | --- | --- |
| Beads of the ChargeSwitch Total RNA Cell Kit (Article Number CS14010) | Invitrogen Life Technologies | 0 |
| Beads of the CST Forensic DNA Purification Kit (Article Number 11200 C) | DNA Research Innovations Ltd. | 0 |
| ZymoBeads ™ (Article Number D3004-3-4) | Zymo Research Corporation | 35-50 |
| SiMAG/FK-Silanol Beads (Article Number 1101-1 or 1101-5) | Chemicell GmbH | 65-75 |
| Beads of the chemagic Viral DNA/RNA Kit special (Article Number 1002) | Chemagen Biopolymer Technolgie Aktiengesellschaft | 80-90 |
| MagNA Pure Compact Nucleic Acid Isolation Kit (I) Large Volume (Article Number 3310515) | Roche Diagnostics Corporation | 10-15 |

Example 3

Isolation of Genomic DNA from Remote Samples (Blood)

A) Isolation by Means of Beads of the Chemagic Viral RNA/DNA Kit (Chemagen Biopolymer-Technologie AG, Germany, Article Number 1002)—Protocol I Plasma was collected as described in WO 2006/113770. In brief, blood was drawn in 10 ml EDTA plasma tubes using the vacutainer system. Tubes were centrifuged at 1500×g for 10 min, the supernatant was transferred to a new tube and centrifuged a second time at 1500×g for 10 min. The supernatant is the plasma for further use (4-5 ml).

For DNA isolation, 5 ml of the Lysis Buffer 1, 7 µl poly-A RNA and 30 µl of Proteinase K solution were added to the plasma samples (all adjusted to 5 ml). Samples were incubated at 56° C. for 5 min. Thereafter 100 µl of magnetic beads (Article number 1002) and 15 ml of Binding Buffer 2 were added. In order to keep the beads in suspension by gentle agitation, the samples were place on a rotary mixer at room temperature for about 10 min to allow the binding of DNA to the beads. Magnetic beads were separated by placing the reaction tube in a magnetic stand and discarding the plasma/lysis buffer mixture. Beads were washed three times with 3 ml of Wash Buffer 3, before the were resuspended in 1 ml of Wash Buffer 4, and transferred to 1.7 ml micro-centrifuge tubes. Beads were separated on a magnetic stand, the wash buffer was poured off and the beads were dried at 56° C. After addition of 100 μl Elution Buffer 5, the suspension is incubated for 15 min on the thermomixer at 65° C. After separation of the beads, the elution buffer containing the genomic DNA was recovered. (All reagents were supplied by the chemagic Viral RNA/DNA kit).

B) Isolation by Means of the SiMAG/FK-Silanol Beads (Chemicell GmbH, Germany, Article Number 1101-1 or 1101-5)

The following solutions and buffers were prepared:

Lysis Buffer:
120 g Guanidinium Isothiocyanate; 100 ml 0.1 mol/l Tris-HCl pH6.4 (subsequently); 22 ml 0.2 mol/l EDTA pH 8.0; 2.6 g Triton X-100. (The dissolution of Guanidinium Isothiocyanate was facilitate by heating in a 60° C. water bath under continuous agitation.)

Wash Buffer 1:
120 g Guanidinium Isothiocyanate; 100 ml 0.1 mol/l Tris-HCl pH6.4; dilute with 100% Ethanol to 25% Ethanol.

Wash Buffer 2:
50% EtOH

Proteinase K solution (as provided by chemagic Viral RNA/DNA kit (Chemagen Biopolymer-Technologie AG, Germany, Article Number 1002)

Plasma was collected as described in WO 2006/113770. In brief, blood was drawn in 10 ml EDTA plasma tubes using the vacutainer system. Tubes were centrifuged at 1500×g for 10 min, the supernatant was transferred to a new tube and centrifuged a second time at 1500×g for 10 min. The supernatant is the plasma for further use (4-5 ml).

For DNA isolation, 5 ml of the Lysis Buffer, 100 μl of Proteinase K solution and 100 μl of Si-MAG/FK-Silanol beads (Chemicell GmbH, Germany; Article number 1101-1 or 1101-5) were added to the plasma samples (all adjusted to 5 ml). Samples were gently inverted 5 times to mix and then placed on a shaking platform (100 rpm) at 56° C. for 20 min. After separation of the magnetic SiMAG/FK-Silanol beads by means of a magnetic stand, the beads were washed with 1 ml Wash Buffer 1. During this step, the beads were transferred into 1.5 ml micro-centrifuge tubes. Subsequently the beads were washed twice with 1 ml Wash Buffer 2. Finally, the beads were air-dried at 56° C. for 5 min, before they were resuspended in 50 μl of Elution Buffer, in this case water. The mixture is incubated a thermomixer (1000 rpm) at 65° C. for 15 min. After separation of the beads, the DNA in Elution Buffer is obtained. The elution step is repeated a second time. The two elution volumes of recovered genomic DNA are then combined.

Example 4

Bisulfite Treatment of Genomic DNA Isolated from Remote Samples (Plasma) by Means of the Beads of the Chemagic Viral RNA/DNA Kit or by Means of the SiMAG/FK-Silanol Beads Genomic DNA was subjected to bisulfite treated, the said DNA being isolated from remote samples (blood) by means of the beads of the chemagic Viral RNA/DNA kit or by means of the SiMAG/FK-Silanol beads as described in Example 2.

For bisulfite treatment the following equipment, materials and chemicals were needed:

thermo cycler (Eppendorf mastercycler)
Eppendorf Micro-centrifuge 5417C (or any centrifuge capable of up to 14.000×g)
swim stands for water bath, sizes for 2 ml tubes and 15 ml Falcon tubes
pipettors for volumes of 100 μl and 1000 ηl
pipet tips (100 μl, 1000 μl)
0.5 ml safelock tubes (Eppendorf)
15 ml and 50 ml tubes (Falcon)
sodium bisulfite ($Na_2S_2O_5$, molecular weight 190.1 g/mol, Merck Article Number 1.06528.0500)
sodium sulfite, anhydrous ($Na_2SO_3$, molecular weight 126.04 g/mol, Fluke Article Number 71988)
$ddH_2O$ (molecular biology grade, Fluke Article Number 95284)
diethyleneglycoldimethylether (DME, Merck Article Number 8.02934.0250)
6-hydroxy-2,5,7,8-tetramethylchroman-2-carboxylic acid (molecular weight 250.29 g/mol, Aldrich Article Number 23,881-3)

The following solutions were prepared. They were sufficient for 25 reactions.

Bisulfite solution: 4.71 g Sodium disulfite and 1.13 g sodium sulfite were dissolved by adding 10 ml $ddH_2O$. This resulted in a solution having 4.9 mol/l hydrogen sulfite (the active reagent for bisulfite treatment). If the need has been, the pH of the solution was adjusted by means of 0.2 mol/l NaOH to be in the range between 5.4 and 5.5. In order to dissolve the salts completely, the mixture may have been mixed vigorously and heated to 50° C.

DME-radical scavenger solution: 188 mg of 6-hydroxy-2, 5,7,8-tetramethyl-chroman-2-carboxylic acid were dissolved in 1.5 ml DME. In order to ensure that no un-dissolved particles remain, the mixture was vigorously mixed.

General Remarks:
This procedure was applied to a single sample or to many samples in parallel.
Best results were obtained wherein the bisulfite solution and the DME-radical scavenger solution were prepared freshly Procedure:
190 μl of the said prepared bisulfite solution and 30 μl of the said prepared DME-radical scavenger solution were added to the genomic DNA to be bisulfite treated (DNA from example 2 provided in 100 μl of elution buffer). The total volume of the reaction mixture was 320 μl. Subsequent to vigorous agitation, the reactions mixtures were subjected to the following temperature profile in an Eppendorf mastercycler: 5 min 99° C., 25 min 50° C., 5 min 99° C., 1 h 25 min 50° C., 5 min 99° C., 4 h 55 min 50° C. (temperature of the cycler's lid was set to 115° C.; tube size was 0.5 ml; selected volume in mastercycler software: 100 μl)

Example 5

Purification of Bisulfite Treated DNA of Example 4

(A) Purification by Means of Beads of the Chemagic Viral RNA/DNA Kit (Chemagen Biopolymer-Technologie AG, Germany, Article Number 1002)

The treated reaction mixtures (each 320 µl) of Example 4 were transferred to 2 ml safelock tubes. Subsequently, 1 µl of a 500 ng/µl Poly-A Binding Buffer solution, 1.5 ml of Binding Buffer and 10 µl of beads of the chemagic Viral RNA/DNA kit (Article number 1002) were added. The mixtures were incubated for 60 min at room temperature upon agitation. The beads being magnetic were separated by placing the tube into a magnetic rack. The supernatant was removed. Residual liquid was removed by a short centrifugation and subsequently placing the tube back in the magnetic rack. The beads were washed with 300 µl of Wash buffer 2, and subsequently with 300 µl of 70% ethanol. After a short centrifugation and placing the tube back into the magnetic rack, residual 70% ethanol was removed. The beads were dried by incubating the opened tubes at 55° C. for 10 min. In order to elute the DNA from the beads, 50 µl of 10 mmol/l Tris pH 7.2 were added. The mixture was incubated for 15 min at 55° C. upon agitation (1000 rpm). After a short centrifugation, the beads were separated by placing the tubes into a magnetic rack. The supernatant was removed containing the purified bisulfite treated DNA. The said DNA was subsequently analyzed for example by not limited to by the methods described in Example 6.

(B) Purification by Means of SiMAG/FK-Silanol Beads (Chemicell GmbH, Germany, Article Number 1101-1 or 1101-5)

The following buffers and solutions were prepared:
BL-Buffer: 120 g of guanidinium-thiocyanate (molecular weight 118.2 g/mol) were dissolved in 100 ml of 0.1 mol/l Tris-HCl pH 6.4.
Bead suspension: The buffer wherein the SiMAG/FK-Silanol beads (Chemicell GmbH (Article Number 1101-1 or 1101-5) are delivered was exchanged by BL-Buffer by means of a magnetic separator. One part of SiMAG/FK-Silanol beads in BL-buffer was diluted by 11 parts of ethanol.
Wash Buffer 1: one part of BL-Buffer was diluted by four parts of ddH$_2$0 and 30 ml of the diluted BL-Buffer were mixed with 70 ml of ethanol resulting in Wash Buffer 1.
Wash Buffer 2: 80% Ethanol
poly A solution: poly A was dissolved in water resulting in a final concentration of 5 ng/µl poly A The treated reaction mixtures (each 320 µl) of Example 4 were transferred to 2 ml safelock tubes. Each mixture was treated as described in the following. To the reaction mixture, 600 µl of BL-Buffer and 600 µl of bead suspension were added. After agitation, the mixture is incubated for 60 min at room temperature upon gently further agitation. The beads were separated by placing the tube into a magnetic separator. After removal of the supernatant, the beads were washed by addition of 1 ml of Wash Buffer 1, the beads were separated again by means of the magnetic separator and the supernatant was removed. Thereafter the beads were washed by means of 500 µl Wash Buffer 2, short vigorously agitation, separation of beads by means of magnetic separator and removal of the supernatant. The said washing step with 500 µl Wash Buffer 2 was repeated. Finally the beads were dried by incubating the opened tube for 5 min at 56° C. For elution, 75 µl of poly A solution were added to the beads, the mixture shortly vigorously agitated, and the mixture incubated for 15 min at 70° C. After separation of the beads by means of a magnetic separator, the supernatant containing the purified bisulfite treated DNA was transferred into a new tube. The said DNA was subsequently analyzed for example by not limited to by the methods described in Example 6.

Example 6

Detection of Methylated Sequences of the Septin 9 Gene by Amplification of Bisulfite Converted Sequences of the Forward and Reverse Strand of the Original Genomic DNA in a Duplex PCR DNA fragmentation is many times limiting the sensitivity of the methylation analysis of samples, in particular wherein DNA is already highly fragmented in the original sample. Examples for such samples are body fluid samples like blood, stool, urine, branchial lavage or histological samples like formalin-fixed samples. During bisulfite treatment the DNA is further fragmented resulting in very short fragments in average. This example demonstrates that very small fragments (up to length of 65 nucleotides) are sufficient for the methylation analysis of the septin 9 gene by means of a duplex PCR or a single PCR.

In this example methylated bisulfite converted DNA of the septin 9 gene was amplified using a duplex HeavyMethyl PCR and a referring single HeavyMethyl PCR. The example demonstrates the advantage of the duplex PCR over the single PCR by the shown higher detection rate of low copy number samples. This can be explained by the two times higher theoretical number of template DNA being capable of being amplified, because the duplex PCR uses both bisulfite converted strands of the original DNA as template, whereas the single PCR is only based on either bisulfite or bisulfite 2 strand of the Septin 9 gene. To achieve this the following steps were carried out:

Human genomic DNA from peripheral blood lymphocytes (Roche Diagnostics, Penzberg Germany) were adjusted to a concentration of 0.2 ng/µl. This solution was used to dilute universal methylated human DNA (GpGenome™ Universal Methylated DNA, Chemicon International, Temecula USA) to final concentrations of 0.75 pg/µl and 0.375 pg/µl. 100 µl of each dilution and the solution without methylated DNA were bisulfite treated in 30 replicates. In all 90 different samples were prepared. For this 100 µl of each sample were applied a the bisulfite conversion reaction as previously described (see for example WO2005036051). Each sample was eluted in 50 µl water. After desalting and purification the success of the bisulfite conversion was confirmed by a bisulfite DNA specific reference PCR as previously described (EP05075404). Afterwards 10 µl of each samples was used as template in the duplex PCR and in the single PCR. The reaction mixtures for the duplex HeavyMethyl PCR contained:

10 µl of template DNA
12.5 µl Quantitect Multiplex NoROX PCR Kit (Qiagen, Hilden Germany)
0.3 µmol/l forward primer PCR1 (SEQ ID NO: 1, Biomers.net GmbH Germany)
0.9 µmol/l reverse primer PCR1 (SEQ ID NO: 21, Biomers.net GmbH Germany)
1.0 µmol/l blocker oligonucleotide PCR1 (SEQ ID NO: 3, Biomers.net GmbH Germany)
0.1 µmol/l probe PCR1 (SEQ ID NO: 4, Biomers.net GmbH Germany)
0.3 µmol/l forward primer PCR2 (SEQ ID NO: 5, Biomers.net GmbH Germany)
0.3 µmol/l reverse primer PCR2 (SEQ ID NO: 6, Biomers.net GmbH Germany)
1.0 µmol/l blocker oligonucleotide PCR2 (SEQ ID NO: 7, Biomers.net GmbH Germany)
0.1 µmol/l probe PCR2 (SEQ ID NO: 8, Biomers.net GmbH Germany)

The assay was performed in the LightCycler LC480 (Roche Diagnostics Penzberg Germany) according to the following temperature-time-profile:
activation: 30 min at 95° C.
50 cycles: 10 sec at 95° C.
30 sec at 56° C.

The samples were also analyzed using the single Septin 9 HeavyMethyl PCR, which refers to the PCR2 of the duplex PCR. The reaction mixtures for the single PCR contained:
10 µl of template DNA
12.5 µl Quantitect Multiplex NoROX (Qiagen, Hilden Germany)
0.3 µmol/l forward primer PCR2 (SEQ ID NO: 5, Biomers.net GmbH Germany)
0.3 µmol/l reverse primer PCR2 (SEQ ID NO: 6, Biomers.net GmbH Germany)
1.0 µmol/l blocker oligonucleotide PCR2 (SEQ ID NO: 7, Biomers.net GmbH Germany)
0.1 µmol/l probe PCR2 (SEQ ID NO: 9, Biomers.net GmbH Germany)

The assay was performed in the LightCycler LC480 (Roche Diagnostics Penzberg Germany) according to the following temperature-time-profile:
activation: 30 min at 95° C.
50 cycles: 10 sec at 95° C.
30 sec at 56° C.

The primers of PCR1 (SEQ ID NO: 1 and SEQ ID NO: 21) amplify a fragment of 63 bp of the Septin 9 gene (SEQ ID NO: 10. nucleotide 9295902 to nucleotide 9295840 of GenBank Accession Number NT_010641.15). The primers of PCR2 (SEQ ID NO: 5 and SEQ ID NO: 6) amplify a fragment of 65 bp of the Septin 9 gene (SEQ ID NO: 11. nucleotide 9295830 to nucleotide 9295894 of GenBank Accession Number NT_010641.15). The detection was carried out during the annealing phase at 56° C. In the duplex reaction PCR1 was specifically detected a the channel 533 nm (filter setup 483-533), whereas PCR2 was specifically detected at the channel 610 nm (filter setup 558-610). The single PCR was detected a the channel 533 nm (filter setup 483-533), because the probe dye was changed from TexasRed to FAM for the single reaction (SEQ ID NO: 8). The crossing points (CP) were calculated according to the "second derivative maximum" method by means of the LightCycler 480 software.

Figure 2:
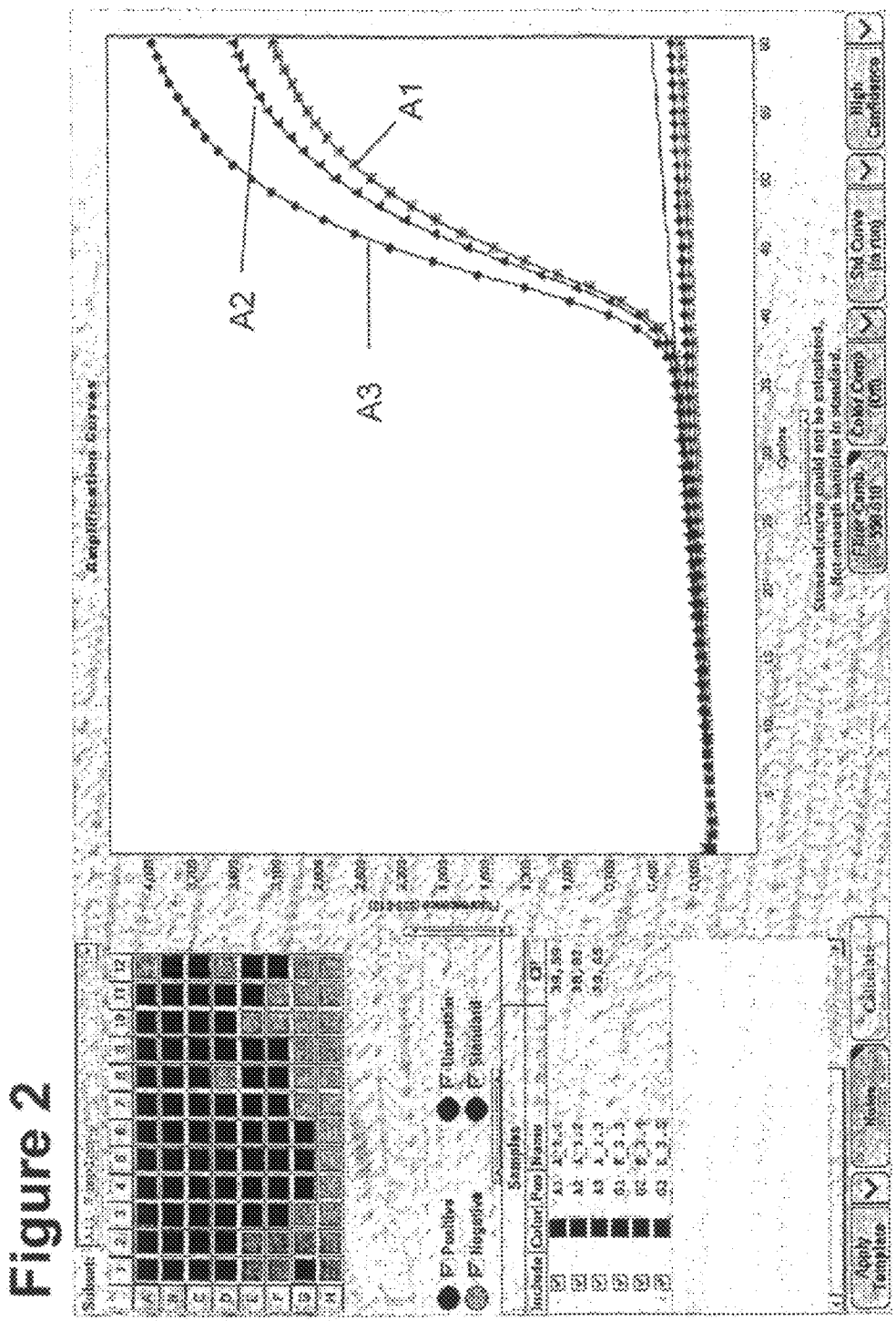
FIG. 2: Representative amplification curves of 6 samples analyzed by the Septin 9 duplex HeavyMethyl PCR. The signals obtained in channel 610 nm is specific for the PCR2.
Figure 3:
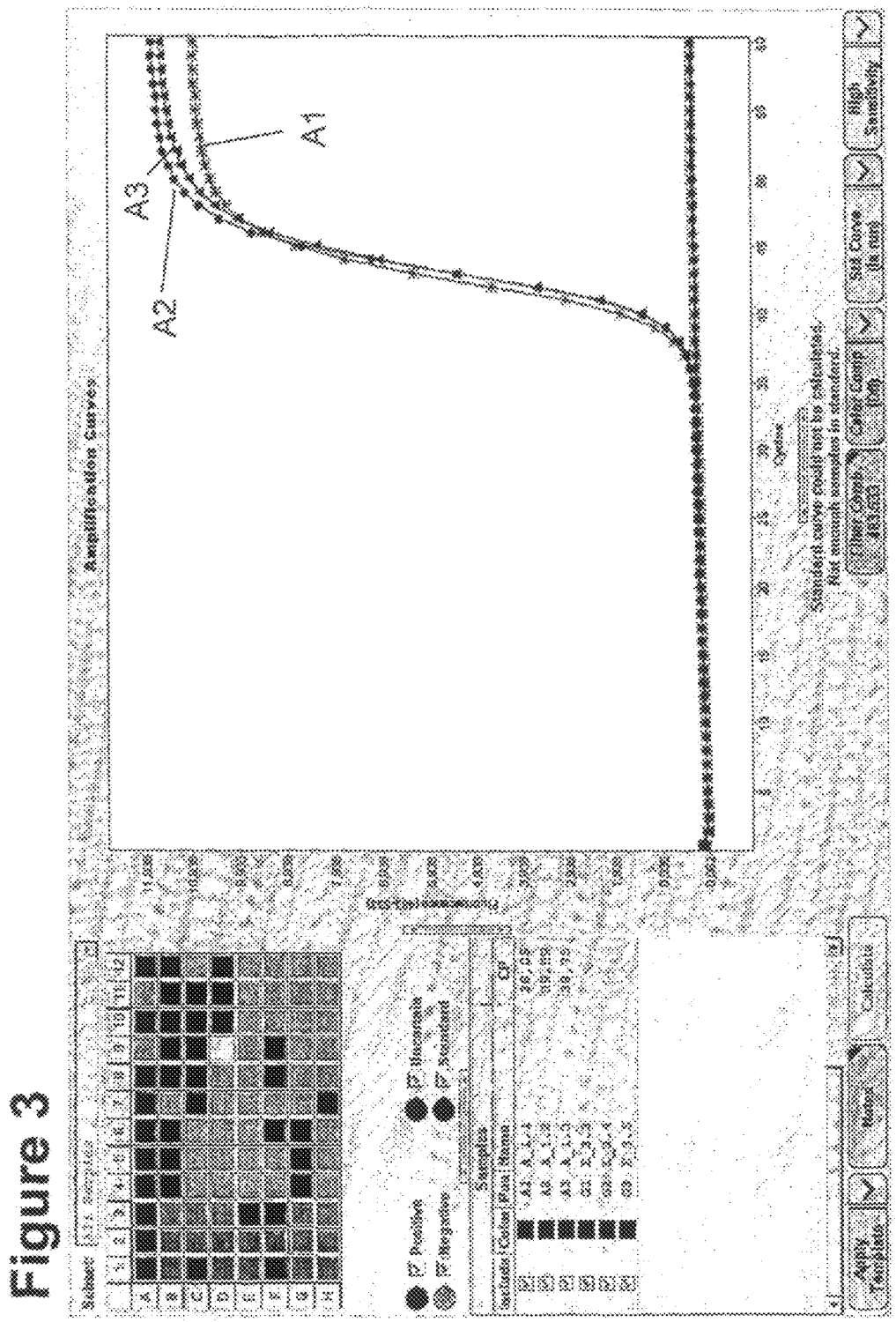
FIG. 3: Representative amplification curves of 6 samples analyzed by the Septin 9 single HeavyMethyl PCR. The signals were obtained in channel 533 nm.

Representative amplification curves of 6 samples with PCR1 of the duplex HeavyMethyl PCR are shown in FIG. 1. The amplification curves of the PCR2 of the duplex reaction are shown in FIG. 2. FIG. 3 showed again the same representative 6 samples amplified with the single HeavyMethyl PCR. As shown in the Figures samples A1.2 and A1.3 were detected in all three cases. Sample A1.1 was not detected by PCR1 but by PCR2, whereas sample E3.4 was positive in PCR2 and not in PCR1 of the duplex reaction. All 4 out of 6 exemplary samples were detected by the duplex PCR. In contrast to that the single HeavyMethyl PCR detects only 3 out of these 6 samples (A1.1, A1.2, and A1.3).

Figure 4:
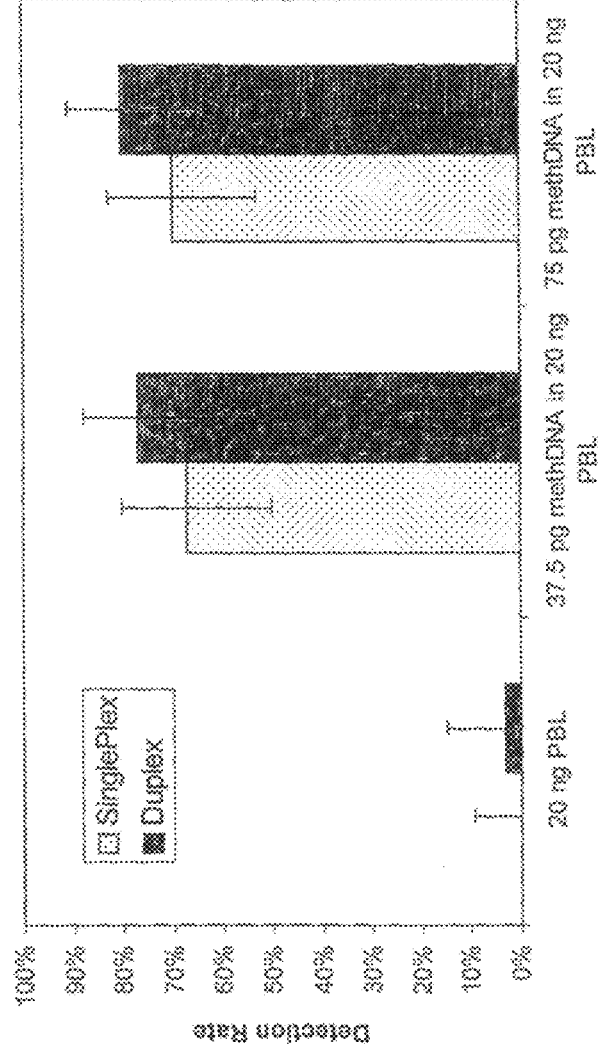
FIG. 4: Diagram illustrating the determined detection rate of samples of with low target copy numbers. 3 different dilution, which were prepared in 30 replicates each. 20 ng PBL DNA (two left bars) and 20 ng PBL DNA containing 37.5 pg methylated DNA (two bars in the center) and 20 ng PBL DNA containing 75 pg methylated DNA were bisulfite converted in 30 replicates. After bisulfite treatment each sample was eluted in 50 μl water and 10 μl (1/5$^{th}$) was applied to the Septin 9 single and duplex HeavyMethyl PCR. The obtained detection rates were calculated from the numbers detected samples out of 30 replicates (see Table 4). The error bars represent the 95% confidence interval to each measurement.

The detection rate was calculated for the three dilutions, which were processed 30 times each. Each single curve, called by the automated analysis of the LightCycler 480 software, was counted as positive. The table 4 collects all crossing points (CP) of the experiment. The resulting detection rates are illustrated in FIG. 4. Non of the samples without methylated DNA was detected by the single PCR, whereas one amplification curve was obtained with the duplex PCR in the channel 533 nm (PCR1). The samples containing 37.5 pg methylated DNA (dilution 2) were detected with rates of 67% (confidence interval of 95% (CI95): 50%-80%) using the single PCR and 70% (CI95: 53%-83%) using the duplex PCR. The samples containing 75 pg methylated DNA were detected with rates of 77% (CI95: 60%-88%) using the single PCR and 80% (CI95: 64%-91%) using the duplex PCR. In the duplex PCR samples were counted as positive, if either the PCR1 (533 nm) or PCR2 (610 nm) showed a amplification curve.

Figure 5:
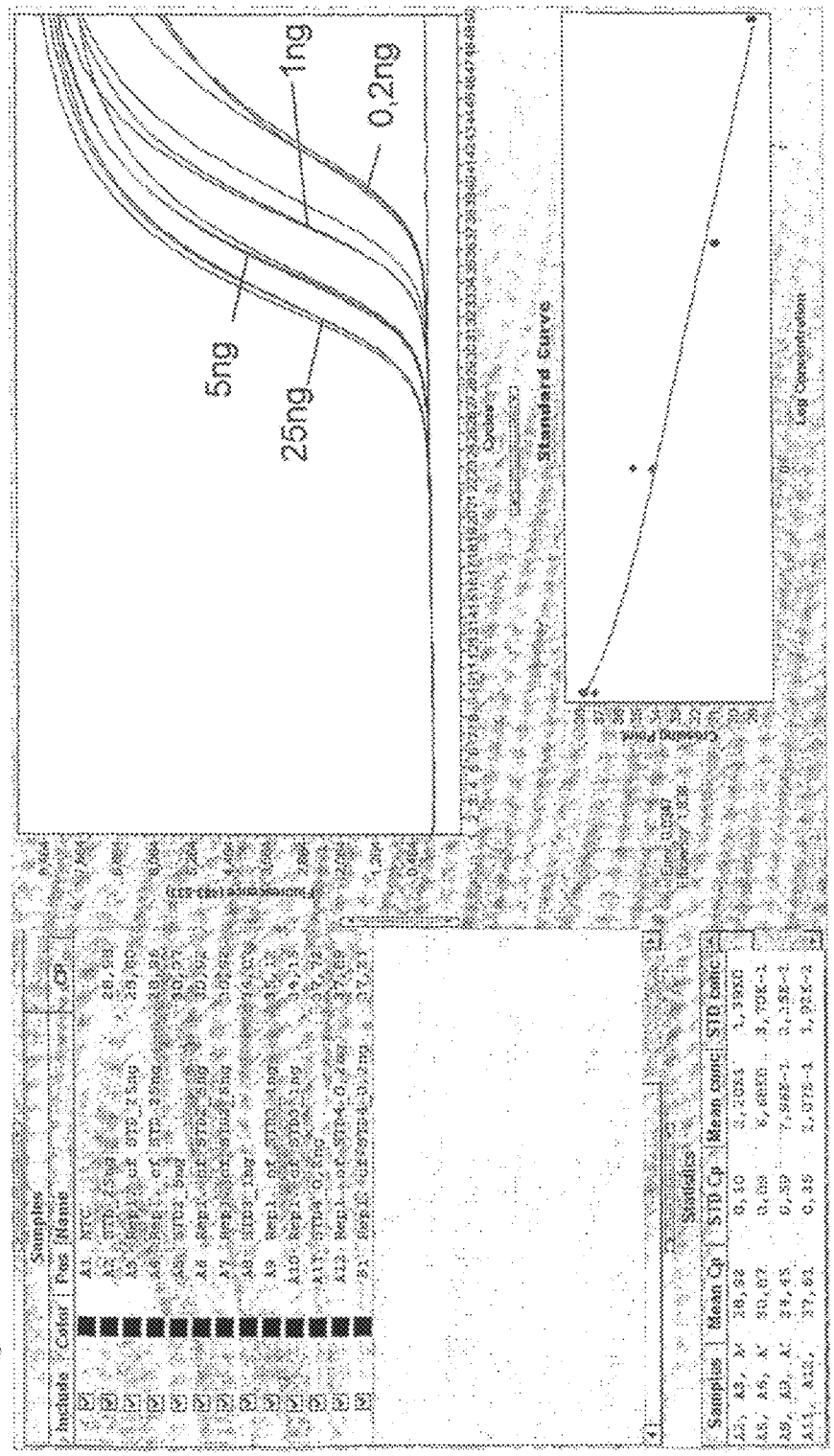
FIG. 5: Standard curve of the PCR1 as part of the duplex Septin 9 HeavyMethyl assay. The dilution series of methylated bisulfite converted DNA contained 25, 5, 1 and 0.2 ng per reaction. The PCR efficiency was calculated with 1.838.
Figure 6:
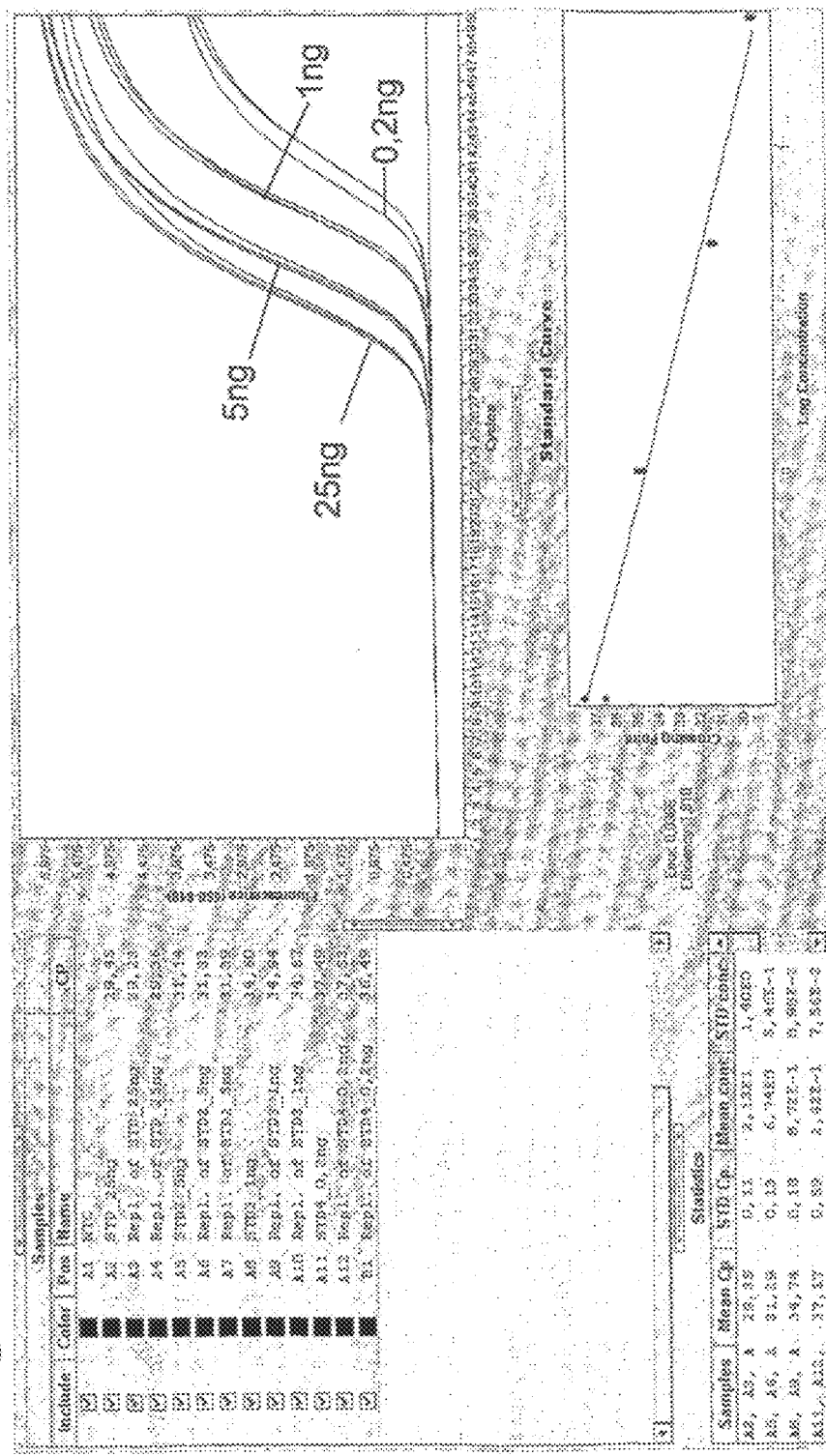
FIG. 6: Standard curve of the PCR2 as part of the duplex Septin 9 HeavyMethyl assay. The dilution series of methylated bisulfite converted DNA contained 25, 5, 1 and 0.2 ng per reaction. The PCR efficiency was calculated with 1.810.
Figure 7:
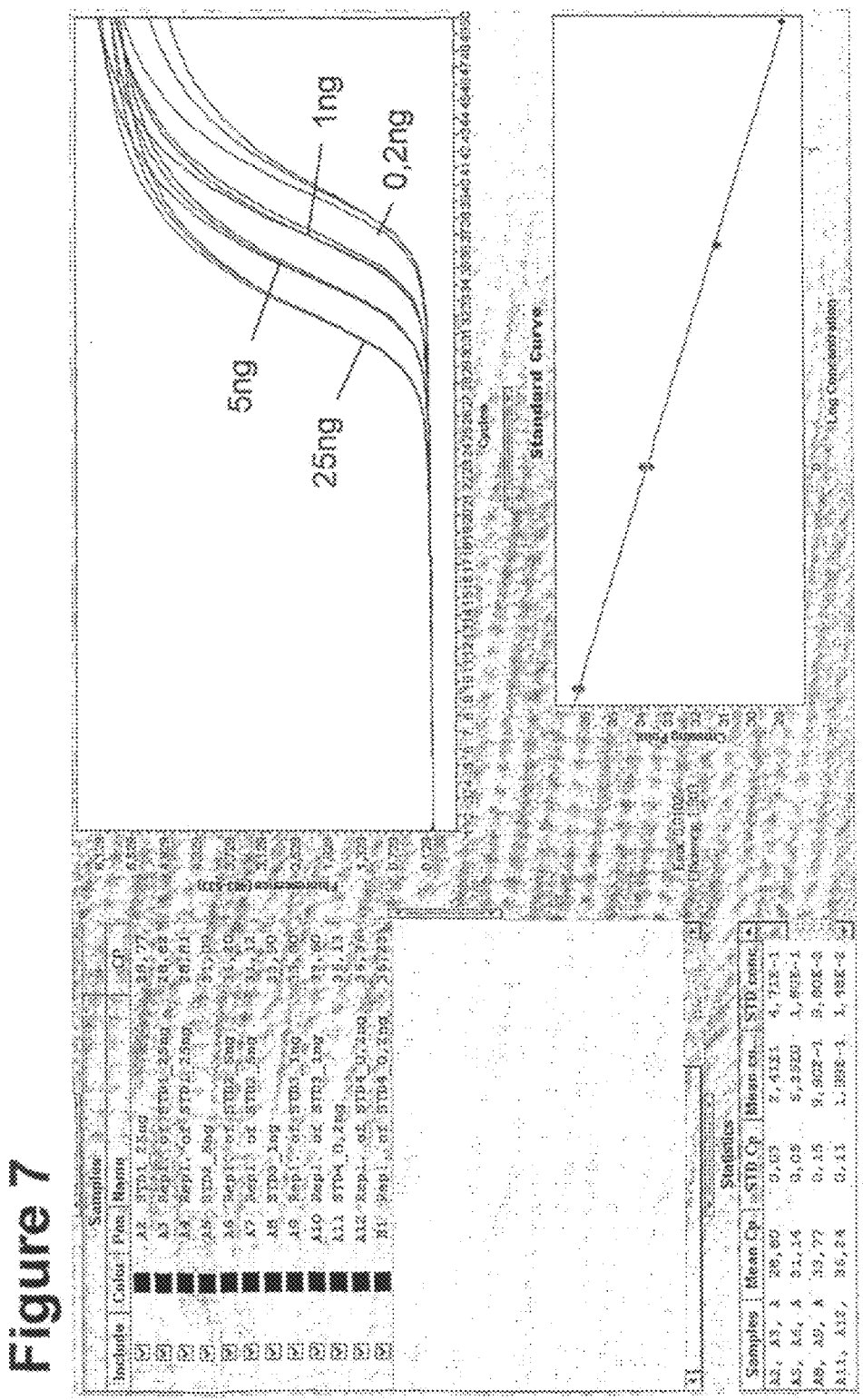
FIG. 7: Standard curve of the Septin 9 single HeavyMethyl PCR generated by a dilution series of methylated bisulfite converted DNA in the concentration range from 25 to 0.2 ng per reaction. The PCR efficiency was calculated with 1.903.

The characteristic of the developed duplex HeavyMethyl PCR was additionally evaluated. For that a dilution series of methylated bisulfite converted DNA was prepared to evaluate the efficiencies of the different PCRs. The standard curve of the PCR1 and PCR2 of the duplex PCR are shown in FIGS. 5 and 6. The PCR efficiencies were determined to 1.838 for PCR1 and to 1.810 for PCR2 respectively. In FIG. 7 the standard curve of the single PCR is shown with a PCR efficiency of 1.903.

Figure 8:
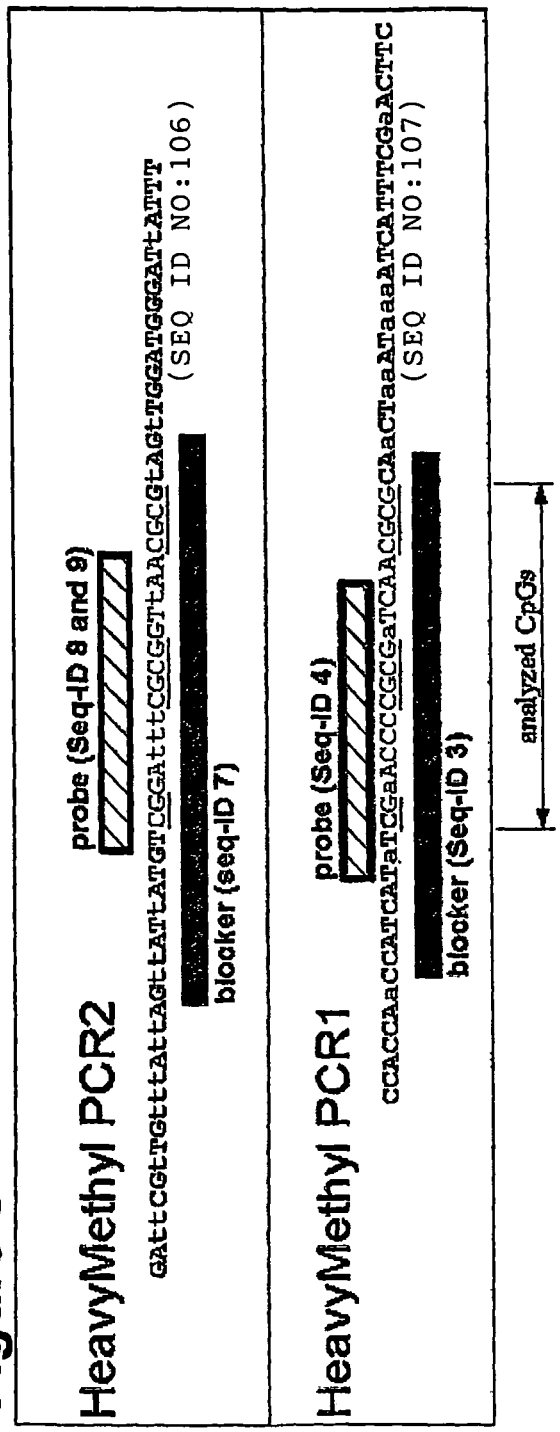
FIG. 8: Scheme of the two amplicons of the Septin 9 duplex HeavyMethyl PCR. The septin 9 single PCR is similar to the PCR2 of the duplex assay.

A schematic presentation of the two sequences amplified in the duplex HeavyMethyl PCR are depicted in FIG. 8. Both amplicons cover the same CpGs of the Septin 9 CpG island. The blocker oligonucleotides span over 5 CpGs, whereas the detection probes bind to only 3 CpGs out of the amplified region. As indicated by FIG. 8, PCR1 and PCR2 comprise each a primer which spans over a single CpG (FIG. 8 shows the bisulfite treated genomic Sequence, primer hybridization areas are printed in bold). To prevent a methylation specific binding of the C-free primers of PCR1 and PCR2 the primer sequences contained a dSpacer modification, which acts as a stable a-basic site at these positions. The methylation specific amplification therefore is only driven by binding of the blocker oligonucleotides to the 5 CpGs in between the primer binding sites.

In general, the clinical sensitivity of a DNA methylation based assay, which is based on the detection of cancer derived methylated DNA in bodily fluids or other remote samples is limited due to the low copy number of cancer specific DNA. The approach of cancer detection and diagnosis of other diseases will be improved by the implementation of the concept of detecting both bisulfite converted strands of the original target DNA.

TABLE 3

Sequences of oligonucleotides described in the example.

SEQ ID NO: 1  5'-CCACCAaCCATCATaTC-3'

SEQ ID NO: 2  5'-GAAGTt-X-GAAATGATtttATttAGtT-3'

SEQ ID NO: 3  5'-CCATCATaTCAaACCCCACAaTCAACACACA-3'C3

SEQ ID NO: 4  5'-FAM-GAtCGCGGGGTtCGAtA-3'BHQ1

SEQ ID NO: 5  5'-AAATaATCCCATCCAaCTa-3'

SEQ ID NO: 6  5'-GAtt-X-GtTGtttAttAGttATtATGT-3'

SEQ ID NO: 7  5'-GttATtATGTtGGAttttGtGGTtAAtGtGtAG-3'C3

SEQ ID NO: 8  5'-TexasRed-TTaACCGCGaaaTCCGAC-3'BHQ2

SEQ ID NO: 8  5'-FAM-TTaACCGCGaaaTCCGAC-3'BHQ1

SEQ ID NO: 10 GAAGTtXGAAATGATtttATttAGtTGCGCGTTGAtC GCGGGGT-tCGAtATGATGGtTGGTGG

TABLE 3-continued

Sequences of oligonucleotides described in the example.

SEQ ID NO: 11 GAttXGtTGtttAttAGttATtATGTCGGAtttCGCG
GTtAACGCGtAGtTGGATGGGATtATTT Fluo = fluoresceine label,
red840 = LightCycler fluorophore label for channel F2,
PH = 3'OH-Phosphorylation,
FAM = Carboxyfluorescein label,
TexasRed = Texas Red fluorophore label,
BHQ1 = BlackHoleQuencher 1,
X = a-basic site by Tetrahydrofuran modification (also known as dSpacer).
Small written "t" points to converted cytosines by bisulfite treatment, respectively small "a" points to the complementary adenosine bases in the reverse complement synthesized strand.

TABLE 4

Obtained CP values from 3 different dilution, which were prepared in 30 replicates each.

| | Septin 9 - Single PCR | | | Septin 9 - Duplex PCR | | | | | |
|---|---|---|---|---|---|---|---|---|---|
| | CP FAM channel | CP FAM channel | CP FAM channel | CP FAM channel | CP TEX channel | CP FAM channel | CP TEX channel | CP FAM channel | CP TEX channel |
| Sample nr. | Dilution 1 | Dilution 2 | Dilution 3 | Dilution 1 | | Dilution 2 | | Dilution 3 | |
| 1 | 39.3 | 38.91 | / | / | 39.59 | 45.44 | / | / | / |
| 2 | 40.27 | 39.29 | / | 39.62 | 38.92 | / | 38.96 | / | / |
| 3 | 40.51 | 40.49 | / | 39.84 | 39.65 | 41.5 | 39.29 | / | / |
| 4 | 38.51 | / | / | 39.27 | 38.25 | / | / | / | / |
| 5 | 42.98 | 41 | / | 40.65 | 37.73 | / | 40.32 | / | / |
| 6 | / | / | / | 40.4 | 40.18 | / | / | / | / |
| 7 | 38.85 | 40.67 | / | / | 40.25 | 41.49 | 39.59 | / | / |
| 8 | / | 39.49 | / | / | / | 40.9 | / | / | / |
| 9 | / | / | / | / | / | / | / | / | / |
| 10 | / | 40.82 | / | / | / | 41.61 | 38.34 | / | / |
| 11 | 39.91 | 42.11 | / | 41.43 | 40.18 | 47.37 | 41.6 | / | / |
| 12 | 41.91 | 40.21 | / | 47.22 | 43.9 | 44.43 | 42.33 | / | / |
| 13 | / | / | / | 42.73 | 39.76 | 43.89 | / | / | / |
| 14 | 41.96 | 39.19 | / | 44.42 | 42.31 | / | 41.28 | / | / |
| 15 | 39.9 | 42.2 | / | 41.81 | 40.08 | 45.84 | 44.03 | / | / |
| 16 | 38.68 | 39.96 | / | 43 | 40.48 | 45.62 | 41.35 | / | / |
| 17 | 41.63 | / | / | 47.04 | 43.53 | 42.02 | 40.64 | / | / |
| 18 | 40.51 | 44.28 | / | 45.11 | / | 43.74 | 42.15 | / | / |
| 19 | 40.95 | 39.89 | / | 44.65 | 41.62 | / | 42.66 | / | / |
| 20 | 37.81 | 38.65 | / | 44.15 | 41.67 | 44.34 | 43.28 | / | / |
| 21 | / | 40.09 | / | / | / | / | 40.02 | / | / |
| 22 | / | / | / | / | / | / | / | / | / |
| 23 | 42.47 | 40.29 | / | 41.06 | 38.46 | 39.84 | / | / | / |
| 24 | / | / | / | / | / | 42.65 | 39.48 | 40.68 | / |
| 25 | 40.85 | / | / | 40.77 | 37.97 | / | / | / | / |
| 26 | 38.87 | 38.75 | / | 39.12 | 38.59 | / | / | / | / |
| 27 | / | 40 | / | 38.68 | 39.36 | 42.54 | 38.6 | / | / |
| 28 | 37.89 | / | / | 40.72 | 38.83 | / | 39.84 | / | / |
| 29 | 39.63 | / | / | 41.87 | / | 39.61 | / | / | / |
| 29 | 39.29 | 39.56 | / | 45.7 | 38.52 | / | / | / | / |
| Number of detected samples | 21 | 20 | 0 | 24 | | 23 | | 1 | |

Dilution 1 contained 20 ng PBL DNA and 75 pg methylated DNA, dilution 2 contained 20 ng PBL DNA and 37.5 pg methylated DNA. To dilution 3 no methylated DNA was spiked. After bisulfite treatment each sample was eluted in 50 µl water and 10 µl ($1/5^{th}$) was applied to the Septin 9 single and duplex HeavyMethyl PCR.

Example 7

Improvements of Examples 3-6

Isolation by means of beads of the chemagic Viral RNA/DNA kit (Chemagen Biopolymer-Technologie AG, Germany, Article Number 1002)—Protocol II:

Plasma was collected as described in WO 2006/113770. In brief, blood was drawn in 10 ml EDTA plasma tubes using the vacutainer system. Tubes were centrifuged at 1500×g for 10 min, the supernatant was transferred to a new tube and centrifuged a second time at 1500×g for 10 min. The supernatant is the plasma for further use (4-5 ml).

For DNA isolation, 5 ml of the Lysis Buffer 1, 7 µl poly-A RNA, 30 µl of Proteinase K solution and 15 µl of a 1:10 dilution of antifoam (Sigma-Aldrich Chemie GmbH, Article Number A5633) were added to the plasma samples (all adjusted to 5 ml). Samples were incubated at 56° C. for 10 min. Thereafter 100 µl of magnetic beads (Article number 1002) and 15 ml of Binding Buffer 2, 2*1, 2*2, 2*3 or 2*4 were added. In order to keep the beads in suspension by gentle agitation, the samples were place on a rotary mixer at room temperature for about 10 or 60 min, respectively, to allow the binding of DNA to the beads. Magnetic beads were separated by placing the reaction tube in a magnetic stand and discarding the plasma/lysis buffer mixture. Beads were washed only once or twice with 3 ml of Wash Buffer 3, before the were resuspended in 1 ml of Wash Buffer 4, and transferred to new tubes. Beads were separated on a magnetic stand, the wash buffer was poured off and the beads were dried at 56° C. After addition of 100 µl Elution Buffer 5, the suspension is incubated for 15 min on the thermomixer at 65° C. After separation of the beads, the elution buffer containing the genomic DNA was recovered. (All reagents were supplied by the chemagic Viral RNA/DNA kit if not indicated otherwise; Binding Buffers 2*1, 2*2, 2*3, and 2*4 are variations of the Binding Buffer 2 which are all commercial available from Chemagen Biopolymer-Technologie AG, Germany).

For bisulfite treatment, the recovered genomic DNA was subjected to the protocol of Example 4.

For purification, the DNA bisulfite treated according to Example 4 was subjected to purification according to the protocol of Example 5(A).

For detection of methylated sequences of the Septin 9 gene, the purified DNA obtained by the protocol of Example 5 was subjected to the single Septin 9 HeavyMethyl PCR (PCR2 of the duplex PCR) of Example 6.

Figure 9:
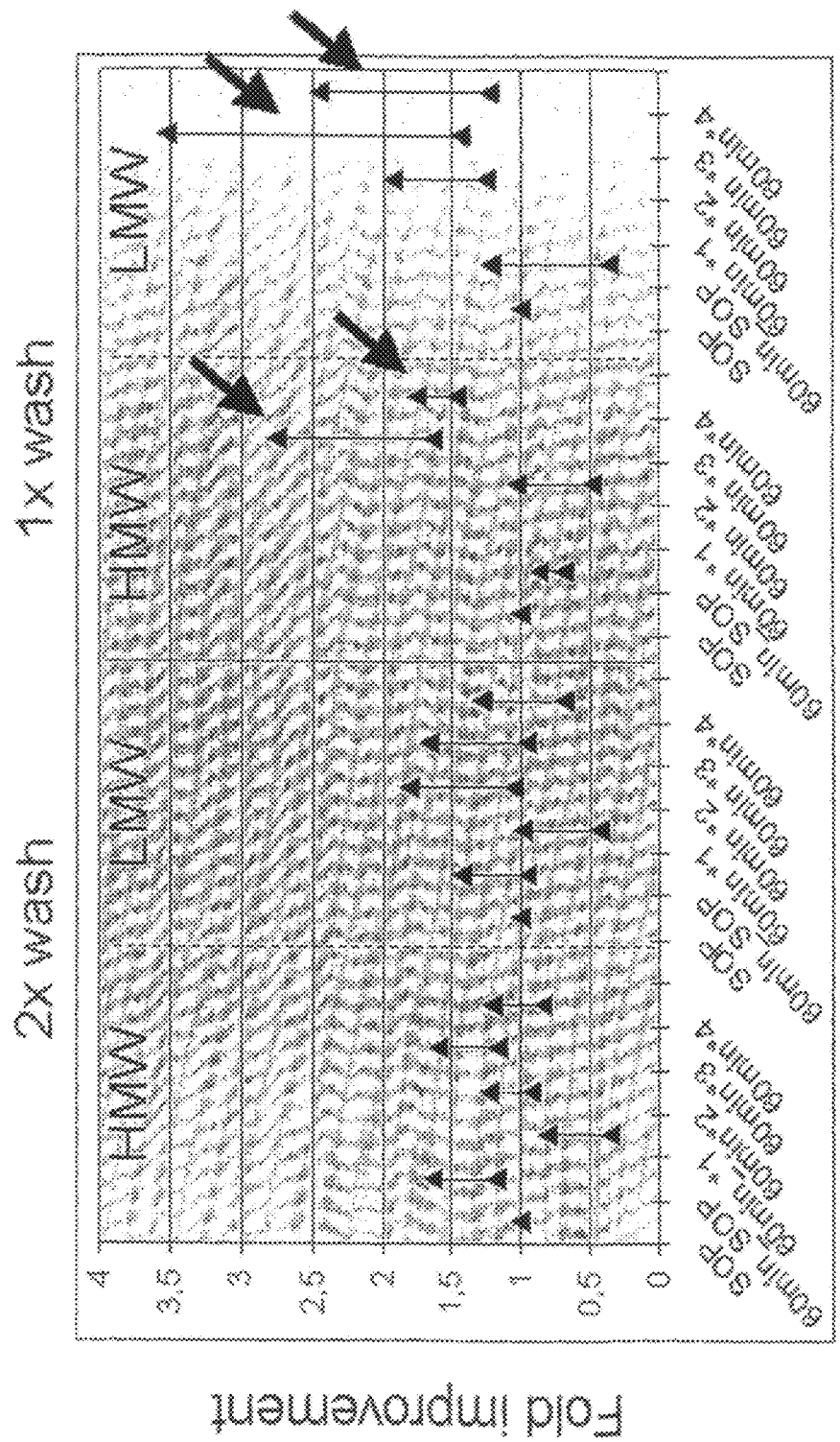
FIG. 9: Results of Example 7 are shown. Increased recovery of low and high molecular weight DNA was detected for samples treated with (i) a single wash with wash buffer 3, (ii) with a 60 min incubation to allow binding of the DNA to beads, and (iii) with the use of the binding buffers 2*3 and 2*4. (SOP=10 min incubation for DNA binding to beads and Binding Buffer 2; 60 min_SOP=60 min incubation for DNA binding to beads and Binding Buffer 2; 60 min*1=60 min incubation for DNA binding to beads and Binding Buffer 2*1; 60 min*2=60 min incubation for DNA binding to beads and Binding Buffer 2*2; 60 min*3=60 min incubation for DNA binding to beads and Binding Buffer 2*3; 60 min*4=60 min incubation for DNA binding to beads and Binding Buffer 2*4; triangles and lines inbetween represent measuring points or ranges of samples treated as indicated).

The results of this PCR are shown in FIG. 9. Best results i.e. increased recovery of low and high molecular weight DNA was obtained by (i) a single wash with wash buffer 3, (ii) by 60 min incubation to allow binding of the DNA to beads, and (iii) by use of the binding buffers 2*3 and 2*4.

Example 8

Workflow Study

Sample Collection

Plasma samples were collected using Vacutainer Lavender tubes with EDTA (BD, Article Number 366643). The collected samples (volume 5 ml) were stored frozen at −80 C upon usage. In total 268 plasma samples were collected: 171 normal (healthy), 97 colorectal cancer whereof 22 were of stage I, 37 were of stage II, and 38 were of stage III.

DNA Extraction 5 ml Lysis Buffer I, 7 µl Poly(A) RNA 1 µg/µl (Roche), and 30 µl Proteinase K were added to each sample, and thoroughly mixed for 10 s. Subsequently, the samples were incubated at 56° C. for 10 min. 100 µl Chemagen magnetic beads and 15 ml Binding Buffer 2*3 were added to each sample and thoroughly mixed for 10 s. The sample were incubated for 60 min at room temperature upon continuous agitation. Thereafter each sample was placed in a magnetic separator for 4 min before the supernatant is discarded. Beads of each sample were resuspended in 3 ml of Wash Buffer 3 and 1.5 ml of each sample were transferred into ml tube. Each tube was placed in a magnetic separator for 2 min before the supernatant was discarded. The remainders of each sample were again combined in a 2 ml tube. Said tube was then placed in a magnetic separator for 2 min and the supernatant is discarded. After a short centrifugation, each tube was again placed in a magnetic separator for 2 min and the remaining supernatant was removed. Beads of each sample were then dried at 56° C. for 3-5 min with open tube lid. For DNA elution, 100 µl of Elution Buffer 5 were added to the beads of each sample. After resuspension, beads of each sample were incubated at 65° C. for 15 min upon continuous agitation (1,400 rpm). Beads of each sample were briefly centrifuged, before each tube was placed in a magnetic separator for 2 min and the eluate with DNA is transferred into a 0.5 ml tube. In the case that the eluate contained still beads, the magnetic separation step was repeated. The volume of each eluate was adjusted to 100 µl before storage at 4° C. (All reagents were supplied by the chemagic Viral RNA/DNA kit (Chemagen Biopolymer-Technologie AG, Germany, Article Number 1002) if not indicated otherwise; Binding Buffers 2*3 is variation of the Binding Buffer 2 which is commercial available from Chemagen Biopolymer-Technologie AG, Germany)

Bisulfite Treatment

The following solutions were prepared. They were sufficient for 25 reactions.

Bisulfite solution: 4.71 g Sodium disulfite (Merck Article Number 1.06528.0500) and 1.13 g sodium sulfite (Fluke Article Number 71988) were dissolved by adding 10 ml ddH$_2$O. This resulted in a solution having 4.9 mol/l hydrogen sulfite (the active reagent for bisulfite treatment). If the need has been, the pH of the solution was adjusted by means of 0.2 mol/l NaOH (VWR or Sigma Aldrich) to be in the range between 5.4 and 5.5. In order to dissolve the salts completely, the mixture may have been mixed vigorously and heated to 50° C.

DME-radical scavenger solution: 188 mg of 6-hydroxy-2,5,7,8-tetramethyl-chroman-2-carboxylic acid (Aldrich Article Number 23,881-3) were dissolved in 1.5 ml DME (Merck Article Number 8.02934.0250). In order to ensure that no un-dissolved particles remain, the mixture was vigorously mixed.

190 µl of Bisulfite solution and 30 µl of DME solution containing the radical scavenger were added to each 100 µl sample of eluated DNA. The following temperature protocol was applied on the samples by means of an Eppendorf Thermocycler (Eppendorf mastercycler): 5 min 99° C.; 25 min 50° C.; 5 min 99° C.; 1 h 25 min 50° C.; 5 min 99° C.; 4 h 55 min 50° C., 20° C.

Bisulfite Purification:

The 320 µl of each bisulfite treated sample were transferred to a 2.0 ml tube. 1 µl of polyA RNA 500 ng/µl (Roche) and 1.5 ml of Binding Buffer 1 were added to each sample. After thoroughly mixing, 10 µl of Chemagen magnetic beads were added and briefly mixed. The samples were incubated 60 min at room temperature upon continuous agitation (1,000 rpm). Thereafter, each sample was placed in a magnetic separator for 2 min and the supernatant was discarded. Samples were briefly centrifuged, placed again into the magnetic separators for 2 min and the supernatant was discarded. Samples were washed twice by adding 300 µl of Wash Buffer 2 to each tube, resuspending the beads, placing each tube for 2 min in a magnetic separator, and discarding the supernatant. Subsequently, the samples were washed by addition of 300 µl of 70% ethanol (VWR or Sigma Aldrich) to each tube, resuspending the beads, placing each tube for 2 min in a magnetic separator, and discarding the supernatant. The tubes were briefly centrifuged, placed again into magnetic separators and the remaining supernatants were removed. Thereafter, samples were dried at 55° C. for 3-5 min with open tube lid. For DNA elution, 55 µl of 10 mmol/Tris pH 7.2 (VWR or Sigma Aldrich) were added to each sample. The samples were incubated for 15 min at 55° C. upon continuous agitation (1,000 rpm). Thereafter, each of the samples were briefly centrifuged, placed in a magnetic separator and the eluate containing the DNA was transferred into a new 1.7 ml tube. The volume of each eluate was adjusted to 55 µl with 10 mM Tris pH 7.2 before storage at 4° C. (All reagents were supplied by the chemagic Viral RNA/DNA kit (Chemagen Biopolymer-Technologie AG, Germany, Article Number 1002) if not indicated otherwise).

Real Time PCR Analysis of the Methylation of the Septin 9 Gene

Each sample was analyzed in triplicates. For quantification of amplificates, the following standards were used: 2×20 ng, 2×5 ng, 2×1 ng, 3×0.4 ng of genomic DNA treated as the samples to be analyzed.

A master mix containing all reagents for PCR was prepared. 15 µl of this master mix were pipetted into each well of a 96 well plate. Subsequently, respectively 10 µl of purified bisulfite treated DNA were added to each well.

Each reaction mixture contained the following (final volume 25 µl):

| reagent (concentration) | volume | final concentration |
| --- | --- | --- |
| water | 1.875 µl | |
| primer (30 µmol/l)<br>SEQ ID NO: 5 '-AAATAATCCCATCCAACTA-3' | 0.25 µl | 0.30 µmmol/l |
| primer (30 µmol/l)<br>SEQ ID NO: 6 5'-GATT-X-GTTGTTTATTAGTTATTATGT-3' | 0.25 µl | 0.30 µmmol/l |
| blocker (100 µmol/l)<br>SEQ ID NO: 7 5'-GTTATTATGTTGGATTTTGTGGTTAATGTGT<br>AG-3'C3 | 0.25 µl | 1.00 µmol/l |
| probe (20 µmol/l)<br>SEQ ID NO: 8 5'-FAM-TTAACCGCGAAATCCGAC-3'BHQ1 | 0.125 µl | 0.10 µmol/l |
| PCR puffer 2x<br>QuantiTect Multiplex PCR NoROX Kit (Quiagen<br>Article Number 204743 or 204745) | 12.5 µl | 1x |
| DNA | 10.0 µl | |

Plates were placed into Lightcycler 480 Real time PCR Thermocyclers (Roche Diagnostics) and the following temperature protocol was applied: 95° C. 30 min; 55×: 95° C. 10 s, 56° C. 30 s (single detection), 40° C. 5 s.

Amplificates of the PCR are indicative for the presence of methylation of the CpG dinucleotides covered the PCR Resulting data was analyzed in three ways:

1) A sample was considered as positive, when one of the triplicates was positive.

2) A sample was considered as positive, when two of the triplicates was positive.

3) Quantitative analysis with optimized cutoff using ROC analysis with specificity at 95% and 90%.

The following Tables 5 and 6 summaries the results:

TABLE 5

Septin 9 PCR performance on healthy controls and colorectal cancer samples

| data interpretation modus | sensitivity | specificity |
| --- | --- | --- |
| 1/3 | 73/97 75.3% | 23/171 86.5% |
| 2/3 | 55/97 56.7% | 4/171 97.6% |
| quantitative | 61%<br>68% | 95%, or<br>90% |

TABLE 6

Septin 9 PCR performance on colorectal cancer samples by stage

| | data interpretation modus | |
| --- | --- | --- |
| | 1/3 | 2/3 |
| stage I | 10/22 | 7/22 |
| stage II | 31/37 | 24/37 |
| stage III | 32/38 | 24/38 |
| overall | 73/97 75.3% | 55/97 57% |

Example 8

DNA Preparation from Urine

To each 8 ml urine sample 8 ml Chemagen Lysis Buffer, 10.5 µl polyadenylic acid (poly A RNA Roche Applied Sciences #10108626, 1 µg/µl), and 45 µl Chemagen Protease solution were added. Samples were mixed by vortexing for 10 s, and incubated at 56° C. for 10 min. 150 µl of Chemagen beads were added to the lysate, and 22.5 µl of Chemagen Binding Buffer 2*3. The sample was mixed by vortexing for 10 s. Samples were then mixed on a rotator for 1 h at room temperature. Samples were then placed on a magnetic separator for 4 min, the supernatant discarded and 3 ml of wash buffer were added. The samples were mixed. 1.5 ml aliquots were transferred to a 2 ml safelock tube, placed on a magnetic separator for 2 min and wash buffer was removed by pipetting. The remaining sample was transferred to the safelock tube, placed on the separator and wash buffer was removed. Residual buffer was removed following a 20 s centrifugation at 1,000 rpm, and the magnetic particles were air dried for 5 min at 65° C. 100 µl elution buffer was added and the beads were incubated at 65° C. in a thermal mixer at 1,000 rpm. Samples were then placed in a magnetic separator for 2 min and the eluate containing extracted DNA was transferred to a microcentrifuge tube and stored for further processing.

This workflow was tested in a study of 20 urine samples, said samples were collected from patients following prostatic massage. Two 8 ml whole urine samples were tested per patient. Samples were prepared without centrifugation and extracted as described above. Following extraction, DNA samples were diluted 1/10 in elution buffer and total genomic DNA recovery was determined by real time PCR with the CFF1 assay (performed as described in WO 2007/039101). As illustrated in the following table, total DNA recovery was very similar between replicates from the same patient, demonstrating consistent DNA extraction. Total DNA levels varied greatly between patients, consistent with previous observations.

TABLE 7

Total DNA revovery (CFF1) from replicate 8 ml extractions from 20 patient samples.

| Sample | ng/ml DNA | mean | standard deviation |
| --- | --- | --- | --- |
| 1A | 143.75 | 142.50 | 1.77 |
| 1B | 141.25 | | |
| 2A | 19.75 | 21.88 | 3.01 |
| 2B | 24.00 | | |
| 3A | 8.00 | 7.88 | 0.17 |
| 3B | 7.76 | | |
| 4A | 22.88 | 22.81 | 0.09 |
| 4B | 22.75 | | |
| 5A | 4.59 | 4.33 | 0.36 |
| 5B | 4.08 | | |
| 6A | 185.00 | 194.38 | 13.26 |
| 6B | 203.75 | | |
| 7A | 45.13 | 45.75 | 0.88 |
| 7B | 46.38 | | |
| 8A | 12.18 | 11.99 | 0.27 |
| 8B | 11.80 | | |
| 9A | 72.63 | 72.13 | 0.71 |
| 9B | 71.63 | | |
| 10A | 43.88 | 41.19 | 3.80 |
| 10B | 38.50 | | |
| 11A | 20.50 | 20.38 | 0.18 |
| 11B | 20.25 | | |
| 12A | 9.71 | 9.35 | 0.51 |
| 12B | 8.99 | | |
| 13A | 119.38 | 99.06 | 28.73 |
| 13B | 78.75 | | |
| 14A | 130.00 | 165.63 | 50.38 |
| 14B | 201.25 | | |
| 15A | 22.25 | 24.19 | 2.74 |
| 15B | 26.13 | | |
| 16A | 152.50 | 142.50 | 14.14 |
| 16B | 132.50 | | |

TABLE 7-continued

Total DNA revovery (CFF1) from replicate 8 ml extractions from 20 patient samples.

| Sample | ng/ml DNA | mean | standard deviation |
|---|---|---|---|
| 17A | 14.88 | 13.30 | 2.23 |
| 17B | 11.73 | | |
| 18A | 17.25 | 17.75 | 0.71 |
| 18B | 18.25 | | |
| 19A | 3.65 | 3.61 | 0.06 |
| 19B | 3.56 | | |

TABLE 7-continued

Total DNA revovery (CFF1) from replicate 8 ml extractions from 20 patient samples.

| Sample | ng/ml DNA | mean | standard deviation |
|---|---|---|---|
| 20A | 472.50 | 451.88 | 29.17 |
| 20B | 431.25 | | |

(All reagents and solutions not specified otherwise were obtained from Chemagen, Biopolymer-Technologie AG, Germany)

The invention claimed is:

1. A method for methylation analysis, comprising
   a) treating genomic DNA with one or more reagents to convert unmethylated cytosine bases to uracil sulfonate or to another base having a different binding behavior than cytosine, while methylated cytosine remains unchanged;
   b) amplifying the treated DNA by means of
      i) at least one oligonucleotide comprising or consisting essentially of a sequence as defined by SEQ ID NO: 5 or sequence variants derived from said sequence by 5'-terminal and/or 3'-terminal deletion of 1, 2, 3, 4 or 5 nucleotides; and
      ii) at least one oligonucleotide comprising or consisting essentially of a sequence as defined by SEQ ID NO: 63 or sequence variants derived from said sequence by 5'-terminal and/or 3'-terminal deletion of 1, 2, 3, or nucleotides;
   wherein said oligonucleotides are suitable for use as primers;
      and optionally, a polymerase; and
   c) deducing the presence or absence of methylation of the CpG dinucleotides amplified in step b) from the results of step b).

2. The method according to claim 1, wherein the amplifying of the treated DNA additionally involves
   iv) at least one oligonucleotide comprising or consisting essentially of a sequence selected from the group consisting of SEQ ID NO: 3, 7, 9, 23-30, 49-57, 73-76, 91, and 97-101, wherein said one or more oligonucleotides are suitable for use as blockers; and
   v) optionally, at least one oligonucleotide comprising or consisting essentially of a sequence selected from the group consisting of SEQ ID NO: 4, 8, 31-42, 58-61, 83 and 84, wherein said one or more oligonucleotides are suitable for use as probes and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105, wherein said one or more oligonucleotide combinations are suitable for use as probe combinations.

3. A method for detecting and/or classifying cellular proliferative disorders, comprising:
   a) treating genomic DNA with one or more reagents to convert unmethylated cytosine bases to uracil sulfonate or to another base having a different binding behavior than cytosine, while methylated cytosine remains unchanged;
   b) amplifying the treated DNA by means of
      i) at least one oligonucleotide comprising or consisting essentially of a sequence as defined by SEQ ID NO: 5 or sequence variants derived from said sequence by 5'-terminal and/or 3'-terminal deletion of 1, 2, 3, 4 or 5 nucleotides; and
      ii) at least one oligonucleotide comprising or consisting essentially of a sequence as defined by SEQ ID NO: 63 or sequence variants derived from said sequence by 5'-terminal and/or 3'-terminal deletion of 1, 2, 3, or 4 nucleotides;
   wherein said oligonucleotides are suitable for use as primers;
      and optionally, a polymerase; and
   c) deducing the presence or absence of methylation of the CpG dinucleotides amplified in step b) from the result of step b), wherein at least one of detecting and classifying cellular proliferative disorders is, at least in part, afforded.

4. The method according to claim 3, wherein the amplifying of the treated DNA additionally involves
   iv) at least one oligonucleotide comprising or consisting essentially of a sequence selected from the group consisting of SEQ ID NO: 3, 7, 9, 23-30, 49-57, 73-76, 91, and 97-101, wherein said one or more oligonucleotides are suitable for use as blockers; and
   v) optionally, at least one oligonucleotide comprising or consisting essentially of a sequence selected from the group consisting of SEQ ID NO: 4, 8, 31-42, 58-61, 83 and 84, wherein said one or more oligonucleotides are suitable for use as probes and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105, wherein said one or more oligonucleotide combinations are suitable for use as probe combinations.

5. Kit, comprising
   a) at least one oligonucleotide comprising or consisting essentially of a sequence as defined by SEQ ID NO: 5 or sequence variants derived from said sequence by 5'-terminal and/or 3'-terminal deletion of 1, 2, 3, 4 or 5 nucleotides; and
   b) at least one oligonucleotide comprising or consisting essentially of a sequence as defined by of SEQ ID NO: 63 or sequence variants derived from said sequence by 5'-terminal and/or 3'-terminal deletion of 1, 2, 3, or 4 nucleotides;
   and optionally, a polymerase.

6. The kit according to claim 5 further comprising
   (d) at least one oligonucleotide comprising or consisting essentially of a sequence selected from the group consisting of SEQ ID NO: 3, 7, 9, 23-30, 49-57, 73-76, 91, and 97-101;
   (e) optionally, at least one oligonucleotide comprising or consisting essentially of a sequence selected from the group consisting of SEQ ID NO: 4, 8, 31-42, 58-61, 83, and 84, and/or at least one oligonucleotide combination comprising or consisting essentially of either the sequences of SEQ ID NO: 77 and 78, of SEQ ID NO: 79 and 80, of SEQ ID NO: 81 and 82, of SEQ ID NO: 102 and 103, or of SEQ ID NO: 104 and 105.

* * * * *

SEQUENCE LISTING

```
<160> NUMBER OF SEQ ID NOS: 107

<210> SEQ ID NO 1
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 1
ccaccaacca tcatatc                                                    17

<210> SEQ ID NO 2
<211> LENGTH: 27
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (7)
<223> OTHER INFORMATION: unknown base

<400> SEQUENCE: 2
gaagttngaa atgattttat ttagttg                                         27

<210> SEQ ID NO 3
<211> LENGTH: 31
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 3
ccatcatatc aaaccccaca atcaacacac a                                    31

<210> SEQ ID NO 4
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 4
gatcgcgggg ttcgata                                                    17

<210> SEQ ID NO 5
<211> LENGTH: 19
<212> TYPE: DNA
```

```
<213> ORGANISM: Artificial Sequence
<220> FEATURE:
<223> OTHER INFORMATION: oligonucleotide for methylation analysis of
      Septin 9

<400> SEQUENCE: 5
aaataatccc atccaacta                                                    19

<210> SEQ ID NO 6
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (5)
<223> OTHER INFORMATION: unknown base

<400> SEQUENCE: 6
gattngttgt ttattagtta ttatgt                                            26

<210> SEQ ID NO 7
<211> LENGTH: 33
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 7
gttattatgt tggattttgt ggttaatgtg tag                                    33

<210> SEQ ID NO 8
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 8
ttaaccgcga aatccgac                                                     18

<210> SEQ ID NO 9
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 9
accatcatat caaaccccac aatcaacaca ca                                     32

<210> SEQ ID NO 10
<211> LENGTH: 63
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (7)
<223> OTHER INFORMATION: unknown base

<400> SEQUENCE: 10
```

-continued

```
gaagttngaa atgattttat ttagttgcgc gttgatcgcg gggttcgata tgatggttgg    60
tgg                                                                  63

<210> SEQ ID NO 11
<211> LENGTH: 65
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (5)
<223> OTHER INFORMATION: unknown base

<400> SEQUENCE: 11
gattngttgt ttattagtta ttatgtcgga tttcgcggtt aacgcgtagt tggatgggat    60
tattt                                                                65

<210> SEQ ID NO 12
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 12
cccaccaacc atcatat                                                   17

<210> SEQ ID NO 13
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 13
cccaccaacc atcatatc                                                  18

<210> SEQ ID NO 14
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 14
acccaccaac catcata                                                   17

<210> SEQ ID NO 15
<211> LENGTH: 20
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 15
ctacccacca accatcatat                                                20

<210> SEQ ID NO 16
<211> LENGTH: 26
<212> TYPE: DNA
<213> ORGANISM: Artificial Sequence
```

```
<220> FEATURE:
<223> OTHER INFORMATION: oligonucleotide for methylation analysis of
      Septin 9

<400> SEQUENCE: 16
gaagttggaa atgattttat ttagtt                                          26

<210> SEQ ID NO 17
<211> LENGTH: 27
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 17
gaagttggaa atgattttat ttagttg                                         27

<210> SEQ ID NO 18
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 18
gaagttagaa atgattttat ttagtt                                          26

<210> SEQ ID NO 19
<211> LENGTH: 27
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 19
gaagttagaa atgattttat ttagttg                                         27

<210> SEQ ID NO 20
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (6)
<223> OTHER INFORMATION: unknown base

<400> SEQUENCE: 20
aagttngaaa tgattttatt tagtt                                           25

<210> SEQ ID NO 21
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (7)
<223> OTHER INFORMATION: unknown base

<400> SEQUENCE: 21
gaagttngaa atgattttat ttagtt                                          26
```

<210> SEQ ID NO 22
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (6)
<223> OTHER INFORMATION: unknown base

<400> SEQUENCE: 22
aagttngaaa tgattttatt tagttg                                          26

<210> SEQ ID NO 23
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 23
catcatatca aaccccacaa tcaacacaca ac                                   32

<210> SEQ ID NO 24
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 24
ccatcatatc aaaccccaca atcaacacac aa                                   32

<210> SEQ ID NO 25
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 25
atcatatcaa accccacaat caacacacaa ct                                   32

<210> SEQ ID NO 26
<211> LENGTH: 31
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 26
accatcatat caaaccccac aatcaacaca c                                    31

<210> SEQ ID NO 27
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 27
aaccatcata tcaaacccca caatcaacac ac    32

<210> SEQ ID NO 28
<211> LENGTH: 28
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 28
agttgtgtgt tgattgtggg gtttgata    28

<210> SEQ ID NO 29
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 29
agttgtgtgt tgattgtggg gtttg    25

<210> SEQ ID NO 30
<211> LENGTH: 31
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 30
atttagttgt gtgttgattg tggggtttga t    31

<210> SEQ ID NO 31
<211> LENGTH: 19
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 31 gaacccgcg atcaacgcg    19

<210> SEQ ID NO 32
<211> LENGTH: 20
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 32
tagttgcgcg ttgatcgcgg    20

<210> SEQ ID NO 33
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 33
tagttgcgcg ttgatcgc    18

```
<210> SEQ ID NO 34
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 34
ccgcgatcaa cgcgc                                                     15

<210> SEQ ID NO 35
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 35
cgcgttgatc gcggg                                                     15

<210> SEQ ID NO 36
<211> LENGTH: 14
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 36
cgcgttgatc gcgg                                                      14

<210> SEQ ID NO 37
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 37
accccgcgat caacg                                                     15

<210> SEQ ID NO 38
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 38
tgatcgcggg gttcg                                                     15

<210> SEQ ID NO 39
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 39
aaccccgcga tcaac                                                     15
```

```
<210> SEQ ID NO 40
<211> LENGTH: 15
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 40
gttgatcgcg gggtt                                                        15

<210> SEQ ID NO 41
<211> LENGTH: 14
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 41
ccccgcgatc aacg                                                         14

<210> SEQ ID NO 42
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 42
cgatcaacgc gcaactaa                                                     18

<210> SEQ ID NO 43
<211> LENGTH: 20
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 43
aaataatccc atccaactac                                                   20

<210> SEQ ID NO 44
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 44
gattggttgt ttattagtta ttatgt                                            26

<210> SEQ ID NO 45
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 45
attggttgtt tattagttat tatgt                                             25

<210> SEQ ID NO 46
<211> LENGTH: 26
```

```
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 46
gattagttgt ttattagtta ttatgt                                          26

<210> SEQ ID NO 47
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 47
attagttgtt tattagttat tatgt                                           25

<210> SEQ ID NO 48
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (4)
<223> OTHER INFORMATION: unknown base

<400> SEQUENCE: 48
attngttgtt tattagttat tatgt                                           25

<210> SEQ ID NO 49
<211> LENGTH: 33
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 49
attatgttgg attttgtggt taatgtgtag ttg                                  33

<210> SEQ ID NO 50
<211> LENGTH: 33
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 50
attatgttgg attttgtggt taatgtgtag ttg                                  33

<210> SEQ ID NO 51
<211> LENGTH: 31
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 51
ccatccaact acacattaac cacaaaatcc a                                    31
```

```
<210> SEQ ID NO 52
<211> LENGTH: 29
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 52
atccaactac acattaacca caaaatcca                                           29

<210> SEQ ID NO 53
<211> LENGTH: 28
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 53
ccaactacac attaaccaca aaatccaa                                            28

<210> SEQ ID NO 54
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 54
caactacaca ttaaccacaa aatcca                                              26

<210> SEQ ID NO 55
<211> LENGTH: 37
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 55
attagttatt atgttggatt ttgtggttaa tgtgtag                                  37

<210> SEQ ID NO 56
<211> LENGTH: 37
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 56
agttattatg ttggattttg tggttaatgt gtagttg                                  37

<210> SEQ ID NO 57
<211> LENGTH: 33
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 57
ttatgttgga ttttgtggtt aatgtgtagt tgg                                      33

<210> SEQ ID NO 58
<211> LENGTH: 19
```

```
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 58
cggatttcgc ggttaacgc                                                       19

<210> SEQ ID NO 59
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 59
cgttaaccgc gaaatccg                                                        18

<210> SEQ ID NO 60
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 60
cgcgttaacc gcgaaatc                                                        18

<210> SEQ ID NO 61
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 61
atttcgcggt taacgcg                                                         17

<210> SEQ ID NO 62
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9
<220> FEATURE:
<221> NAME/KEY: unsure
<222> LOCATION: (4)
<223> OTHER INFORMATION: unknown base

<400> SEQUENCE: 62
attngttgtt tattagttat tatgt                                                25

<210> SEQ ID NO 63
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 63
gattggttgt ttattagtta ttatgt                                               26
```

```
<210> SEQ ID NO 64
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 64
gattagttgt ttattagtta ttatgt                                          26

<210> SEQ ID NO 65
<211> LENGTH: 16
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 65
cccaacaccc accttc                                                     16

<210> SEQ ID NO 66
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 66
caacaaccaa cccaaca                                                    17

<210> SEQ ID NO 67
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 67
caacaaccaa cccaacac                                                   18

<210> SEQ ID NO 68
<211> LENGTH: 16
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 68
aacccaacac ccacct                                                     16

<210> SEQ ID NO 69
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 69
caacccaaca cccacct                                                    17

<210> SEQ ID NO 70
<211> LENGTH: 17
```

```
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 70
caacccaaca cccacct                                                        17

<210> SEQ ID NO 71
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 71
aacccaacac ccacctt                                                        17

<210> SEQ ID NO 72
<211> LENGTH: 20
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 72
accaacccaa cacccacctt                                                     20

<210> SEQ ID NO 73
<211> LENGTH: 31
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 73
gttattatgt tggattttgt ggttaatgtg t                                        31

<210> SEQ ID NO 74
<211> LENGTH: 35
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 74
tattatgttg gattttgtgg ttaatgtgta gttgg                                    35

<210> SEQ ID NO 75
<211> LENGTH: 33
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 75
gttattatgt tggattttgt ggttaatgtg tag                                      33

<210> SEQ ID NO 76
<211> LENGTH: 33
<212> TYPE: DNA
<213> ORGANISM: Artificial Sequence
```

```
<220> FEATURE:
<223> OTHER INFORMATION: oligonucleotide for methylation analysis of
      Septin 9

<400> SEQUENCE: 76
gttattatgt tggattttgt ggttaatgtg tag                                    33

<210> SEQ ID NO 77
<211> LENGTH: 19
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 77
tcgcggttaa cgcgtagtt                                                    19

<210> SEQ ID NO 78
<211> LENGTH: 22
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 78
atgggattat ttcggatttc ga                                                22

<210> SEQ ID NO 79
<211> LENGTH: 18
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 79
tttcgcggtt aacgcgta                                                     18

<210> SEQ ID NO 80
<211> LENGTH: 23
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 80
ttggatggga ttattttgga ttt                                               23

<210> SEQ ID NO 81
<211> LENGTH: 25
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 81
atccgaaata atcccatcca actac                                             25

<210> SEQ ID NO 82
<211> LENGTH: 18
<212> TYPE: DNA
<213> ORGANISM: Artificial Sequence
<220> FEATURE:
<223> OTHER INFORMATION: oligonucleotide for methylation analysis of
```

```
                             Septin 9

<400> SEQUENCE: 82
cgttaaccgc gaaatccg                                              18

<210> SEQ ID NO 83
<211> LENGTH: 19
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 83
cggatttcgc ggttaacgc                                             19

<210> SEQ ID NO 84
<211> LENGTH: 19
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 84
aactacgcgt taaccgcga                                             19

<210> SEQ ID NO 85
<211> LENGTH: 2582
<212> TYPE: DNA
<213> ORGANISM: Homo Sapiens

<400> SEQUENCE: 85
ctgcctagct ccttccttca caccttcctt cggaaacgtc tgctcctgac aaggtctact       60
tcctgctctc aggaggccct tattgtggag gaagggaggc gtcgcccgtc cctggcttct      120
ctgacagccg tgttccatcc ccgccctgtg ccccttctcc cggacagtgc cttctccagg      180
gctcacccag gagggtgcag cggtggcccc cggggcggtg gtcgtggtgg gggtgttagc      240
tgcaggggtg ccctcggtgg gtgggagttg gtggcctctc gctggtgcca tgggactcgc      300
atgttcgccc tgcgcccctc ggctcttgag cccacaggcc gggatcctgc ctgccagccg      360
cgtgcgctgc cgtttaaccc ttgcaggcgc agagcgcgcg gcggcggtga cagagaactt      420
tgtttggctg cccaaataca gcctcctgca gaaggaccct gcgcccgggg aaggggagga      480
atctcttccc ctctgggcgc ccgccctcct cgccatggcc cggcctccac atccgcccac      540
atctggccgc agcggggcgc ccgggggag gggctgaggc cgcgtctctc gccgtcccct       600
gggcgcgggc caggcgggga ggaggggggc gctccggtcg tgtgcccagg actgtccccc      660
agcggccact cgggccccag cccccaggc ctggccttga caggcgggcg gagcagccag       720
tgcgagacag ggaggccggt gcgggtgcgg gaacctgatc cgcccgggag gcggggccgg      780
ggcgggggcg cagcgcgcgg ggaggggccg gcgcccgcct tcctccccca ttcattcagc      840
tgagccaggg ggcctagggg ctcctccggc ggctagctct gcactgcagg agcgcgggcg      900
cggcgcccca gccagcgcgc agggcccggg ccccgccggg ggcgcttcct cgccgctgcc      960
ctccgcgcga cccgctgccc accagccatc atgtcggacc ccgcggtcaa cgcgcagctg     1020
gatgggatca tttcggactt cgaaggtggg tgctgggctg gctgctgcgg ccgcggacgt     1080
gctggagagg accctgcggg tgggcctggc gcggacggg ggtgcgctga ggggagacgg      1140
gagtgcgctg aggggagacg ggaccccaa tccaggcgcc ctcccgctga gagcgccgcg      1200
```

```
cgcccccggc cccgtgcccg cgccgcctac gtgggggacc ctgttagggg cacccgcgta    1260
gaccctgcgc gccctcacag gaccctgtgc tcgttctgcg cactgccgcc tgggtttcct    1320
tccttttatt gttgtttgtg tttgccaagc gacagcgacc tcctcgaggg ctcgcgaggc    1380
tgcctcggaa ctctccagga cgcacagttt cactctggga aatccatcgg tcccctccct    1440
ttggctctcc ccggcggctc tcgggccccg cttggacccg gcaacgggat agggaggtcg    1500
ttcctcacct ccgactgagt ggacagccgc gtcctgctcg ggtggacagc cctcccctcc    1560
cccacgccag tttcggggcc gccaagttgt gcagcccgtg ggccgggagc accgaacgga    1620
cacagcccag gtcgtggcag ggtctagagt gggatgtccc atggccccca tccaggcctg    1680
gggatatcct catccgcctc ccagaatcgg gccgtggggg acagaagggg cctgcgtgcg    1740
ggcagggaga gtattttggc tctctcctgt cttcggggtt tacaaagtgt gttgggactt    1800
gcggggctgc tctgtccaag cctgggtctg gcgtccgcgt ctctgagcct gtgagtgcgt    1860
gcgctttcct gcgtcctctt gactgccggt gctgggctc tgcgtcctgc gtccgcggga    1920
gtaaatacag caggcgaagg ggaagctcac acaatggtct ccagcgctct ggggcagggc    1980
ttctgagggg cgggcctgcc tctgccggga cctggagccc ccgcccctcg agaggctcc    2040 taggctgact tgggcagagc cctctggtgg gccgggaggg ggaaaggctg tgttgaaatg    2100
agcaaactgt ccaggtgtca ggccaagctg ggaggtgacc agcctgaggt cctcccgct    2160 ccatggccag aaccagggct gacatctggg tgtcctgagc ccagctgccc acacggccca    2220
cctggggtca gccctatctg agtggggag gcggggcctc ctgggggacc agaactttgg    2280
ctggacgcca agcagagtgc cagtggctgt tcttcagggc tgggcctgag gagggtgtgg    2340
ggcggcgaag ggacgggagg gggttgtgat ccagtggcca ctggcgctgt gcagagtgtg    2400
agctggaaac atcgtagtta ctttgtcagc ttagtggtga aagccctttt tcaggctcta    2460 tcccttttgca tccctgcttc ccagagggag gggaggtctg ggtctgcaga gctgggaggg    2520
cttgctgttc ccgccccct ccccacaac acctcctcat ctggacatct ttgggcacat    2580
gc                                                                  2582
```

<210> SEQ ID NO 86
<211> LENGTH: 99
<212> TYPE: DNA
<213> ORGANISM: Homo Sapiens

<400> SEQUENCE: 86

```
gacccgctgc ccaccagcca tcatgtcgga ccccgcggtc aacgcgcagc tggatgggat    60
catttcggac ttcgaaggtg ggtgctgggc tggctgctg                           99
```

<210> SEQ ID NO 87
<211> LENGTH: 68
<212> TYPE: DNA
<213> ORGANISM: Homo Sapiens

<400> SEQUENCE: 87

```
cgacccgctg cccaccagcc atcatgtcgg accccgcggt caacgcgcag ctggatggga    60
tcatttcg                                                             68
```

<210> SEQ ID NO 88
<211> LENGTH: 67
<212> TYPE: DNA
<213> ORGANISM: Homo Sapiens

<400> SEQUENCE: 88

```
gaagtccgaa atgatcccat ccagctgcgc gttgaccgcg gggtccgaca tgatggctgg    60
tgggcag                                                              67

<210> SEQ ID NO 89
<211> LENGTH: 139
<212> TYPE: DNA
<213> ORGANISM: Homo Sapiens

<400> SEQUENCE: 89
ctcgccgctg ccctccgcgc gacccgctgc ccaccagcca tcatgtcgga ccccgcggtc    60
aacgcgcagc tggatgggat catttcggac ttcgaaggtg ggtgctgggc tggctgctgc   120
ggccgcggac gtgctggag                                                139

<210> SEQ ID NO 90
<211> LENGTH: 119
<212> TYPE: DNA
<213> ORGANISM: Homo Sapiens

<400> SEQUENCE: 90
ccctccgcgc gacccgctgc ccaccagcca tcatgtcgga ccccgcggtc aacgcgcagc    60
tggatgggat catttcggac ttcgaaggtg ggtgctgggc tggctgctgc ggccgcgga   119

<210> SEQ ID NO 91
<211> LENGTH: 30
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 91
ccatcatatc aaacccaca atcaacacac                                       30

<210> SEQ ID NO 92
<211> LENGTH: 26
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 92
gtagtagtta gtttagtatt tatttt                                          26

<210> SEQ ID NO 93
<211> LENGTH: 17
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 93
cccaccaacc atcatat                                                    17

<210> SEQ ID NO 94
<211> LENGTH: 32
<212> TYPE: DNA
<213> ORGANISM: Artificial Sequence
<220> FEATURE:
<223> OTHER INFORMATION: oligonucleotide for methylation analysis of
      Septin 9

<400> SEQUENCE: 94
```

```
catcatatca aaccccacaa tcaacacaca ac                              32
```

<210> SEQ ID NO 95
<211> LENGTH: 25
<212> TYPE: DNA
<213> ORGANISM: Artificial Sequence
<220> FEATURE:
<223> OTHER INFORMATION: oligonucleotide for methylation analysis of
     Septin 9

<400> SEQUENCE: 95

```
gttcgaaatg attttattta gttgc                                     25
```

<210> SEQ ID NO 96
<211> LENGTH: 17
<212> TYPE: DNA
<213> ORGANISM: Artificial Sequence
<220> FEATURE:
<223> OTHER INFORMATION: oligonucleotide for methylation analysis of
     Septin 9

<400> SEQUENCE: 96

```
cgttgatcgc ggggttc                                              17
```

<210> SEQ ID NO 97
<211> LENGTH: 31
<212> TYPE: DNA
<213> ORGANISM: Artificial Sequence
<220> FEATURE:
<223> OTHER INFORMATION: 17378-7B3C3

<400> SEQUENCE: 97

```
ccatcatatc aaaccccaca atcaacacac a                              31
```

<210> SEQ ID NO 98
<211> LENGTH: 32
<212> TYPE: DNA
<213> ORGANISM: Artificial Sequence
<220> FEATURE:
<223> OTHER INFORMATION: 17378-7B5

<400> SEQUENCE: 98

```
atcatatcaa accccacaat caacacacaa ct                             32
```

<210> SEQ ID NO 99
<211> LENGTH: 31
<212> TYPE: DNA
<213> ORGANISM: Artificial Sequence
<220> FEATURE:
<223> OTHER INFORMATION: 17378-7B9

<400> SEQUENCE: 99

```
accatcatat caaaccccac aatcaacaca c                              31
```

<210> SEQ ID NO 100
<211> LENGTH: 32
<212> TYPE: DNA
<213> ORGANISM: Artificial Sequence
<220> FEATURE:
<223> OTHER INFORMATION: 17378-7B10

<400> SEQUENCE: 100

```
aaccatcata tcaaacccca caatcaacac ac                             32
```

<210> SEQ ID NO 101
<211> LENGTH: 31
<212> TYPE: DNA

```
<213> ORGANISM: Artificial Sequence
<220> FEATURE:
<223> OTHER INFORMATION: 17378-7B3C3

<400> SEQUENCE: 101
ccatcatatc aaacccaca atcaacacac a                                   31

<210> SEQ ID NO 102
<211> LENGTH: 24
<212> TYPE: DNA
<213> ORGANISM: Artificial Sequence
<220> FEATURE:
<223> OTHER INFORMATION: 17378.7PF2

<400> SEQUENCE: 102
gaaatgattt tatttagttg cgcg                                          24

<210> SEQ ID NO 103
<211> LENGTH: 15
<212> TYPE: DNA
<213> ORGANISM: Artificial Sequence
<220> FEATURE:
<223> OTHER INFORMATION: 17378.7PR2

<400> SEQUENCE: 103
tgatcgcggg gttcg                                                    15

<210> SEQ ID NO 104
<211> LENGTH: 15
<212> TYPE: DNA
<213> ORGANISM: Artificial Sequence
<220> FEATURE:
<223> OTHER INFORMATION: 17378.7PF4

<400> SEQUENCE: 104
cccgcgatca acgcg                                                    15

<210> SEQ ID NO 105
<211> LENGTH: 27
<212> TYPE: DNA
<213> ORGANISM: Artificial Sequence
<220> FEATURE:
<223> OTHER INFORMATION: 17378.7PR4

<400> SEQUENCE: 105
aactaaataa aatcatttcg aacttcg                                       27

<210> SEQ ID NO 106
<211> LENGTH: 65
<212> TYPE: DNA
<213> ORGANISM: Homo sapiens

<400> SEQUENCE: 106
gattcgttgt ttattagtta ttatgtcgga tttcgcggtt aacgcgtagt tggatgggat   60
tattt                                                               65

<210> SEQ ID NO 107
<211> LENGTH: 63
<212> TYPE: DNA
<213> ORGANISM: Homo sapiens

<400> SEQUENCE: 107
ccaccaacca tcatatcgaa ccccgcgatc aacgcgcaac taaataaat catttcgaac    60 ttc                                                                 63
```